(12) United States Patent
Day et al.

(10) Patent No.: US 7,790,762 B2
(45) Date of Patent: Sep. 7, 2010

(54) COMPOUNDS AND METHODS FOR THIOL-CONTAINING COMPOUND EFFLUX AND CANCER TREATMENT

(75) Inventors: Brian J. Day, Englewood, CO (US); Remy Kachadourian, Denver, CO (US)

(73) Assignee: National Jewish Health, Denver, CO (US)

( * ) Notice: Subject to any disclaimer, the term of this patent is extended or adjusted under 35 U.S.C. 154(b) by 103 days.

(21) Appl. No.: 11/280,959

(22) Filed: Nov. 15, 2005

(65) Prior Publication Data

US 2006/0135585 A1 Jun. 22, 2006

Related U.S. Application Data

(63) Continuation-in-part of application No. 10/400,980, filed on Mar. 27, 2003.

(60) Provisional application No. 60/422,802, filed on Oct. 31, 2002.

(51) Int. Cl.
*A61K 31/4164* (2006.01)
*C07D 233/60* (2006.01)
(52) U.S. Cl. .................... 514/396; 548/341.5
(58) Field of Classification Search ......... 514/396; 548/341.5
See application file for complete search history.

(56) References Cited

U.S. PATENT DOCUMENTS

| | | | |
|---|---|---|---|
| 5,075,116 | A | 12/1991 | LaHaye et al. |
| 5,238,683 | A | 8/1993 | Crystal |
| 5,310,732 | A | 5/1994 | Carson et al. |
| 5,489,519 | A | 2/1996 | Deeley et al. |
| 5,766,880 | A | 6/1998 | Deeley et al. |
| 5,889,049 | A | 3/1999 | Juergens |
| 5,948,814 | A | 9/1999 | Hwang et al. |
| 5,972,995 | A | 10/1999 | Fischer et al. |
| 5,985,261 | A | 11/1999 | White et al. |
| 5,989,521 | A | 11/1999 | Crystal |
| 5,994,339 | A | 11/1999 | Crapo et al. |
| 6,025,473 | A | 2/2000 | Deeley et al. |
| 6,127,356 | A | 10/2000 | Crapo et al. |
| 6,165,979 | A | 12/2000 | Kozhemyakin et al. |
| 6,329,422 | B1 | 12/2001 | Fischer et al. |
| 6,372,772 | B1 | 4/2002 | Kirkpatrick et al. |
| 6,432,923 | B1 | 8/2002 | Wattanasin et al. |
| 6,448,472 | B1 | 9/2002 | Thomas et al. |
| 6,635,627 | B1 | 10/2003 | Stoven et al. |
| 2002/0098185 | A1 | 7/2002 | Sims et al. |
| 2003/0073611 | A1 | 4/2003 | Gudkov et al. |
| 2003/0096762 | A1 | 5/2003 | Fischer et al. |
| 2004/0081647 | A1 | 4/2004 | Afeyan et al. |
| 2004/0087527 | A1 | 5/2004 | Day |

FOREIGN PATENT DOCUMENTS

| | | |
|---|---|---|
| EP | 1764363 | 3/2007 |
| JP | 63-270666 | * 11/1988 |
| WO | WO 97/16441 | 5/1997 |
| WO | WO98/53839 | 12/1998 |
| WO | WO9853839 | 12/1998 |
| WO | WO 01/46110 | 6/2001 |
| WO | WO02/070502 | 9/2002 |
| WO | WO 02/085297 | 10/2002 |
| WO | WO 03/086267 | 10/2003 |

OTHER PUBLICATIONS

Corvaisier, Andre :Studies of heterocyclic series. I. Synthesis of chalcones, O-hydroxychalcones, chremanones, and chromones derived from heterocyclic aldehydes 1962. CAS 57:69122.*
Reddy et al. "CAS Acession No. 1975:514280" 1975.*
Wani et al. "Plant antitumor agents. VI. Isolation and structure of taxol, a novel antileukemic and antitumor agent from *Taxus brevifolia*" Journal of the American Chemical Society, 1971, vol. 93, No. 9, pp. 2325-2327.*
Zhang et al., "Modulation of cisplatin cytotoxicity and cisplatin-induced DNA cross-links in hepG2 cells by regulation of glutathione-related mechanisms," Molecular Phamacology 2001, vol. 59, No. 4, pp. 837-843.
Schneldorfer et al., "Glutathione depletion causes cell growth inhibition and enhanced apoptosis in pancreatic cancer cells," Cancer magazine, Oct. 1, 2000, vol. 89, No. 7, pp. 1440-1447.
Wang, et al., "Differential susceptibilities to chronic beryllium disease contributed by different Glu69 HLA-DPB1 and DPA1 alleles," Journal of Immunology, vol. 163, Aug. 1999, pp. 1647-1653.
Costabel, "CD4/CD8 ratios in bronchoalveolar lavage fluid: of value for diagnosing sarcoidosis?," The European Respiratory Journal, Dec. 1997, 10(12), pp. 2699-2700.
Comhair, et al., "Increased glutathione and glutathione peroxidase in lungs of individuals with chronic beryllium disease," American Journal of Respiratory and Critical Care Medicine, Jun. 1999, 159(6), pp. 1824-1829.

(Continued)

*Primary Examiner*—Joseph R Kosack
(74) *Attorney, Agent, or Firm*—Faegre & Benson LLP

(57) ABSTRACT

Methods for therapy of cystic fibrosis and other conditions such as cancer are provided. The methods comprise one or more agents capable of increasing thiol-containing compound transport via a transporter system (i.e. ABC transporters such as MDR-1 or MRP-2) in cells. Other embodiments include the use of agents to modulate transport of thiol-containing compounds within the cell. Therapeutic methods involve the administration of such agents to a patient afflicted with cystic fibrosis, cancer and/or another condition responsive to stimulation of thiol-containing compound transport.

11 Claims, 21 Drawing Sheets

OTHER PUBLICATIONS

Batist et al., "Glutathione depletino in human and in rat multi-drug resistant breat cancer cell lines," Biochemical Pharmacology, 1991, vol. 41, No. 4, pp. 631-635.

Kurokawa et al., "Effect of glutathione depletion on cisplatin resistance in cancer cells transfected with the gammaglutamylcysteine synthetase gene," Japanese Journal of Cancer Research, 1997, vol. 88, No. 2, pp. 108-110.

Dimmock et al., "Cytotoxic activities of mannich bases of chalcones and related compounds," Journal of Medicinal Chemistry 1998, vol. 41, No. 7, pp. 1014-1026.

Zeng et al., "Expression of multidrug resistance protein-3 (multispecific organic anion transporter-D) in human embryonic kidney 293 cells confers resistance to anticancer agents," Cancer Research 1999, vol. 59, No. 23, pp. 5964-5967.

Moseley, R.H. et al., "Sulfasalazine-induced pulmonary disease," Dig Dis Sci, vol. 30, No. 9, pp. 901-904, Sep. 1985.

Williams, T., et al., Fibrosing alveolitis, bronchiolitis obliterans, and sulfasalazine, Chest, vol. 81, No. 6, pp. 766-768, Jun. 1982.

Bissonnette et al., "Inhibitory Effects of Sulfasalazine and Its Metabolites on Histamine Release and TNF-a Production by Mast Cells," the Journal of Immunology, vol. 156, pp. 218-223, 1996.

Nilubol, et al., Ulcerative Colitis and Sarcoidosis, The Mount Sinai Journal of Medicine, vol. 68, No. 6, pp. 400-402, Nov. 2001.

Dumot, et al., "Sarcoidosis Presenting as Granulomatous Colitis," The American Journal of Gastroenterology, vol. 93, No. 10, pp. 1949-1951, Oct. 1998.

Bewig, et al., "Crohn's Disease Mimicking Sarcoidosis in Bronchoalveolar Lavage," Respiration, vol. 66, pp. 467-469, 1999.

Vogin (https://www.hipusa.com/eTools/webmd/A-Z_Encyclopedia/sarcoidosistreatrnent.htm).

Rothkrantz-Kos, et al., "Decreased redox state in red blood cells from patients with sarcoidosis," Sarcoidosis Vasculitis and Diffuse Lung Diseases, vol. 19, pp. 1140120, 2002.

Buhl, et al., "Augmentation of flutathione in the fluid lining the epithelium of the lower respiratory tract by directly administering glutathione aerosol," Proc. Natl. Acad. Sci USA, vol. 87, pp. 4063-4067, Jun. 1990.

Won, et al., "Synthetic chalcones as potential anti-inflammatory and cancer chemopreventive agents," European Journal of Medicinal Chemistry, vol. 40, No. 1, pp. 103-112, Jan. 2005.

Nam, et al., "Cytotoxic 2',5'-dihydroxychalcones with unexpected antiangiongenic activity," European Journal of Medicinal Chemistry, vol. 38, No. 2, pp. 179-187, Feb. 2003.

Becq et al., "Possible regulation of CFTR-chloride channels by membrane-bound phophatases in pancreatic duct cells" FEBS Lett 1993 327(3):337-342.

Pan et al., "Bronchodilation from intravenous theophylline in patients with cystic fibrosis" Ped Pulmonol 1989 6(3):172, Database Medline Online Accession No. NLM2654849.

Pittet et al. J Immunol 2001, 166:1603-1610.

Borst et al., "A family of drug transporters: the multidrug resistance-associated proteins" J Natl Cancer Inst. Aug. 2000, 92(16):1295-1302.

Borst et al., "The multidrug resistance protein family" Biochim Biophys Acta 1999, 1461:347-357.

Illek et al., "Flavinoids stimulate Cl conductance of human airway epithelium in vitro and in vivo" Am J Physiol 1998, 275:L902-L910.

Konig et al., Conjugate export pumps of the multidrug resistance protein (MRP) family: localization, substrate specificity, and MRP2-mediated drug resistance Biochim Biophys Acta 1999, 1461:377-394.

Lai et al., "Role of glutathione in the multidrug resistance protein 4 (MRP4/ABCC4)- mediated efflux of cAMP and resistance to purine analogues" Biochem J 2002 361:497-503.

Lapperre et al., "Apocynin increases glutathione synthesis and activates AP-1 in alveolar epithelial cells" FEBS Lett 1999, 443:235-239.

Leslie et al., Toxicological relevance of the multidrug resistance protein 1, MRP1 (ABCC1) and related transporters, Toxicol 2001, 167:3-23.

Leslie et al., "Modulation of multidrug resistance protein 1 (MRP1/ABCC1) transport and ATPase activities by interaction with dietary flavonoids" Mol Pharmacol 2001, 59:1171-1180.

Linsdell et al., "Glutathione permeability of CFTR" Am J Physiol 1998, 275:C323-C326.

Loe et al., Verapamil stimulates glutathione transport by the 190-kDa multidrug resistance protein 1 (MRP)[1] J Pharmacol Exp Ther 2000, 293(2):530-538.

Narasaki et al., "Human canalicular multispecific organic anion transport (cMOAT) is expressed in human lung, gastric, and colorectal cancer cells" Biochem Biophys Res Comm 1997, 240:606-611.

O'Brien et al., "Glutathione peptidomimetic drug modulator of multidrug resistance-associated associated protein" J Pharmacol Exp Ther 1999, 291(3):1348-1355.

Rahman et al., "Differential regulation of glutathione by oxidants and dexamethsone in alveolar epithelial cells" Am J Physiol 1998, 275:L80-L86.

Rahman et al., "Oxidative stress and regulation of glutathione in lung inflammation" Eur Respir J 2000, 16:534-554.

Roum et al., "Glutathione aerosol suppresses lung epithelial surface inflammatory cell-derived oxidants in cystic fibrosis" Euro Respir J 1999, 87(1):438-443.

Salmon et al., "Proliferation of airway epithelium after ozone exposure" Am J Respir Crit Care Med 1998, 157:970-977.

Scheffer et al., "Multidrug resistance related molecules in human and murine lung" J Clin Pathol 2002, 55:332-339.

Velsor et al., "Antioxidant imbalance in the lungs of cystic fibrosis transmembrane conductance regulator protein mutant mice" Am J Lung Cell Mol Physiol 2001, 281:L31-L38.

Wang et al., "Actions of genistein on cystic fibrosis transmembrane conductance regulator channel gating" J Gen Physiol Mar. 1998, 111:477-490.

Brechot et al., "Different Pattern of MRP Localization on ciliated and basal cells from human bronchial epithelium" J Histochem Cytochem 1998, 46(4):513-517.

Illek et al., "Defective function of the cystic fibrosis-causing missense function G551D is covered by genistein" Am J Physiol 1999, 277:C833-C839.

Loe et al., Structure-activity studies of verapamil analogs' that modulate transport of leukotriene $C_4$ and reduced glutathione by multidrug resistance protein MRP[1] Biochem Biophys Res Comm 2000, 275:795-803.

Evers et al., "Vinblastine and sulfinpyrazone export by the multidrug resistance protein MRP2 is associated with glutathione export" Brit J Canc 2000, 83(3):375-383.

Demeule et al., "Dexamethasone modulation of multidrug transporters in normal tissues" FEBS Lett 1999, 442:208-214.

Laouari et al., "Two apical multidrug transporters, P-gp and MPP2, are differently altered in chronic renal failure" Am J Renal Physiol 2001, 280:F636-F645.

Dickinson et al., "Cellular glutathione and thiols metabolism" Biochem Pharmacol Sep. 2002, 64:1019-1026.

Efferth et al., "Activity of drugs from traditional chinese medicine toward sensitive and MDR1- or MDR1-overexpressing multidrug-resistant human CRF-CEM leukemia cells" Blood Cells Mol Dis Mar./Apr. 2002, 28(2):160-168.

Bard et al., "Expression of p-glycoprotein in killifish (Funduls heteroclitus) exposed to environmental xenobiotics" Aquat Toxicol 2002, 59(3-4):237-251.

Bard et al., "Expression of p-glycoprotein and cytochrom P450 1A in intertidal fish (Anplarchus purpurescens) exposed to environmental contaminants" Aquat Toxicol Oct. 2, 2002, 60(1-2)17-32.

Benderra et al., "Regulation of cellular glutathione modulates nuclear accumulation of daunorubicin in human MCF7 cells overexpressing multidrug resistance associated protein" Eur J Canc, Feb. 2000, 36(3):428-434.

Borst et al., "Mammalian ABC transporters in health and disease" Ann Rev Biochem 2002, 71:537-592.

Muller et al., "Role of multidrug resistance protein (MRP) in glutathione S-conjugate transport in mammalian cells" J Hepatol 1996, 24(Suppl. 1):100-108.

Kuwano et al., "Multidrug resistance-associated protein subfamily transporters and drug resistance" Anticancer Drug Des Apr. 1999, 14(2):123-131.

Abe et al., "Multidrug resistance protein" *Nippon Rinsho* May 1997, 55(5):1077-1082.

Broeks et al., "Homologues of the human multidrug resistance genes MRP and MDR contribute to heavy metal resistance in the soil nematode *Caenorhabditis elegans*" *EMBO J* Nov. 1996, 15(22):6132-6143.

Lin et al., "Up-regulation of multidrug resistance transporter expression by berberine in human and murine hepatoma cells" *Cancer* May 1, 1999, 85(9):1937-1942.

Supino et al., "A study of cross-resistance pattern and expression of molecular markers of multidrug resistance in a human small-cell lung-cancer cell line selected with doxorubicin" *Int J Cancer*, May 8, 1993, 54(2):309-314.

Suzuki et al., "The MRP family and anticancer drug metabolism" *Curr Drug/Metab* Dec. 2001, 2(4):367-377.

Van der Kolk et al., "Multidrug resistance protein MRP1, glutathione, and treated enzymes" in *Drug Resistance in Leukemia and Lymphima III*, Kaspers et al., eds., Kluwer Academic/Plenum Publishers, New York, Proceedings of the 3rd Int'l Symposium on Drug Resistance in Leukemia and Lymphoma, held Mar. 4-7.

Yamame et al., "Expression of multidrug resistance protein/GS-X pump and γ-glutamylcysteine synthetase genes is regulated by oxidative stress" *J Biol Chem* Nov. 20, 1998, 273(47):31075-31085.

Iida et al., "Hammerhead ribozyme against γ-glutamylcysteine synthetase sensitized human colonic cancer cells to cisplatin by down-regulating both the glutathione synthesis and the expression of multidrug resistance proteins" *Cancer Gene Ther* Oct. 2001, 8(10):803-814.

Jedlitschky et al., "Transport of glutathione, glucuronate, and sulfate conjugates by the MRP gene-encoded conjugate export pump" *Cancer Res* Mar. 1, 1996, 56(5):988-994.

Ko et al., "Cystic fibrosis: A brief look at some highlights of a decade of research focused on elucidating and correcting the molecular basis of the disease" *J Bioenergetics & Biomembranes* Dec. 2001, 33(6):513-521.

Yamazaki et al., "Recent advances in carrier-mediated hepatic uptake, and biliary excretion of xenobiotics" *Pharm Res* Apr. 1996, 13(4):497-513.

Gottesman et al., "Overview: ABC Transporters and Human Disease" *Bioenergetics & Biomembranes* Dec. 2001, 33(6):453-458.

Batist et al., "Glutathione depletino in human and in rat multi-drug resistant breast cancer cell lines" Biochem Pharmacol 1991, 41(4):631-5.

Awasthi et al., "Modulation of Cisplatin Cytotoxicity by Sulphasalazine" Br J Cancer 1994, 70(2):190-4.

Kurokawa et al., "Effect of Glutathione Depletion on Cisplatin Resistance in Cancer Cells Transfected with the Gammaglutamylcysteine Synthetase Gene" Jpn J Cancer Res 1997, 88(2):108-10.

Dimmock et al., "Cytotoxic Activities of Mannich Bases of Chalcones and Related Compounds" J Med Chem 1998, 41 (7):1014-26.

Zeng et al., "Expression of Multidrug Resistance Protein-3 (Multispecific Organic Anion Transporter-D) in Human Embryonic Kidney 293 Cells Confers Resistance to Anticancer Agents" Cancer Res.1999, 59(23):5964-7.

Schnelldorfer et al., "Glutathione Depletion Causes Cell Growth Inhibition and Enhanced Apoptosis in Pancreatic Cancer Cells" Cancer 2000, 89(7):1440-7.

Zhang et al., "Modulation of Cisplatin Cytotoxicity and Cisplatin-Induced DNA Cross-Links in HepG2 Cells by Regulation of Glutathione-Related Mechanisms" Mol Pharmacol 2001, 59(4): 837-43.

\* cited by examiner

FIG. 16
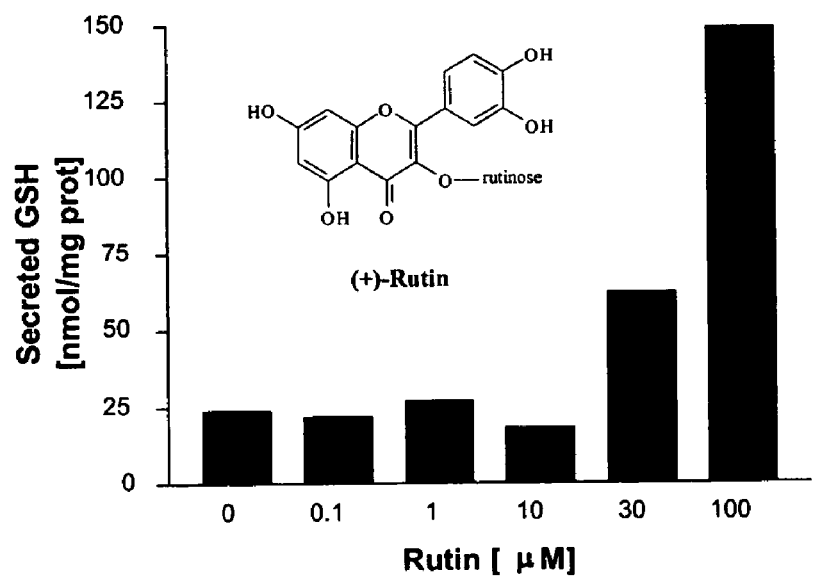
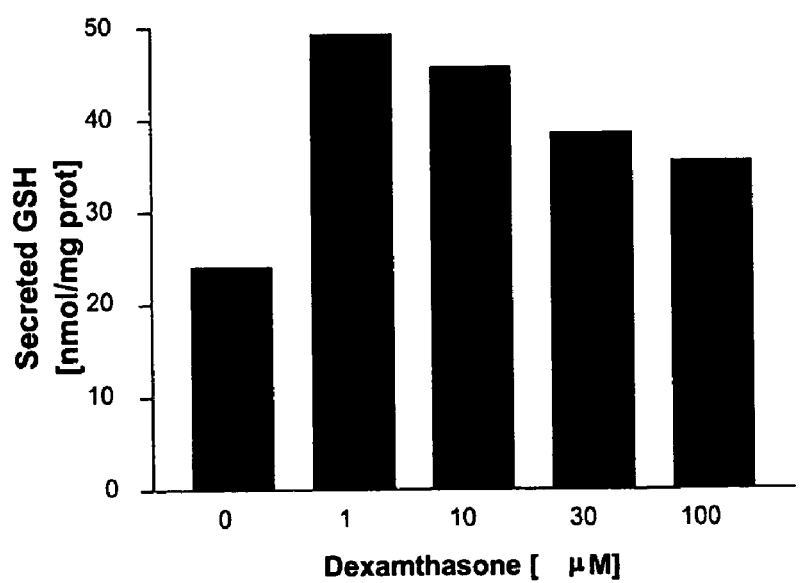

A
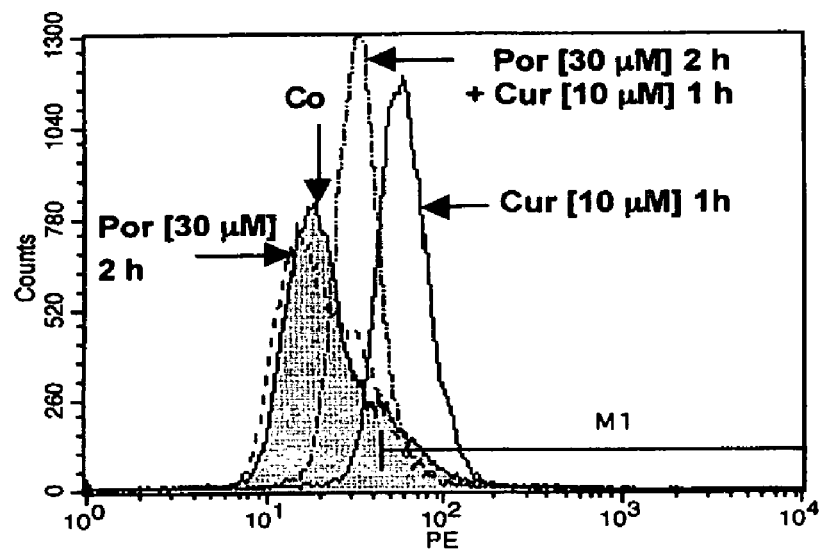
B
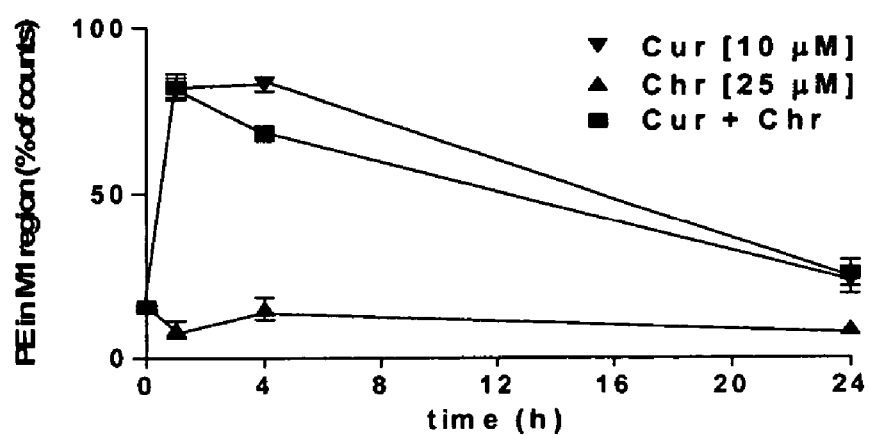
FIG. 21

SEQUENCE LISTING

<160> NUMBER OF SEQ ID NOS: 4

<210> SEQ ID NO 1
<211> LENGTH: 24
<212> TYPE: DNA
<213> ORGANISM: Murine MDR1

<400> SEQUENCE: 1
ctcaccaagc gactccgata catg                                    24

<210> SEQ ID NO 2
<211> LENGTH: 27
<212> TYPE: DNA
<213> ORGANISM: Murine MDR1

<400> SEQUENCE: 2
gataattcct gtgccaaggt ttgctac                                 27

```
<210> SEQ ID NO 3
<211> LENGTH: 25
<212> TYPE: DNA
<213> ORGANISM: Murine MDR2

<400> SEQUENCE: 3
aagacaaaga ttctagtgtt ggacg                                    25

<210> SEQ ID NO 4
<211> LENGTH: 26
<212> TYPE: DNA
<213> ORGANISM: Murine MDR2

<400> SEQUENCE: 4
agatatgcca gagatcagtt cacacc                                   26
```

COMPOUNDS AND METHODS FOR THIOL-CONTAINING COMPOUND EFFLUX AND CANCER TREATMENT

RELATED APPLICATIONS

This is a continuation-in-part of U.S. patent application Ser. No. 10/400,980, which claims the benefit under 35 U.S.C. §119(e) of provisional U.S. patent application Ser. No. 60/422,802, filed on Oct. 31, 2002.

STATEMENT REGARDING FEDERALLY SPONSORED RESEARCH OR DEVELOPMENT

The studies disclosed herein were supported in part by grant NIH HL075523 from the National Institutes of Health NIH. The U.S. government may have certain rights to the subject invention. [35 U.S.C. §202].

FIELD

The present invention relates to compounds and methods for glutathione efflux and cancer treatment. More particularly one embodiment relates to compounds which may be used to activate a thiol-containing compound transporter in cancerous cells or tissue in combination with other cancer treatments. The present invention also pertains to substituted phenol compounds and methods for using the same. In particular, compounds of the present invention are useful for treatment of diseases associated with thiol-containing compound transport.

BACKGROUND

Cystic fibrosis is a lethal genetic disease afflicting approximately 30,000 individuals in the United States. Since 1 in 2500 Caucasians is born with cystic fibrosis, it is the most common lethal, recessively inherited disease in that population. This inherited disorder impairs epithelial ion transport, particularly that of chloride. Cystic fibrosis affects the secretory epithelia of a variety of tissues, altering the transport of water, salt and other solutes into and out of the blood stream. In particular, the ability of epithelial cells in the airways, pancreas and other tissues to transport chloride ions, and accompanying sodium and water, is severely reduced in cystic fibrosis patients, resulting in respiratory, pancreatic and intestinal ailments. The principle clinical manifestation of cystic fibrosis is the resulting respiratory disease, characterized by airway obstruction due to the presence of thick mucus that is difficult to clear from airway surfaces. This thickened airway liquid contributes to recurrent bacterial infections and progressively impaired respiration. Death may occur in severe cases because of chronic lung infections, especially by *Pseudomonas aeruginosa*, which cause a slow decline in pulmonary function.

One current treatment for CF patients focus on controlling the symptoms of infections through antibiotic therapy and promoting mucus clearance by use of postural drainage and chest percussion. However, even with such treatments, frequent hospitalization is often required as the disease progresses. Thus, long-term therapies are needed for these patients.

There are approximately 50 known ATP-binding cassette (ABC) transporters in humans, and there are currently about 13 genetic diseases associated with defects in 14 of these transporters. The most common genetic disease conditions include cystic fibrosis, Stargardt disease, age-related macular degeneration, adrenoleukodystrophy, Tangier disease, Dubin-Johnson syndrome and progressive familial intrahepatic cholestasis. At least 8 members of this family are involved in the transport of a variety of amphipathic compounds, including anticancer drugs, and some appear to contribute to the resistance of cancer cells to chemotherapy. (Gottesman M M, Ambudkar S V, "Overview: ABC transporters and human disease." J Bioenerg Biomembr 2001, 33(6): 453-8.). ABC transporters are found in all known organisms, and approximately 1,100 different transporters belonging to this family have been described in the literature. The family is defined by homology within the ATP-binding cassette (ABC) region. Most family members also contain transmembrane domains involved in recognition of substrates, which are transported across, into, and out of cell membranes, but some members utilize ABCs as engines to regulate ion channels.

Two different integral glycoproteins, the 170 kD P-glycoprotein (P-gp) and the 190 kD multi-drug resistance protein (MRP), are involved in the acquisition of multi-drug resistance phenotypes in cancer cells. Even though they are members of the ABC superfamily, the primary structures are quite different, only about 15% of the amino acids are identical. Nevertheless, MRP and P-gp confer resistance to a similar profile of chemotherapeutic agents and play a similar role in the acquirement of multi-drug resistance. Recently, MRP demonstrated the ability to transport the cysteinyl leukotriene, leukotriene C4 (LTC4) (Ding G Y, Shen T, Center M S. Multidrug resistance-associated protein (MRP) mediated transport of daunomycin and LTC4 in isolated plasma membrane vesicles. Anticancer Res 1999; 19:3243-8.), and other glutathione conjugates, suggesting that MRP has a function different from P-gp. MRP is an ATP-dependent glutathione S-conjugate carrier (GS-X pump) and is present in membranes of many, if not all, cells. Overexpression of MRP in tumor cells contributes to resistance to natural product drugs and oxyanions In cystic fibrosis, defective chloride transport is generally due to a mutation in a chloride channel known as the cystic fibrosis transmembrane conductance regulator (CFTR; see Riordan et al., Science 245:1066-73, 1989), another member of the ABC transporter family. CFTR is a linear chloride channel found in the plasma membrane of certain epithelial cells, where it regulates the flow of chloride ions in response to phosphorylation by a cyclic AMP-dependent kinase. Many mutations of CFTR have been reported, the most common of which is a deletion of phenylalanine at position 508 (.DELTA.F508-CFTR), which is present in approximately 70% of patients with cystic fibrosis. A glycine to aspartate substitution at position 551 (G55 ID-CFTR) occurs in approximately 1% of cystic fibrosis patients.

In a healthy lung, glutathione (GSH) is present in high concentrations in the epithelial lining fluid (ELF) of the lower respiratory tract, with normal levels in human ELF being more than 200-fold greater than that in plasma. ELF GSH is a major component of the screening process that protects the pulmonary epithelium from oxidants released by inflammatory cells as well as inhaled oxidants. In addition, ELF GSH helps maintain the normal function of the immune components of the pulmonary epithelial host defense system. However, in certain conditions, such as idiopathic pulmonary fibrosis and AIDS patients, a substantial ELF GSH deficiency exists. Oral administration of GSH does not achieve significant elevation of GSH level in the lungs and intravenous administration of GSH is associated with a very short plasma half-life of the molecule. Thus, a problem exists in supplementing GSH by conventional means.

Glutathione (GSH) is a multipurpose mono-thiol compound. Pure GSH forms a flaky powder that retains a static electrical charge, due to triboelectric effects, that makes processing difficult. Glutathione is a strong reducing agent, so that autooxidation occurs in the presence of oxygen or other oxidizing agents.

In synthesizing GSH in the body, cysteine, a thiol amino acid is required. Since oral administration of glutathione is ineffective, prodrugs or precursor therapy have been advocated. Administration of cysteine, or a more bioavailable precursor of cysteine, N-acetyl cysteine (NAC) was suggested. While cysteine and NAC are both, themselves, oxygen scavengers, their presence competes with GSH for resources in certain reducing (GSH recycling) pathways. Since GSH is a specific substrate for many reducing pathways, the loading of a host with cysteine or NAC may result in less efficient utilization or recycling of GSH. Thus, cysteine and NAC are not ideal GSH prodrugs to solve a deficiency in GSH. Thus, while GSH may be degraded, transported as amino acids, and resynthesized in the cell, there may also be circumstances where GSH is transported into cells without degradation; and in fact the administration of cysteine or cysteine precursors may interfere with this process. Thus, loading up on the precurser products is also a problem.

A number of disease states have been specifically associated with reductions in GSH levels. Depressed GSH levels, either locally in particular organs, or systemically, have been associated with a number of clinically defined diseases and disease states. These include HIV/AIDS, diabetes and macular degeneration, all of which progress because of excessive free radical reactions and insufficient GSH. Other chronic conditions may also be associated with GSH deficiency, including heart failure and coronary artery restenosis post angioplasty.

Diabetes afflicts 8% of the United States population and consumes nearly 15% of all United States healthcare costs. HIV/AIDS has infected nearly 1 million Americans. Current therapies cost in excess of $20,000 per year per patient, and are rejected by, or fail in 25% to 40% of all patients. Macular degeneration presently is considered incurable, and will afflict 15 million Americans by 2002.

Studies have demonstrated insufficient GSH levels are linked to these diseases. Newly published data implies that diabetic complications are the result of hyperglycemic episodes that promote glycation of cellular enzymes and thereby inactivate GSH synthetic pathways. The result is GSH deficiency in diabetics, which may explain the prevalence of cataracts, hypertension, occlusive atherosclerosis, and susceptibility to infections in these patients.

GSH also functions as a detoxicant by forming GSH S-conjugates with carcinogenic electrophiles, preventing reaction with DNA, and chelation complexes with heavy metals such as nickel, lead, cadmium, mercury, vanadium, and manganese. GSH plays a role in protein folding and deficiencies affect many proteins including surfactins and defensens.

SUMMARY OF THE EMBODIMENTS

Certain embodiments of the present invention satisfy a need in the treatment of thiol-containing compound deficient conditions namely, cystic fibrosis. The embodiments fulfill this need and further provide other related advantages for other disease treatments:

Some of the embodiments provide compositions and methods for therapy of cystic fibrosis and other conditions such as cancer treatments. These embodiments are directed to a method for the modulation of thiol-containing compound transport in cells. In one embodiment, thiol-containing compound transport is conferred through over-expression by genetic manipulation of an ABC transporter. In other embodiments, excretion of thiol-containing compounds is conferred through increasing the activity of at least one existing ABC transporter using several classes of known pharmaceutical agents as well as some novel compounds. Confirmation of transport is useful to achieve restoration of thiol-containing compounds in biotechnology applications, and for restoration of thiol-compounds within cellular compartments, in tissues and whole organs. In other embodiments, increased secretion of thiol-containing compounds is used to treat diseases with thiol-containing compound excretion deficiencies (i.e. cystic fibrosis (CF), idiopathic pulmonary fibrosis (IPF) and acquired immune deficiency syndrome (AIDS), pancreatic disease, vascular disease (i.e. vasculitis, artherosclerosis), cancer, intestinal disease (i.e. inflammatory bowel disease) neurodegenerative disease (i.e. Parkinsons, Alzheimers) and also male infertility problems).

Within other aspects of the embodiments, methods for treating cystic fibrosis in a patient, comprising administering a compound selected from the group consisting of one of the classes flavanone, flavone, isoflavone, flavanol, 1,4-naphthoquinone, 3-phenylcoumarin, 2-phenyl-4-quinoline, 1-triflavone, thioflavin, benzoic acid derivative, indole derivative, naturally occurring alkaloids, steroids and non-steriod anti-inflammatories (NSAID) wherein the compound is capable of stimulating thiol-containing compound transport. Within certain embodiments, the compound may include but not limited to dexamethasone, rutin, berberine, biochanin A, indomethacin, propyl gallate, p-aminosalicylate, probenacid or sulfasalazine.

Within further related aspects, method are described for increasing thiol-compound excretion by airway epithelial cells of a patient afflicted with cystic fibrosis. One method includes administering to a mammal one or more compounds selected from several classes of chemicals for example flavanone, flavone, isoflavone, isoflavanone 1,4-naphthoquinone, 3-phenylcoumarin, 2-phenyl-4-quinoline, 1-triflavone, thioflavin, benzoic acid derivative, indole derivative, naturally occurring alkaloids, steroids and non-steriod anti-inflammatories (NSAID).

Other embodiments include combination therapies for the treatment of cancer. Within further related aspects, methods are described for increasing thiol-compound excretion by tumor cells of a subject afflicted with cancer in combination with an anti-cancer treatment. These anti-cancer treatments may include chemotherapy, radiation therapy, hyperthermia or combination thereof. Within other aspects of the embodiments, methods for treating cancer in a patient, comprising administering a compound selected from the group consisting of one of the classes flavones and chalcones, as well as novel compounds disclosed herein. Within certain embodiments, the compound may include but are not limited to 5-hydroxyflavone, 7-hydroxyflavone, chrysin (5,7 dihydroxyflavone), galangin (3,5,7 trihydroxyflavone), baicalein (5,6,7 trihydroxyflavone), apigenin (tetrahydroxyflavone), kaempferol (3,5,7,4'quadrahydroxyflavone) fisetin, quercetin, morin, myricetin, pinocembrin, pinobanskin, rutin (3=O-rutinose), 2' hydroxychalcone, 3' hydroxychalcone, 4-hydroxychalcone, 2' 2 dihydroxychalcone, 2' 3 dihydroxychalcone, 2' 4 dihydroxychalcone, 2' 4' dihydroxychalcone, 2' 5' dihydroxychalcone, 2',4',4 trihydroxychalcone and 2',3', 4' trihydroxychalcone.

DEFINITIONS

The terms "drug resistant" or "drug resistance" as used herein to describe a property of a cell refer to the ability of the cell to withstand without cytotoxicity increased concentrations of a drug as compared to an appropriate control cell. An appropriate control cell for a cell that has been made drug resistant by continued exposure to a drug is the parental cell from which the drug resistant cell was derived. An appropriate control cell for a cell which has been made drug resistant by expression in the cell of a protein that confers drug resistance on the cell is the same cell without the protein expressed. Appropriate control cells for naturally occurring cells in vivo made drug resistant by continued exposure to a drug are the same cells at the time of initial exposure to the drug (parental cell line).

Homology refers to sequence similarity between sequences and can be determined by comparing a position in each sequence that may be aligned for purposes of comparison. When a position in the compared sequence is occupied by the same nucleotide base or amino acid, then the molecules are homologous at that position. A degree of homology between sequences is a function of the number of matching or homologous positions shared by the sequences.

The term "sequences having substantial sequence homology" means those nucleotide and amino acid sequences that have slight or inconsequential sequence variations from the sequences disclosed herein (thiol-containing compound transporters) i.e. the homologous nucleic acids function in substantially the same manner to produce substantially the same polypeptides as the actual sequences. The variations may be attributable to local mutations or structural modifications. It is expected that substitutions or alterations can be made in various regions of the nucleotide or amino acid sequence without affecting protein function, particularly if they lie outside the regions predicted to be of functional significance.

The term "transformant host cell" is intended to include prokaryotic and eukaryotic cell that have been transformed or transfected with a recombinant expression vector. The terms "transformed with", "transfected with", "transformation" and "transfection" are intended to encompass introduction of nucleic acid (e.g. a vector) into a cell by one of many possible techniques. The recombinant expression vectors can be used to make a transformant host cell including the recombinant expression vector. Prokaryotic cells can be transformed with nucleic acid by, for example, electroporation or calcium-chloride mediated transformation. Nucleic acid can be introduced into mammalian cells via conventional techniques such as calcium phosphate or calcium chloride coprecipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks).

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells that do not contain a recombinantly introduced exogenous DNA segment or gene. Recombinant cells include those having an introduced cDNA or genomic gene, and also include genes positioned adjacent to a heterologous promoter not naturally associated with the particular introduced gene.

The term "purified protein or peptide" as used herein, is intended to refer to a composition, isolatable from other components, wherein the protein or peptide is purified to any degree relative to its naturally occurring state (i.e. relative a cell extract). A purified protein or peptide therefore also refers to a protein or peptide, free from the environment in which it may naturally occur. Generally, "purified" will refer to a protein or peptide composition which has been subjected to fractionation to remove various other components, and which composition substantially retains its expressed biological activity. Where the term "substantially purified" is used, this will refer to a composition in which the protein or peptide forms the major component of the composition, such as constituting about 25% or more of the proteins in the composition.

The term "subject" is intended to include living organisms in which an immune response can be elicited, e.g., mammals. Examples of subjects include humans, dogs, cats, rats, mice and transgenic species thereof.

The phrases "pharmaceutically or pharmacologically acceptable" refer to molecular entities and compositions that do not produce an adverse, allergic or other untoward reaction when administered to an animal, or a human, as appropriate.

The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject.

"Liposome" is a generic term encompassing a variety of single and multilamellar lipid vehicles formed by the generation of enclosed lipid bilayers. Phospholipids are used for preparing the liposomes accordingly and can carry a net positive charge, a net negative charge or are neutral. Dicetyl phosphate can be employed to confer a negative charge on the liposomes, and stearylamine can be used to confer a positive charge on the liposomes.

The term "flavones", as used herein refers to a compound based on the core structure of flavone. Non-limiting examples of flavones encompassed by this invention are apiin, myricetin, quercetin, luteolin, rutin, kampferol, and apigenin.

An "isoflavone" is an isomer of a flavone (i.e., the phenyl moiety at position 2 is moved to position 3), and having the core structure shown below. Non-limiting examples of isoflavones encompassed by this invention are genistein, daidzein, biochanin A, baptigenin and formononetin.

A "flavanone" is an isomer of flavone (the C ring is not aromatic), and have the core structure shown below. Non-limiting examples of flavanones encompassed by this invention are taxifolin, naringenin, naringin, eriodictyol, and fustin.

A "flavanol" is an isomer of flavanone (the C ring is not aromatic and lacks an oxo group) and having the core structure shown below: An example is catechin.

"Alkyl" means the monovalent linear or branched saturated hydrocarbon moiety, consisting solely of carbon and hydrogen atoms, having from one to twelve carbon atoms. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means isopropyl, isobutyl, tert-butyl, "Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Optionally substituted", when used in association with "aryl", phenyl", "heteroaryl" (including pyridinyl, pyrimidinyl, pyridazinyl, pyrazinyl, oxazolyl, thiazolyl, isoxazolyl, isothiazolyl, imidazolyl, pyrazolyl and quinolinyl)" or "heterocyclyl", means an aryl, phenyl, heteroaryl or heterocyclyl which is optionally substituted independently with one to four substituents, preferably one or two substituents selected from alkyl, cycloalkyl, alkoxy, halo, haloalkyl, haloalkoxy, cyano, nitro, heteroalkyl, amino, acylamino, mono-alkylamino, di-alkylamino, hydroxyalkyl, alkoxyalkyl, benzyloxy, cycloalkylalkyl, cycloalkoxy, cycloalkylalkoxy, alkylsulfonyloxy, optionally substituted thienyl, optionally substituted pyrazolyl, or optionally substituted pyridinyl "Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

A "chalcone" is an intermediate in the biosynthesis of flavonoids, and have the core structure shown below. Non-limiting examples of flavanones encompassed by this invention are 2' hydroxychalcone, 3' hydroxychalcone, 4-hydroxychalcone, 2' 2 dihydroxychalcone, 2' 3 dihydroxychalcone, 2' 4 dihydroxychalcone, 2' 4' dihydroxychalcone, 2' 5' dihydroxychalcone, 2',4',4 trihydroxychalcone and 2',3',4' trihydroxychalcone.

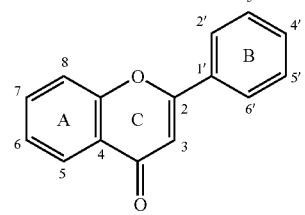

Flavones 7-apioside,5,4'-OH Apiin
3,5,7,3',4',5'-OH Myricetin
3,5,7,3',4'-OH Quercetin
5,7,3',4'-OH Luteolin
3-rutinose,5,7,3',4'-OH Rutin
3,5,7,4'-OH Kampferol
5,7,4'-OH Apigenin

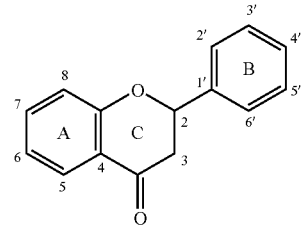

Flavanones 3,5,7,3',4'-OH Taxifolin
5,7,4'-OH Naringenin
7-raminose,5,4'-OH Naringin
5,7,4',5'-OH Eriodictyol
3,7,3',4'-OH Fustin

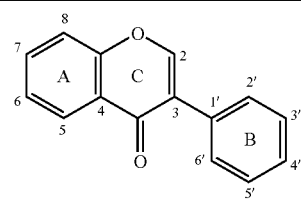

Isoflavones 5,7,4'-OH Genistein
7,4'-OH Daidzein
5,7,4'(OCH$_3$)-OH Biochanin A
7,3',4',5'-OH Baptigenin
7,4'(OCH$_3$)-OH Formononeti

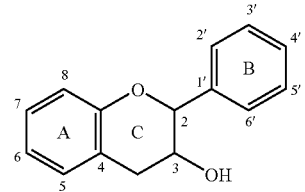

Flavanols 3,5,7,3',4'-OH Catechin

Chalcones

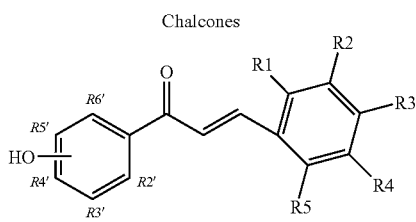

2' hydroxychalcone, 3' hydroxychalcone, 4-hydroxychalcone, 2' 2 dihydroxychalcone, 2' 3 dihydroxychalcone, 2' 4 dihydroxychalcone, 2' 4' dihydroxychalcone, 2' 5' dihydroxychalcone, 2',4',4 trihydroxychalcone 2',3',4' trihydroxychalcone.

The term "benzoic acid derivatives" as used herein refers to a compounds based on the core structure of benzoic acid. Examples and structures (one or more carboxylic acid group(s) can be substituted at any of the 6 carbons of the benzene ring) are shown below:

Benzoic Acid Derivatives

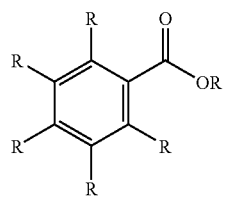

Acetylsalicylsaliclic acid (2-(aceyl-oxy)benzoic acid 2-carboxyphenyl ester)
Ambucaine (4-amino-2-butoxybenzoic acid 2-diethylaminoethyl ester)
p-Aminosalicylic acid (4-amino-2-hydroxybenzoic acid)
p-Aminosalicylic acid hydrazide (4-amino-2-hydroxybenzoic acid hydrazide)
p-Aminosulfobenzoic acid (4-amino-2-sulfobenzoic acid)
Anacardic acid
p-Anisic acid (4-methoxybenzoic acid)
o-(p-Anisoyl)benzoic acid (2-(-4-methoxybenzoyl)benzoic acid)
Aspirin (2-(acetyloxy)benzoic acid)
Avobenzone (1-[4-(1,1-dimethylethyl)phenyl]-3-(4-methoxyphenyl)-11,3-propanedione)
Benzoic acid
Benzonatate (4-(butylamino)benzoic acid)
Benzoylpas (4-(benzoylamino)-2-hydroxybenzoic acid)
Benzyl salicylate (2-hydroxybenzoic acid phenylmethylester)
Betoxycaine (3-amino-4-butoxybenzoic acid 2-[2-(dimethylamno)ethoxy]ethyl ester)
m-,o-, p-Chlorobenzoic acid
m-,o-, p-Cresotic acid
Cuelure (4-[4-(acetyloxy)phenyl]-2-butanone)
Cumic acid (4-(1-methylethyl)benzoic acid)
Difunisal (2',4'-difluoro-4-hydroxy-[1,1'-biphenyl]-3-carboxylic acid)
Ethylparaben (4-hydroxybenzoic acid ethyl ester)
Gallic acid (3,4,5-trihydroxybenzoic acid)
m-,o-,p-Hydroxybenzoic acid
Mesalamine (5-amino-2-hydroxybenzoic acid)
Methylparaben (4-hydroxybenzoic acid methylester)
Methyl salicylate (2-hydroxybenzoic acid methyl esther)
o-Orsellinic acid (2,4-dihydroxy-6-methylbenzoic acid)
Propyl gallate (3,4,5-trihydroxy-benzoic acid propyl ester)
Propylparaben (4-hydroxybenzoic acid propyl ester)
Salicylic acid (2-hydroxybenzoic acid)
Salicylsulfuric acid (2-(sulfooxy)benzoic acid)
Salsalate (2-hydroxybenzoic acid carboxyphenyl ester)
Sulfosalicylic acid (5-hydroxy-5-sulfo-benzoic acid)
Thiosalicylic acid (2-mercaptobenzoic acid)
Vanillic acid (4-hydroxy-3-methoxybenzoic acid)

The term "indole derivatives" as used herein refers to a compounds based on the core structure of indole. Examples and structures are shown below:

Indole Derivatives

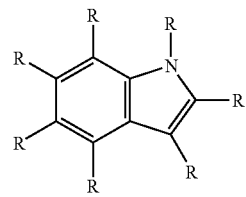

Adrenolutin (1-methyl-1H-indole-3-5,6-triol)
Aminochromes (2,3-dihydroindole-5,6-quinone)
5-Hydroxytryptophan
Hypaphorine (1-trimehyl-ammonio-3-(3-indolyl)propionate)
Indalpine (3-[2-(4-piperidinyl)ethyl]-1H-indole)
Indapamide (3-(aminosulfonyl)4-chloro-N-(2,3-dihydro-2-methyl-1H-indol-1-yl)benzamide)
Indican (indol-3-yl sulfate)
Indican (3-(β-glucosido)indole)
Indigo (2-(1,3-dihydro-3-oxo-2H-indol-2-ylidene)-1,2-dihydro-3H-indol-3-one))
Indigo Carmine (2-(1,3-dihydro-3-oxo-5-sulfo-2H-indol-2-ylidene)-2,3-dihydro-3-oxo-1H-indole-5 sulfonic acid)
Indo-1 (2-[4-[Bis(carboxymethyl)-amino]-3-[2-[2-[bis(caroxymethyl)amino]-5-methylphenoxyl]-ethoxy]phenyl]-1H-indole-6-carboxylic acid)
Indobufen (4-(1,3-dihydro-1-oxo-2H-isoindol-2-yl)-α-ethylbeneneacetic acid
Indole (2,3-benzopyrrole)
Indoleacetic acid (1H-indole-3-acetic acid)
Indolebutyric acid (1H-indole-3-butanoic acid)
Indolmycin ((5S)-5-[(1R)-1-(1H-indol-3-yl)ethyl]-2-(methylamino)4(5H)-oxazolone)
Indomethacin (1-(4-chlorobenzoyl)-5-methoxy-2-methyl-1H-indole-3-acetic acid)
Indoprofen (4-(1,3-dihydro-1-oxo-2H-isoindol-2-yl)-a-methylbenzeneacetic acid)
Indoramin (N-[1-(2-[1H-indol-3-yl)ethyl]4-piperidinyl]benzamide)
Isatin (indole-2,3-dione)
Psilocin (3-[2-(dimethylamino)ethyl]-1H-indol-4-ol)
Psilocybin (3-[2-(dimethylamino)ethyl]-1H-indol-4-ol)
Serotonin
Skatole (3-methyl-1H-indole)

Synthesis of Substituted Phenol Compounds

Chalcones may be synthesized by a base-catalyzed Claisen-Schmidt condensation of an aromatic aldehyde with the appropriate acetophenone, the catalyst can be NaOH or KOH or other catalyst known in the art. For the synthesis of hydroxylated chalcones, protection of the phenolic groups on the acetophenone may be needed for improved product yields. The hydroxyl group on the acetophenone may be protected with 2H-3,4-dihydropyrane, and the protecting group may be removed by acid hydrolysis to give the hydroxychalcone, which can be purified by column chromatography (in silica gel using chloroform as eluant) (Liu et. al. (2001). *Journal of Medicinal Chemistry*, 44, 4443-4452):

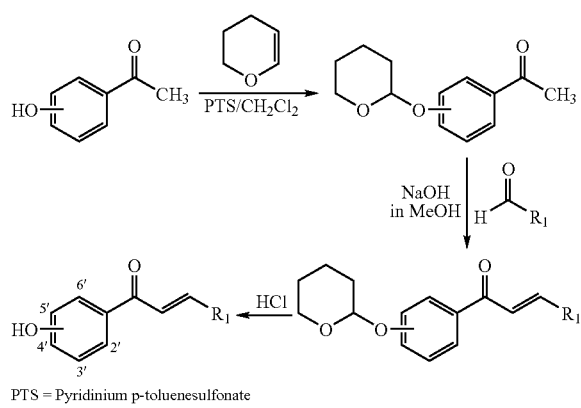

PTS = Pyridinium p-toluenesulfonate

Alternative methods of chalcone synthesis have been described, including one based on the Suzuki reaction (Eddarir et al. (2003) *Tetrahedron Letters*, 44, 5359-5363). Any known method in the art for synthesizing chalcones is contemplated herein.

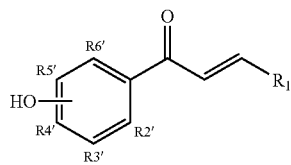

Pharmacophores

In one embodiment, a substituted phenol compound comprises the formula above where a hydroxyl group may be in position 2' or 3'. In another embodiment, a substituted phenol compound of the formula comprises a formula wherein two hydroxyl groups may be in positions 2' and 6' or in 2' and 5' or in 2' and 3'. In one embodiment, a substituted phenol compound of the formula above comprises a formula wherein two hydroxyl groups may be in positions 2' and 6'. In some other embodiments, a substituted phenol compound of the formula above comprises a formula wherein $R^1$ is an optionally substituted heteroaryl. For example, the optionally substituted heteroaryl may be an optionally substituted nitrogen atom containing 5-membered heteroaryl.

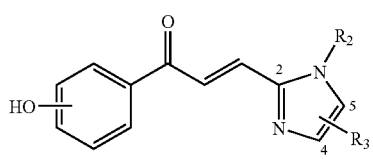

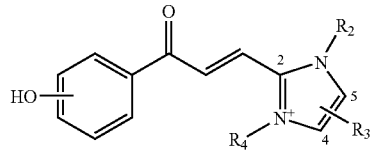

In another embodiment, a substituted phenol compound of the above formula comprises a substituted phenol compound wherein $R_1$ is an optionally substituted imidazolyl. In another embodiment, a substituted phenol compound of the above formula comprises a compound wherein one or more of $R_2$, $R_3$ or $R_5$ can be a hydroxyl or a hydrogen. In another embodiment, a substituted phenol compound of the above formula comprises a compound wherein $R^1$ is imidazol-2-yl, imidazol-4-yl or imidazol-5-yl each of which is substituted with one or two $C_1$-$C_4$ alkyl substituents. In addition, another substituted phenol compound may comprise a formula wherein $R^1$ is an N—$C_{1-4}$ alkyl imidazol-2-yl, N—$C_{1-4}$ alkyl imidazol-4-yl,1 or N—$C_{1-4}$ alkyl imidazol-5-yl, each of which is substituted with one or two $C_1$-$C_4$ alkyl substituents In this manner, the compound of this formula comprises a compound with a positively charged moiety,

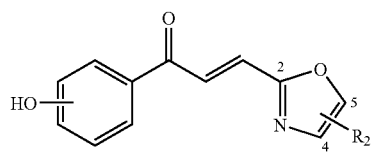

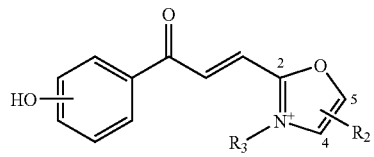

In another embodiment, a substituted phenol compound of the above formula comprises a substituted phenol compound wherein $R_1$ is an optionally substituted oxazolyl. In another embodiment, a substituted phenol compound of the above formula comprises a compound wherein $R^1$ is oxazol-2-yl, oxazol-4-yl or oxazol-5-yl each of which is substituted with one or two $C_1$-$C_4$ alkyl substituents. In addition, another substituted phenol compound may comprise a formula wherein $R^1$ is an N—$C_{1-4}$ alkyl oxazol-2-yl, N—$C_{1-4}$ alkyl oxazol-4-yl,1 or N—$C_{1-4}$ alkyl oxazol-5-yl, each of which is substituted with one or two $C_1$-$C_4$ alkyl substituents thus conferring a positive charge to the molecule.

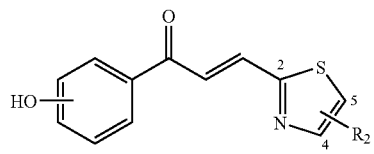

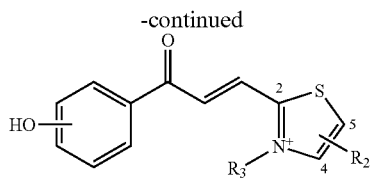

In another embodiment, a substituted phenol compound of the above formula comprises a substituted phenol compound wherein $R_1$ is an optionally substituted thiazolyl. In another embodiment, a substituted phenol compound of the above formula comprises a compound wherein $R^1$ is thiazol-2-yl, thiazol-4-yl or thiazol-5-yl each of which is substituted with one or two $C_1$-$C_4$ alkyl substituents. In addition, another substituted phenol compound may comprise a formula wherein $R^1$ is an N—$C_{1-4}$ alkyl thiazol-2-yl, N—$C_{1-4}$ alkyl thiazol-4-yl,l or N—$C_{1-4}$ alkyl thiazol-5-yl, each of which is substituted with one or two $C_1$-$C_4$ alkyl substituents.

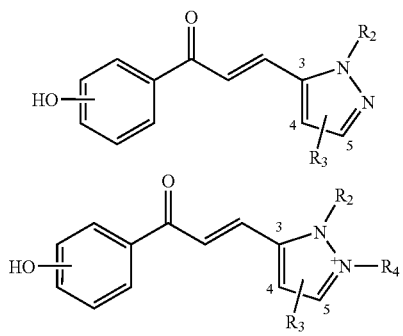

In another embodiment, a substituted phenol compound of the above formula comprises a substituted phenol compound wherein $R_1$ is an optionally substituted pyrazolyl. In another embodiment, a substituted phenol compound of the above formula comprises a compound wherein $R^1$ is pyrazol-2-yl, pyrazol-4-yl or pyrazol-5-yl each of which is substituted with one or two $C_1$-$C_4$ alkyl substituents. In addition, another substituted phenol compound may comprise a formula wherein $R^1$ is an N—$C_{1-4}$ alkyl pyrazol-2-yl, N—$C_{1-4}$ alkyl pyrazol-4-yl,l or N—$C_{1-4}$ alkyl pyrazol-5-yl, each of which is substituted with one or two $C_1$-$C_4$ alkyl substituents.

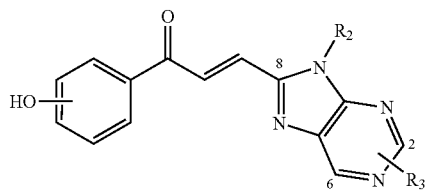

In another embodiment, a substituted phenol compound of the above formula comprises a substituted phenol compound wherein $R_1$ is an optionally substituted purinyl. In another embodiment, a substituted phenol compound of the above formula comprises a compound wherein $R^1$ is purin-2-yl, purin-6-yl or purin-8-yl each of which is substituted with one or two $C_1$-$C_4$ alkyl substituents.

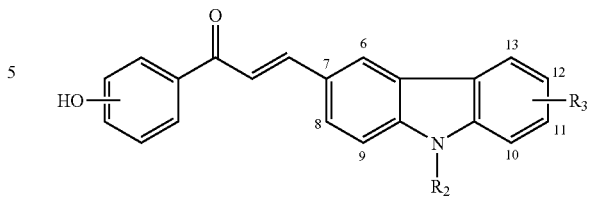

In another embodiment, a substituted phenol compound of the above formula comprises a substituted phenol compound wherein $R_1$ is an optionally substituted carbazolyl. In another embodiment, a substituted phenol compound of the above formula comprises a compound wherein $R^1$ is carbazol-6-yl, carbazol-7-yl, carbazol-8-yl, carbazol-9-yl, carbazol-10-yl, carbazol-11-yl, carbazol-12-yl or carbazol-13-yl each of which is substituted with one or two $C_1$-$C_4$ alkyl substituents. Other compounds that pertain to the embodiments include naphthoquinones, coumarins quinoline thioflavones, thioflavins, glucocorticiods, steroid, naturally occurring alkaloids also MMP (matrix metalloproteinase) inhibitors and xenobiotics (i.e. pesticides) are included.

Glucocorticoids are adrenocortical steroids, both naturally occurring and synthetic, which are readily absorbed from the gastrointestinal tract. Dexamethasone, a synthetic adrenocortical steroid and is stable in air. The molecular weight is 392.47. It is designated chemically as 9-fluoro-11 b,17,21-trihydroxy-16a-methylpregna-1,4-diene-3,20-dione. The empirical formula is $C_{22}H_{29}FO_5$.

Many of the above named chemicals are naturally occurring, but synthetic compounds are also encompassed. The chemical may be modified to include any of a variety of functional groups, such as hydroxyl and/or ether groups. Preferred chemicals such as flavones include one or more hydroxyl groups, such as the trihydroxyflavone apigenin, the tetrahydroxyflavone kaempferol and the pentahydroxyflavone quercetin. Preferred isoflavones include one or more hydroxyl groups, such as trihydroxyisoflavone genistein and methoxy containing biochanin A.

BRIEF DESCRIPTION OF THE DRAWINGS

FIG. 16. represents the effects of Rutin and Dexamethasone on the extracellular concentration of GSH

FIGS. 21A and 21B represents Flow cytometry analysis of HL-60 cells 21A, after one anti-cancer treatment and 21B, after a different anti-cancer treatment.

Figure 1:
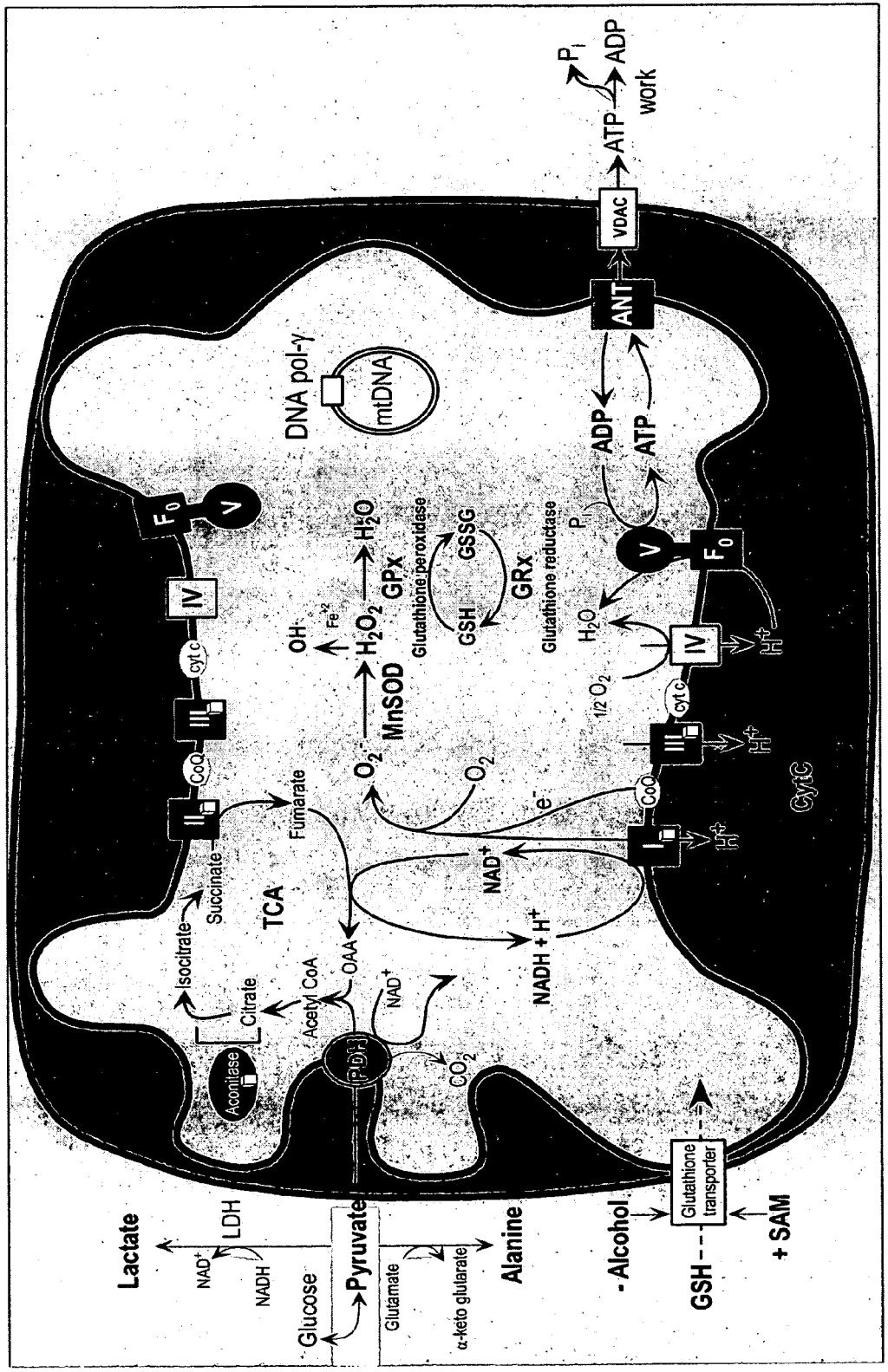
FIG. 1 illustrates cellular synthesis, metabolism and transport of glutathione (GSH) into the mitochondria.

Table 1 represents a list of amino acids and codon usage.

Table 2 illustrates proposed apical lung GSH and other thiol-containing compound transporters.

Table 3 represents chemical compounds and their effects on extracellular GSH transport.

Table 4 represents an example of depletion of intracellular GSH levels and cytotoxicity induced in human tumor cells.

Table 5 represents an example of intracellular GSH levels in cultured cancer cells after treatment.

DETAILED DESCRIPTION

In the following description, several specific details are presented such as examples of specific methods, components, and processes in order to provide a thorough understanding of various embodiments. It will be obvious to one skilled in the art that these specific details need not be employed to practice the various embodiments. In other cases, some well-known components or methods will not be described in detail in order to alleviate unnecessary obscuring of various embodiments presented forthwith.

Compositions and methods of use to treat thiol-containing compound transport deficiencies are described.

Cystic Fibrosis (CF) is a devastating genetic disorder that results in chronic infection of the lung with a deteriorating cycle of inflammation and injury that ultimately destroys the lung. CF is caused by mutations in the protein called CFTR, cystic fibrosis transmembrane conductance regulator, an ABC-transporter-like protein found in the plasma membrane of animal cells (Rommens, J. M. et al. (1989) Science 245: 1059-1065; Riordan, J. R. et al. (1989) Science 245:1066-1073; Kerem, B-S. et al. (1989) Science 245:1073-1080). The CFTR gene is localized within a putative ATP binding/ATP hydrolysis domain. The deletion of phenylalanine at position 508 (.DELTA.F508-CFTR) represents approximately 70% of patients with cystic fibrosis. CFTR is an integral membrane protein primarily expressed in the epithelia of the lung, pancreas, sweat glands, and vas deferens. Recently, other than transport of chloride ions, this transporter also carries glutathione to the cell exterior. In the lung the epithelial cells maintain the epithelial lining fluid (ELF) that coats the airways and is a critical component of the lung host defense that helps the mucociliary clearance pathway. This pathway is critical in providing a sterile environment in the lung and is severely compromised in CF patients.

Recent studies suggest that the CFTR protein modulates ELF GSH and when defective creates an imbalance of glutathione-mediated processes in the lung. CF patients bearing this deltaF508 mutation frequently experience chronic lung infections, particularly by *Pseudomonas aeruginosa*, and have a limited life span. Attempts to remedy the mutated CFTR protein have been unsuccessful. The deltaF508 mutation destroys the proteins ability to function as a transporter. The embodiments of this invention identify therapies that address alternate treatments for CF affected individuals and ELF replenishment of thiol-containing compound levels including the stimulation of other unaffected transporters, as well as therapies for other thiol-compound excretion deficient afflicted patients.

Other complications may arise in CF patients such as they suffer from diminished pancreatic function that leads to inadequate breakdown and absorption of fat-soluble nutrients. Poor absorption may result in deficiencies of the fat-soluble antioxidant vitamins for example α-tocopherol (vitamin E) and β-carotene (precurser of vit. A), as well as other components of the oxidant scavenging system such as ferritin and selenium.

Other than CF patients, other thiol-containing compound deficient conditions exist. An immune-compromised or intensive care unit patient has below normal cellular levels of GSH. It is believed that a patient who has decreased GSH levels is more susceptible to many disease states. It is therefore important to ensure that extracellular and intracellular GSH levels are maintained at near normal levels, or increased to meet those levels.

A number of such patients having reduced glutathione levels also have impaired or compromised gut functions. Examples of such patients include those suffering from: AIDS; Crohn's disease; chronic inflammatory bowel disease (IBD); short bowel syndrome; and inflammatory bowel reaction to radiation therapy. Providing an intact protein, such as casein, does not provide a sufficiently bioavailable source of GSH to the patient since the gut function of these patients is compromised. Thus, supplying adequate amounts of thiol-containing compounds to these distressed areas is critical in patient recovery.

The status of reduced glutathione (L-.gamma.-glutamyl-L-cysteinyl-glycine, GSH), in ELF of adults with CF has been evaluated. In normal individuals, respiratory ELF has high levels of GSH, typically 200-fold greater than plasma (Cantin, A. M. et al. (1987) J. Appl. Physiol. 63:152-157). There is a chronic influx of oxidants on the respiratory epithelium, and with the knowledge that oxidants released from inflammatory cells can derange the respiratory epithelial structure and function and interfere with host defense GSH can scavenge all major oxidants produced by inflammatory cells (Meister, A. (1988) J. Biol. Chem. 263:17205-17208; Buhl, R. et al. (1990) Proc. Natl. Acad. Sci. USA. 87:4063-4067; Heffner, J. E., and J. E. Repine (1989) Am. Rev. Respir. Dis. 140:531-554), and its function as an antioxidant on the respiratory epithelial surface is enhanced by the presence of glutathione peroxidase and glutathione reductase in respiratory ELF (Meister, A. (1988) J. Biol. Chem. 263:17205-17208; Cantin, A. M. et al. (1990) J. Clin. Invest. 86:962-971; Davis, W. B., and E. R. Pacht (1991) In The Lung: Scientific Foundations. R. G. Crystal and J. B. West, editors. Raven Press, New York. 1821-1828). GSH is believed to be the primary intracellular antioxidant for higher organisms. It is a mono-thiol compound. When oxidized, it forms a dimer (GSSG), which is likely recycled into cells having glutathione reductase (Tanuguchi, N., et al. (1989., Glutathione Centennial, Academic Press, New York).

GSH is synthesized from constituent amino acids by the sequential action of γ-glutamylcysteine synthetase (γ-GCS) and GSH synthetase (GS) where γ-GCS is rate limiting. GSH plays a major role in cellular defenses against oxidative stress and reactive electrophiles. GSH also participates in the reductive detoxification of hydrogen peroxide and lipid peroxides. Each of these reactions leads directly or indirectly to the formation of glutathione disulfide (GSSG), a species that is reduced intracellularly to GSH by glutathione reductase (GR) in a NADPH-dependent reaction. GR normally maintains the total glutathione pool in a predominately-reduced state; thus, redox cycling between GSSG and GSH does not usually have a major influence on cellular GSH levels. Extracellular degradation of GSH and GSSG is carried out rapidly by membrane bound γ-glutamyl-transpeptidase (GGT) and cysteinyl-glycine dipeptidase (DP). In the lung, GGT is primarily located on the airspace epithelial surface and facilitates γ-glutamyl absorption from ELF GSH. Although GSH reacts spontaneously with some electrophiles, most of these reactions require catalysis by a family of enzymes known as GSH S-transferases (GST). The initial products are chemically stable sulfides of GSH, but upon further metabolism form S-substituted L-cysteines that are acetylated to form mercapturic acids and readily excreted in the urine. Cellular synthesis, metabolism and transport of GSH are summarized in FIG. 14.

Important Roles of GSH

Bronchoalveolar lavage (BAL) leukocytes from CF patients have exaggerated cytokine release and oxidant generation responses to stimuli and CF patients aerosolized with GSH had suppressed oxidant generation from stimulated BAL leukocytes.

Many CF patients are chronically infected with *Pseudomonas aeruginosa*, which releases redox active pigments that generate oxidants, inhibit anti-proteases and induce neutrophil apoptosis. GSH is a major water-soluble anti-oxidant in the ELF that protects anti-proteases from inactivation by oxidants and prevents excessive tissue destruction from neutrophil derived proteases like neutrophil elastase. This scenario creates an imbalance between antiproteases and proteases in the lung leading to increased tissue destruction.

Prevention of Oxidative Stress in the Mitochondria by Superoxide Dismutase and Glutathione In FIG. 1 during oxidative phosphorylation, the mitochondria generates superoxide anion ($O_2^-$) and hydrogen peroxide ($H_2O_2$) through the respiratory chain. Superoxide formation arises from two sites along the respiratory chain: the NADH dehyrgrogenase (I) and ubiquinone Q-cytochrome b complex (III). Normally, 2-4% of the electron flux through the respiratory chain reduces oxygen to $O_2^-$ instead of water. Once formed, $O_2^-$ is rapidly reduced to $H_2O_2$ by manganese superoxide dismutase (MnSOD). $H_2O_2$ may react with reduced iron ($Fe^{+2}$) to form the highly toxic hydroxyl radical (OH.), or detoxified to $H_2O$ by the action of glutathione peroxidase (GPx). GPx consumes reduced glutathione (GSH) in this catalysis to form oxidized glutathione (GSSG). GSH is regenerated from the GSSG by glutathione reductase (GRx). GSH synthesis, however, occurs in the cytoplasm and requires transport into the mitochondria. Little is currently known about the transporter(s) responsible for regulating mitochondrial GSH.

The extracellular reducing environment is critical for proper immune function such as antigen presentation and subsequent T cell proliferation. GSH can affect the nature and level of antigen presentation in APCs by altering the protein disulfide bonds required for proteolytic digestion of the antigen. GSH can also regulate cytokine release, such as IL-4, from lymphocytes and directly suppress inflammatory responses. GSH is a potent mucolytic agent due to its ability to cleave disulfide bonds. The thickened mucus can lead to airway obstruction and decreased bacterial clearance.

GSH may be an important reactant with nitric oxide and may regulate nitric oxide's bioavailability and influence whether nitric oxide acts as an antioxidant or prooxidant. GSH is also a precursor of S-nitrosoglutathione (another important monothiol) that is an endogenous bronchodilator and found to be deficient in lung of CF patients.

The normal healthy adult human liver synthesizes 8-10 grams of GSH daily. Normally, there is an appreciable flow of GSH from liver into plasma. The intracellular level of GSH in mammalian cells is in the range of 0.5-10 millimolar, while micromolar concentrations are typically found in blood plasma. Intracellular glutathione is normally over 90% found in a reduced form (GSH). The major organs involved in the inter-organ transport of GSH are the liver and the kidney, which is the primary organ for clearance of circulating GSH. It has been estimated to account for 50-67% of net plasma GSH turnover. Several investigators have found that during a single pass through the kidney, 80% or more of the plasma GSH is extracted, greatly exceeding the amount that could be accounted for by glomerular filtration. While the filtered GSH is degraded stepwise by the action of the brush-border enzymes γ-glutamyltransferase and cysteinylglycine dipeptidase, the remainder of the GSH appears to be transported via an unrelated, Na+-dependent system present in basal-lateral membranes.

Glutathione exists in plasma in four forms: reduced glutathione (GSH), oxidized glutathione (GSSG), mixed disulfide with cysteine (CySSG) and protein bound through a sulfhydryl linkage (GSSPr). The distribution of glutathione equivalents is significantly different than that of cyst(e)ine, and when either GSH or cysteine is added at physiological concentration, a rapid redistribution occurs. In erythrocytes, GSH has been implicated in reactions that maintain the native structure of hemoglobin and of enzymes and membrane proteins. GSH is present in erythrocytes at levels 1000 times greater than in plasma. It functions as the major small molecule antioxidant defense against reactive oxygen species.

The importance of thiols and especially of GSH to lymphocyte function is known. Adequate concentrations of GSH are required for mixed lymphocyte reactions, T-cell proliferation, T- and B-cell differentiation, cytotoxic T-cell activity, and natural killer cell activity. Adequate GSH levels have been shown to be necessary for microtubule polymerization in neutrophils. Intraperitoneally administered GSH augments the activation of cytotoxic T-lymphocytes in mice, and dietary GSH was found to improve the splenic status of GSH in aging mice, and to enhance T-cell-mediated immune responses.

Decreasing GSH by 10-40% can completely inhibit T-cell activation in vitro. Depletion of intracellular GSH has been shown to inhibit the mitogenically-induced nuclear size transformation in the early phase of the response. Cysteine and GSH depletion also affects the function of activated T-cells, such as cycling T-cell clones and activated cytotoxic T-lymphocyte precursor cells in the late phase of the allogenic mixed lymphocyte culture. DNA synthesis and protein synthesis in IL-2 dependent T-cell clones, as well as the continued growth of preactivated CTL precursor cells and/or their functional differentiation into cytotoxic effector cells are strongly sensitive to GSH depletion.

The nucleoplilic sulfur atom of the cysteine moiety of GSH serves as a mechanism to protect cells from harmful effects induced by toxic electrophiles. The concept that glutathione S-conjugate biosynthesis is an important mechanism of drug and chemical detoxification is well established. GSH conjugation of a substrate generally requires both GSH and glutathione-S-transferase activity. The existence of multiple glutathione-S-transferases with specific, but also overlapping, substrate specificities enables the enzyme system to handle a wide range of compounds.

Because of its known role in renal detoxification and its low toxicity, GSH has been explored as an adjunct therapy for patients undergoing cancer chemotherapy with nephrotoxic agents such as cisplatin, in order to reduce systemic toxicity. Other studies have shown that i.v. GSH coadministration with cisplatin and/or cyclophosphamide combination therapy, reduces associated nephrotoxicity, while not unduly interfering with the desired cytotoxic effect of these drugs. GSH functions in many important biological phenomena, including the synthesis of proteins and DNA, transport, enzyme activity, metabolism, and protection of cells from free-radical mediated damage. GSH is one of the primary cellular antioxidants responsible for maintaining the proper oxidation state within the body. GSH is synthesized by most cells, and is also supplied in the diet.

Biochemical Consequences of Oxidative Stress

Figure 2:
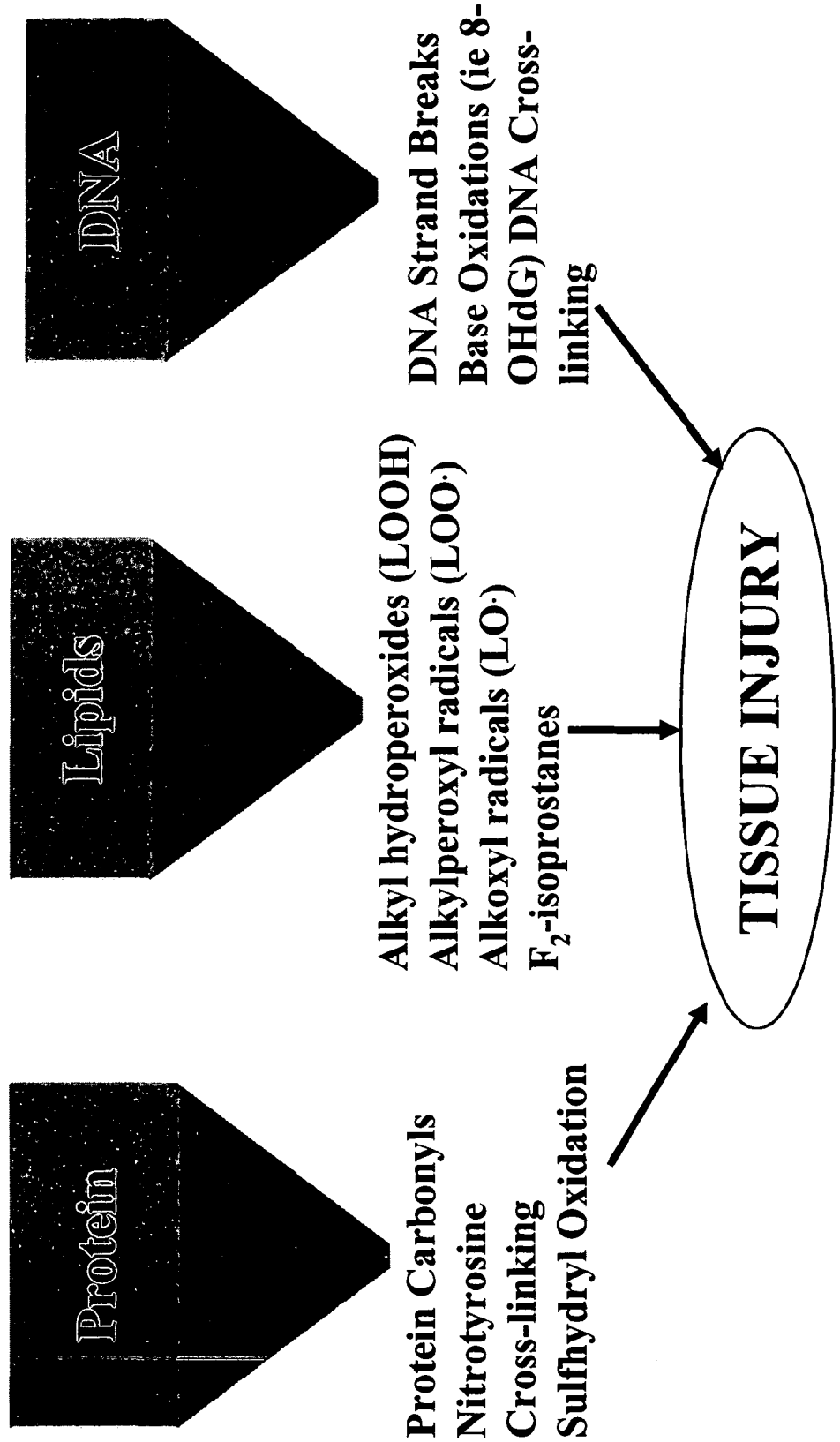
FIG. 2 represents a schematic example of possible biochemical consequences of oxidative stress.

FIG. 2 illustrates a schematic flow of reactive oxygen species (ROS; e.g., superoxide, hydrogen peroxide, hydroxyl radical) and reactive nitrogen species (RNS; e.g., nitric oxide, nitrogen dioxide, peroxynitrite) on macromolecules. These species may oxidize or nitrate proteins, lipids and DNA. Protein oxidations may result in the loss of function (e.g., sulfhydryl and tyrosine oxidation) and protein cross-linking. Lipid oxidation generates hydroperoxides and other oxidants (e.g., alkoxyl and alkylperoxyl radicals) that can propagate the oxidative stress. DNA oxidations cause strand breaks, base modifications and strand cross-linking. Ultimately, these biochemical alterations may lead to tissue injury.

In certain embodiments, the transport of thiol-containing compounds for example GSH may be increased in order to replenish inadequate supplies. In other embodiments, the intracellular distribution of thiol-containing compounds may be targeted in order to redistribute GSH to such cell compartments for example the mitochondria. Because of the importance of glutathione in preventing this cellular oxidation, glutathione is continuously supplied to the tissues. However, under certain conditions, the normal, physiologic supplies of glutathione are insufficient, distribution inadequate or local oxidative demands too high to prevent cellular oxidation. Under certain conditions, the production of and demand for glutathione are mismatched, leading to insufficient levels. In other situations, certain tissues or biological processes consume glutathione so that the intracellular levels are inadequate. In either case, by increasing the levels of glutathione, increased amounts may be directed into tissues.

Direct GSH Applications

It is believed that beneficial physiological effects of orally administered glutathione are difficult or impossible to achieve, or the efficiency is so low as to make supplementation by this route unproductive. The protocols for oral administration of glutathione were not optimized and therefore the bioavailability of the glutathione was unassured and variable. All prior pharmaceutical attempts by others to safely, effectively and predictably raise intracellular GSH through oral therapy with GSH have met with very little success. It was also believed that orally administered glutathione would tend to be degraded in the stomach, and that it is particularly degraded under alkaline conditions by desulfurases and peptidases present in the duodenum.

Because of the poor or variable results obtained with GSH, orally absorbed pro-drugs and precursors have also been used. A known pharmacological regimen provides intravenous glutathione in combination with another agent, such as cis-platinum (a free radical associated metal drug), doxorubicin, or daunorubicin (free radical associated drugs which interact with nucleic acid metabolism), which produced toxic side effects related to free radical reactions. The combination of the components has revealed limited success.

Although the parenteral infusion of cysteine precursors as well as glutathione esters is believed to be an effective way to increase or maintain a sufficient level of intracellular glutathione, it would of course be desirable if the intracellular glutathione level could be maintained or increased through an enteral diet. One of the difficulties in increasing through an enternal regimen intracellular glutathione levels is that it is not typically possible merely to provide an enteral amino acid solution rich in cysteine. Cysteine typically will crystallize out as cystine in solution, e.g., an amino acid solution. Cystine is not readily biologically available to cells. Therefore, cysteine is not biologically available as a pharmaceutical.

Other proposed administration of glutathione is using aerosol administration through the nasal passageway. This route also proved fruitless since the glutathione cannot penetrate the mucosal layer very efficiently and it is often oxidized prior to reaching the intended area (i.e. namely the ELF of cystic fibrosis patients)(Buhl, R. PNAS 87:4063, 1990 and Roum J. of Physiol. 87:438 1999).

In one embodiment, the transport of existing GSH out of cells or tissue will be increased via transporters. In other embodiments, "GSH-like" mono-thiol compound secretion out of cells or tissue will be increased. In other embodiments, the intracellular distribution of thiol-containing compounds may be altered in order to prevent or treat a condition. In one embodiment, one or more compounds may be used to restore thiol-containing compounds extracellularly. In other embodiments, one or more compounds may be used to restore GSH levels extracellularly. In one embodiment, one or more compounds may be used to restore thiol-containing compounds intracellularly. In other embodiments, one or more compounds may be used to restore GSH levels intracellularly.

In other embodiments, other mono-thiol containing compounds that can be exported are cysteinyl leukotriene, LTC4 and any other mono-thiol containing compounds capable of excretion by one or more ABC transporters described below.

Thioredoxin

Thioredoxin (TXR) is a potent protein disulfide reductase found in most organisms that participates in many thiol-dependent cellular reductive processes. Along with glutathione, thioredoxin is also a major small molecular weight thiol-containing compound synthesized de novo in mammalian cells. In addition to its ability to effect the reduction of cellular proteins, thioredoxin can act directly as an antioxidant (e.g it scavenges free radicals) or can increase the oxidative stress in a cell by autooxidizing (e.g. generating superoxide radicals through autoxidation). Thioredoxin can also directly induce the production of MnSOD (manganese superoxide dismutase, sod2).

Investigators have reported the use of thioredoxin to treat several conditions. One invention taught that "thioredoxin compounds" can be topically applied to the eye to reduce disulfide bonds of oxidized lens proteins involved in cataract formation, thus preventing or reducing a cataractous condition (U.S. Pat. No. 4,771,036). Other investigators have reported the intravenous injection of thioredoxin to treat post-ischemia tissue injury in rats or dogs (Fukuse, et al., pp. 387-391, 1995, Thorax, Vol. 50; Yagi et al., pp. 913-921, 1994, J. Thorac. Cardiovasc. Surg., Vol. 108). These studies measured only the physiological effects of thioredoxin on ischemia and suggested that thioredoxin had limited success and was acting as an antioxidant (scavenger of free radicals). In these examples, thioredoxin was intravenously administered in these studies, and was only present for a very short time at the site of damage, if at all. It is further unknown whether thioredoxin even went to the specific site of damage, the lung. Such reports do not disclose or suggest a method or composition to increase a thiol-containing compound transporter(s) having a distinct ability to actively pump the existing thiol-containing compounds to the site of interest (i.e. the ELF of the lung).

Investigators have found thioredoxin in most organisms and it participates in many thiol-dependent cellular reductive processes. In humans, thioredoxin is also referred to as adult T cell leukemia-derived factor (ADF). Intracellularly, most of this ubiquitous low molecular weight (11,700) protein remains reduced. Reduced or oxidized thioredoxin can enter intact cells. It has two vicinal cysteine residues at the active site that in the oxidized protein forms a disulfide-bridge located in a protrusion from the protein's three-dimensional structure. The flavoprotein thioredoxin reductase catalyzes the NADPH-dependent reduction of this disulfide. Small increases in the presence of thioredoxin can cause profound changes in sulfhydryl-disulfide redox status in proteins. Thus, thioredoxin is extremely potent as a reducing agent. Extremely low concentrations of thioredoxin are effective in reducing disulfides in insulin, fibrinogen, human chorionic gonadotropin, blood coagulation factors, nitric oxide synthase, ribonucleotide reductase, glucocorticoid receptors and other proteins. The rate of reduction of insulin disulfide by thioredoxin has been found to be 10,000 times higher than that by DTT (dithiothreitol). Thioredoxin has also been found to be a greater reducer than GSH as well. Thus, reduced thioredoxin is an extremely potent protein disulfide reductase. A preferred embodiment of this invention comprises the increase of thiol-containing compound transporters to increase the export of thioredoxin. In other embodiments, these transporters are used to increase the export of thioredoxin into the ELF of the lung epithelium by apical exportation.

Trx together with thioredoxin reductase (TrxR) and NADPH comprise the thioredoxin system. Thioredoxins have a redox-active disulfide/dithiol and are reduced by selenium-dependent thioredoxin reductases with a Gly-Cys-Sec-Gly active site. Thioredoxins in the cytosol, mitochondria or extracellularly are the cells major disulfide reductases required for the control of redox potential and signalling by thiol redox control.

Glutaredoxin

Glutaredoxin (Grx) catalyzes disulfide oxidoreductions involving glutathione (GSH) and the glutaredoxin system comprises Grx, GSH, glutathione reductase and NADPH. Glutaredoxins which have a classical Cys-Pro-Tyr-Cys active site and a binding site for GSH are required for GSH to operate in thiol-dependent reductions like the synthesis of deoxyribonucleotides by ribonucleotide reductase. Glutaredoxins play a specific role in redox regulation via reverible glutathionylation of proteins where both the synthesis and degradation of the mixed disulfide with glutathione is catalysed by multiple dithiol or monothiol glutaredoxins (Arner, E S J and Holmgren, A. (2000), Eur. J. Biochem., 267,6102-6109; Zhao, R., Masayasu, H. and Holmgren, A. (2002) Proc. Natl. Acad. Sci. USA, 99, 8579-8584; Lundberg, M. et al. (2002) J. Biol. Chem. 276, 26269-26275.). Glutaredoxin is characterized by a dithol/disulphide redox-active site. Human glutaredoxin, unlike *E. coli* glutaredoxin, has an additional pair of cysteine residues that may play a regulatory role in its activity. One embodiment includes using one or more compounds to increase the extracellular transport of glutaredoxin.

ABC Superfamily

The ABC superfamily transport proteins to a variety of molecules, ranging from ions to proteins, across cell membranes. (For a review see C. F. Higgins, Ann. Rev. Cell Biol. 8, 67 (1992) and Klein, I. Biophys. Biochem. Abstracts 1461: 237 (1999)). There are approximately 50 known ABC transporters in the human. As mentioned earlier, 13 genetic diseases associated with defects in 14 of these transporters exist.

Mechanisms in Multi-Drug Resistance: ABC-transporters and Detoxification Enzymes The cellular components responsible for the phenomenon of multi-drug resistance (MDR) in the structural context of for example, hepatocytes include intrinsic transmembrane proteins, generically called drug efflux pumps, and the enzymes responsible for detoxification and biotransformation of xenobiotics (i.e. pesticides). The transporters, which have been called P-glycoprotein (MDR), multidrug resistance related protein (MRP) and GS-X pump and which are believed to be involved in the primary active pumping of xenobiotics from the cells, are now known as the ATP-binding cassette (ABC) transporters. The major drug efflux pumps are in the superfamily of ABC transporters. Of these ABC-ATPases, the major subfamilies are the MDR/TAPs and MRPs (multi-drug resistance related proteins). The natural substrates are indicated for the drug efflux pumps in the references indicated (Shabbits, J. A., et al., Molecular and pharmacological strategies to overcome Multidrug resistance. Expert Rev. Anticancer Ther., 1, 585-594 (2001); Di, P. A., et al., Modulation by flavonoids of cell multidrug resistance mediated by P-glycoprotein and related ABC transporters. Cell. Mol. Life Sci., 59, 307-322 (2002); Meier, P. J., and Stiger, B., Bile salt transporters. Annu. Rev. Physiol., 64, 635-661 (2002)).

One ABC transporter family example, the P-glycoproteins (P-gp), transport chemotherapeutic drugs. This family includes the CFTR, which controls chloride ion fluxes, as well as insect proteins that mediate resistance to anti-malarial drugs. P-glycoprotein is believed to confer resistance to multiple anticancer drugs by acting as an energy dependent efflux pump that limits the intracellular accumulation of a wide range of cytotoxic agents and other xenobiotics. In addition, other compounds that are excluded from mammalian cells by P-glycoprotein are frequently natural product-type drugs such as thiol-containing compounds but also other large heterocyclic molecules are also "substrates" for this efflux pump. In one embodiment, a compound may be used to modulate the extracellular transport of thiol-containing compounds by increasing the activity of CFTR.

Domain Organization of Multi-Drug Related Protein (MRP1)

Figure 13:
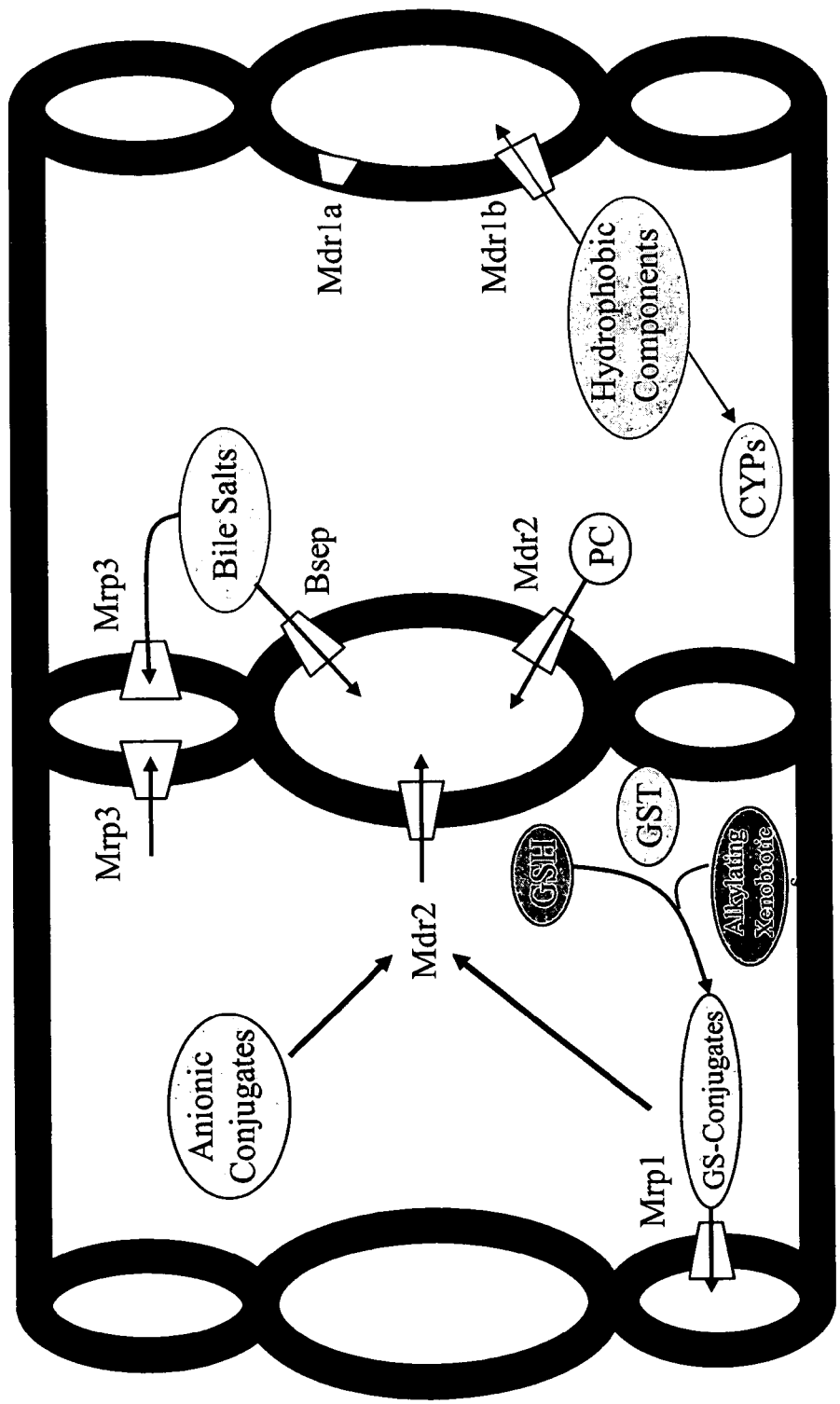
FIG. 13 illustrates a schematic of a hepatocyte and several transporters for detoxification used in multi-drug resistance.

MRP1 is a representative of the second major subfamily, MRP, of multidrug ABC transporters. MRPs have an extra TMD (transmembrane domain) and have the general form of $TMD_0(ABC-TMD)_2$. FIG. 13 shows the transporter as an intrinsic membrane protein (Kruh, G. D., et al. MRP subfamily transporters and resistance to anticancer agents. J. Bioenerg. Biomembr.33, 493-501 (2001); Borst, P., et al. A family of drug transporters: the multidrug resistance-associated proteins. J. Natl. Cancer Inst., 92, 1295-1302 (2002); Rosenberg, M. F., et al. The structure of the multidrug resistance protein 1 (MRP1/ABCC1), crystallization and single-particle analysis. J. Biol. Chem., 276, 16076-16082 (2001)).

Also, MRP2 (multi-drug resistance protein) is known to transport GSSG and glutathione conjugates. MRP1 is ubiquitously expressed in normal tissues and is a primary active transporter of GSH, glucuronate and sulfate conjugated and unconjugated organic anions of toxicological relevance (i.e. herbicides, mycotoxins, heavy metals, natural products). The most studied of these proteins is the basolaterally expressed MRP-1 that co-transports GSH with natural product toxins such as aflatoxin and vincristine. In the liver, MRP-2 functions as a low-affinity export pump for release of GSH across apical domains. Direct support indicates that the CFTR protein is involved in only half of the GSH transport into the pulmonary ELF. However, the transporter(s) for the other half of the glutathione are currently not known. The embodiments target other ABC cassette protein super family members that contribute to the apical transport of glutathione in tissues (i.e. the lung) and these transporters could be manipulated to endogenously restore glutathione to the lung ELF (Table 2).

Many of these ABC transporters function on the apical membrane of epithelial cells (i.e. P-gp and MRP2 etc.) thus enabling the export of several components. The expression of these transporters appears to be tissue specific. For example, MRP2 is found almost exclusively in apical membranes of polarized cells (i.e. kidney, liver, lungs and the intestine). MRP1 is located in the basolateral side of epithelial cells (Laouari, D. et. al. "Two Apical drug transporters, P-gp and MRP2, are differently altered in chronic renal failure" AJP—Renal Physiology, 280 (4):F636-F645, April 2001). MRP1 and related transporters MRP2 and MRP3 have overlapping substrate specificities but there tissue distribution varies. Thus, several embodiments are directed at the increase in thiol-containing compounds excretion via transporters localized to a specific tissue. In other embodiments, these thiol-containing compound transporters include increasing thiol-containing compound excretion via transporters localized in the lung. Additional embodiments include thiol-containing compound transporters to increase thiol-containing compound excretion via transporters localized in the lung epithelia. In still other embodiments, these transporters are transporters found in the pancreas, gastointestinal tract, sweat glands, the vas deferens, and kidney.

P-glycoprotein has been identified in a variety of tumor types. This information spurred on the search for compounds that are capable of blocking its function and consequently, reversing resistance to the anti-cancer agents. A large number of agents called chemosensitizers or reversing agents have been identified. Chemosensitizers that can reverse P-glycoprotein-mediated multidrug resistance include verapamil and cyclosporin A. These agents interfere with the ability of the transport system to excrete the chemical agent.

One embodiment includes a method to identify compounds that increase the excretion of thiol-containing compounds that normally "ride along" with the chemotherapy agent as the drug is excreted from the cell. The mode of excretion is often associated with the same ABC transporters that excrete chemotherapy drugs in resistant tumor cells. Other embodiments detail the use of some of these chemotherapy drugs to increase the excretion of the thiol-containing compounds by affecting the transporters. Some of these embodiments detail the excretion of mono-thiol compounds (i.e. glutathione, cysteine etc.). Other embodiments detail the secretion of di-, tri- and multi-thiol-containing compounds (i.e. thioredoxin, gluteradoxin) using some of the same chemotherapy drugs.

In other embodiments of this invention, inhibitors of compounds that negatively affect ABC transporter activity, expression and/or synthesis will be used. In other embodiments, inhibitors of various forms of p53 that are known to suppress SP1-DNA binding activity will be used to increase the activity of the transporters of the thiol-containing compounds. SP1-DNA is thought to stimulate the expression of the ABC transporters. (Iida, T. et. al. Cancer Gene Therapy 2001 October; 8(10):803-814.)

Several agents are currently known to modulate the activity and or expression of ABC transporters and the ability of these transporters to excrete chemotherapy drugs. Some embodiments of this invention include the use of agents to increase the presence or the activity of the transporters to deliver thiol-containing compounds "along with" chemotherapy drugs. One embodiment relates to the use of dexamethasone, shown to increase the level of glutathione in the lung ELF. see FIG. 17. The increase in the P-gp by dexamethasone is rapid, peaking at Day1-3. (DeMeule, M. et. al. FEBS Letters 442 (1999) 208-214). Using a single dose, cisplatin (cis-dichlorodiammne platinum (II) induces P-gp 200-300× in the renal basement membrane, liver and intestine (DeMeule, M. Am. J. Physiol. 227 (Renal Physiol. 46): F832-F840, 1999). Other embodiments include the use of cis-platin to induce the presence of ABC-transporters for increasing the excretion of thiol-containing compounds. Additional embodiments include the use of cis-platin to increase the presence of specific transporter such as P-gp transporters for increasing the excretion of thiol-containing compounds. Other embodiments include the use of vinblastine to induce the expression of MRP2; daunorubicin to induce MRP1 expression and sulfinpyrazone at low doses to induce the co-transport of GSH and sulfinpyrazone in a "positive cooperativity" mode.

Sulfasalazine is a well-known drug that is used to treat rheumatoid arthritis and inflammatory bowel disease. However, the mechanism of action of sulfasalazine in these diseases is poorly understood. It has been proposed that sulfasalazine possesses anti-inflammatory properties including the inhibition of NFkB (Pittet J F, Lu L N, Morris D G, Modelska K, Welch W J, Carey H V, Roux J, and Matthay M A. Reactive nitrogen species inhibit alveolar epithelial fluid transport after hemorrhagic shock in rats. J. Immunol. 166: 6301-6310, 2001), lymphocyte x(c)-cystine transporter (Gout P W, Buckley A R, Simms C R, and Bruchovsky N. Sulfasalazine, a potent suppressor of lymphoma growth by inhibition of the x(c)-cystine transporter: a new action for an old drug. Leukemia 15:1633-1640, 2001), and selective modulation of B cell function (Hirohata S, Ohshima N, Yanagida T, and Aramaki K. Regulation of human B cell function by sulfasalazine and its metabolites. Int Immunopharmacol 2:631-640, 2002). Another possible mechanism for the anti-inflammatory actions of sulfasalazine is it and its metabolite (p-amino salicylic acid) ability to increase glutathione efflux in epithelial cells (see table 3). In one embodiment, sulfasalazine may be used alone or in combination with one or more additional agents to increase the transport of thiol-containing compounds from one or more cells. In another embodiment, sulfasalazine may be used alone or in combination with one or more additional agents to increase the transport of thiol-containing compounds from one or more lung cells. In still another embodiment, sulfasalazine may be used alone or in combination with one or more additional agents to increase the transport of thiol-containing compounds (for example, glutathione) to the lung ELF.

Other agents known to increase the expression of multidrug resistance transporters are naturally occurring substances such as berberine, an alkaloid of the Chinese herb referred to as Goldenseal. Berberine has been shown to increase the expression of P-gp (pgp-170) in hepatoma cells of humans and mice (Lin, HL "Up-regulation of multidrug resistance transporter expression by berberine in human and murine hepatoma cells," Cancer 1999 May 1; 85(9):1937-42). Therefore, other embodiments of this invention include the use of naturally occurring substances extracted from herbs to increase the expression and/or activity of transporters of thiol-containing compounds. Further, other embodiments include the use of Goldenseal extracts to increase the expression and/or activity of transporters of thiol-containing compounds. In addition, embodiments include the use of berberine to increase the expression and/or activity of transporters of thiol-containing compounds. Exposure to microorganisms can also increase the lung expression of both CFTR and MRP-2 and this correlates with a 6-fold increase in ELF glutathione levels (see FIG. 18).

Still other agents increase the expression of MRPs and other ABC transporters namely, xenobiotics. The very chemicals that are excreted from cells to protect the cell from their exposure also induce the transporters. This has been documented in mammals as well as aquatic life (Bard et al. "Expression of P-glycoprotein and cytochrome p450 1A in intertidal fish (Anoplarchus) exposed to environmental contaminants." Aquat Toxicol. 2002) October 2; 60 (1-2): 17-32). In other embodiments, xenobiotics or xenobiotic-like compounds such as a sufficient amount of pesticides or other xenobiotics may be used to increase the expression and/or activity of transporters of thiol-containing compounds.

Other compounds that may affect the level of ABC transporters are MMPs (matrix metalloproteinases). The MMPs are members of a family of at least 20 proteolytic enzymes that contain a zinc ion at their active sites and can degrade collagen, elastins, and other components of the extracellular matrix (ECM). Cytokine activation of cells can lead to increased processing of MMPs from inactive zymogens to the active enzymes. Cytokines and their receptors can also be substrates for MMP action. Many of the membrane-bound cytokines, receptors, and adhesion molecules can be released from the cell surface by the action of a subset of metalloproteinases called convertases or adamalysins. This may be one mechanism for the down-regulation of cell surface receptors and transporters such as ABC transporters. (Nagase, H., and Woessner, J. F., Jr., Matrix metalloproteinases. J. Biol. Chem., 274, 21491-21494 (1999). Rooprai, H. K., et al., The effects of exogenous growth factors on matrix metalloproteinase secretion by human brain tumour cells. Br. J. Cancer, 82, 52-55 (2000); Stone, A. L., et al., Structure-function analysis of the ADAM family of disintegrin-like and metalloproteinase-containing proteins (review). J Protein Chem., 18, 447-465 (1999); Killar, L., et al., Adamalysins. A family of metzincins including TNF-a converting enzyme (TACE). Ann. NY Acad. Sci., 878, 442-452 (1999)).

Collagen is an intrinsic component of the extracellular matrix in the lung and is continuously being synthesized and degraded. The majority of collagen is synthesized and secreted by fibroblasts and lung alveolar macrophages secrete matrix metalloproteinases (MMPs) that degrade it. The activity of MMPs is kept in check by the release of tissue inhibitors of metalloproteinases (TIMPs). During inflammation the balance between MMPs and TIMPs is disrupted and is thought to lead to enhanced matrix destruction, cytokine inactivation, and shedding of cell surface molecules, which can lead to amplification of the inflammatory response. The redox state of the extracellular spaces in the lung is set by glutathione and regulates the balance of MMP and TIMP activities.

One embodiment includes the use of MMP inhibitors for example TIMP1, TIMP2, or TIMP3 to inhibit MMPs that may result in the increase in availability of ABC transporters.

Knockout Mice

Several mouse strains have been used to characterize the function of ABC transporters in certain systems such as Congenic C57BL/6J-CFTR$^{TM1UNC}$ The CFTR KO has an increased inflammatory response and mortality towards *Pseudomonas aeruginosa* (strain M57-15) infection. (Van Heeckeren et al. J. Clin. Invest. 100:2810, 1997). FABP-hCFTR gut corrected C57BL/6J-Cftr$^{tm1Unc}$ KO mice. These CFTR KO mice can survive on normal diet without intestinal obstruction. These strains allow one to directly compare effects of CFTR on epithelial function in the same animal (i.e. lung vs intestine)(Zhou et al. Science 266: 1705, 1994, Steagall et al. Am. J. Respir. Cell Mol. Biol. 22:45, 2000).

The CFTR KO (knock-out) mouse does not totally recapitulate CF lung disease but its lungs are not normal and it provides a valuable animal model to study the mechanisms by which the CFTR gene defect directly contributes to the GSH imbalance. Previous data shows there is a 50% decrease in the lung ELF glutathione concentration. The CFTR KO mouse is useful for determining whether this GSH imbalance plays a role in the exaggerated inflammatory responses to oxidative stress and altered host defense. Another secondary observed condition of the CFTR KO mice is increased oxidation of lung DNA and lipids likely due to low GSH levels.

CFTR KO mice may be used to separate out CFTR's contribution from the other transporters. Many of the ABC transporter genes have been cloned and sequenced and commercial antibodies are readily available for most members of this family due to their interest by cancer researchers as markers for tumor resistance to chemotherapeutics. The use of this extensive database localization, gene expression and function of these proposed transporters in the lung. Inducers of these apical transporters will be assessed by changes in GSH levels (namely bronchoalveolar lavage fluid (BALF) GSH of the lungs). The correlation of this data will determine which of the apical ABC transporters that are critical in regulating ELF GSH levels and may be targets for restoring ELF GSH in the CF lung or other tissues.

Since CFTR modulates only 50% of glutathione transport, other transporters were implicated in the excretion of the remaining glutathione. Thus, other embodiments comprise targeting "non-CFTR" transporters for modulating the excretion of thiol-containing compounds. Still other embodiments specifically aim to increase the thiol-containing compound activity of these "non-CFTR" transporter systems. More specifically, other embodiments aim to increase the thiol-containing compound excretion activity of "non-CFTR" ABC-transporters. In addition, other embodiments aim to increase the thiol-containing compound excretion activity of MRP-1, MRP-2 and/or MDR-1.

Figure 3:
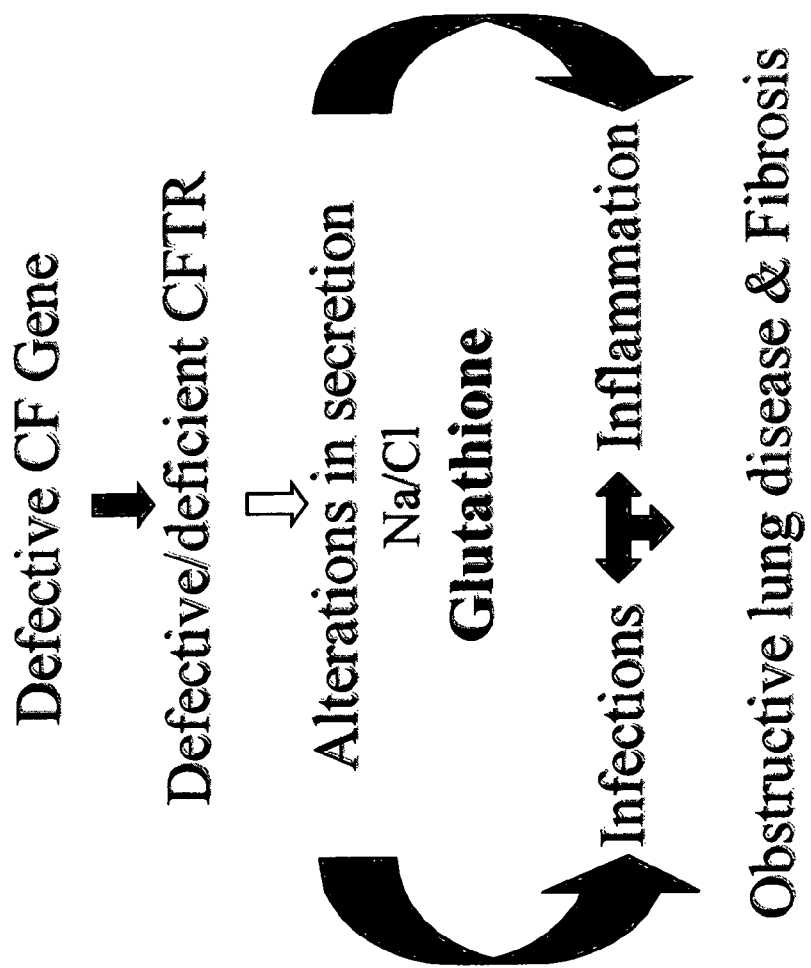
FIG. 3 represents a schematic of the progression of Cystic Fibrosis (CF) and lung disease.
Figure 4:
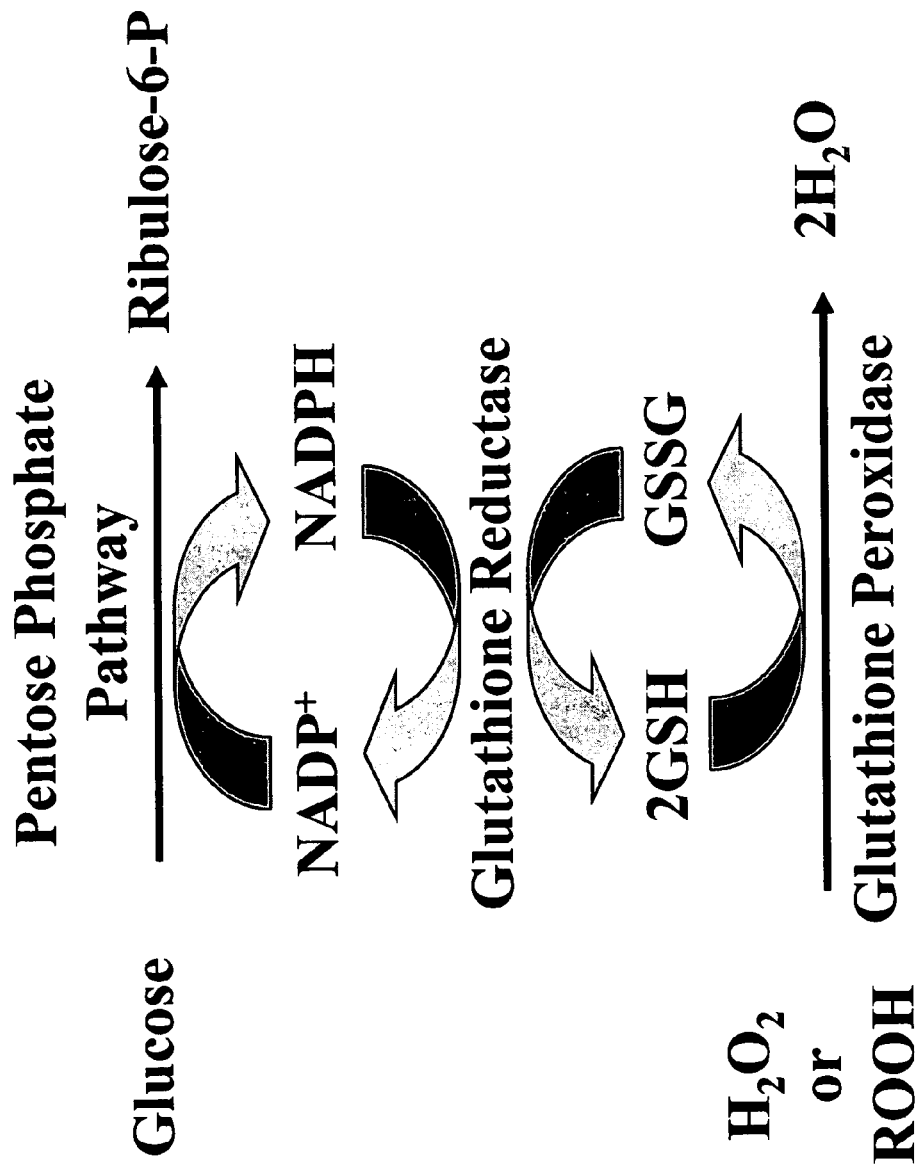
FIG. 4 represents a schematic of detoxification of peroxides by the glutathione redox cycle.

FIG. 3 illustrates defects in the Cystic Fibrosis Transmembrane Regulator Protein (CFTR) may lead to obstructive lung disease and fibrosis. A multitude of mutations in the cystic fibrosis (CF) gene can result in a CFTR deficiency or a defective CFTR. Whether because of a deficiency or a defect in CFTR, alterations in the secretion of Cl⁻ and/or glutathione lead to a perpetuation of infection and inflammation in the lung. Ultimately, this ongoing cycle of infection and inflammation leads to obstructive lung disease, fibrosis and death. BALF and lung tissue may be analyzed for evaluation of the presence or absence of GSH and evaluation of host defense in an anti-*Pseudomonas* assay.

Cell Lines

Several cell lines may be used in the embodiments for example; CRL-1687, HTB-79, and the A549 to test for potential agents that stimulate thiol-containing compound transport. Also, lung (A549), myeloid (HL-60) and prostate (PC-3) human tumor cells for cancer treatment and thiol depletion studies. Both the CRL-1687 and HTB-79 cell lines are derived from human pancreatic adenomas. The primary difference between these two cell lines is their expression of the cystic fibrosis transmembrane regulator protein (CFTR). HTB-79 cells express CFTR while the CRL-1687 cells do not. This difference in CFTR expression provides a method for identifying potential CFTR-dependent mechanisms in experiments where the two lines are exposed to identical conditions but yield differing results. In these investigations, the A549 cells represent secretory cells of the lung epithelium. A549 cells can be grown in a two-compartment culture system that produces separate apical and basolateral compartments that facilitate the identification of apical transport stimulators.

HTB-79 Cells.

Purchased from American Type Culture Collection (ATCC) at passage eighteen. This cell line is derived from a human adenocarcinoma of the pancreas. Similar to normal pancreatic cells, the HTB-79 cells constitutively express CFTR. These cells may be grown in Iscove's modified Dulbecco's medium supplemented with 20% fetal bovine serum. Penicillin (100 U/mL) and streptomycin (100 U/mL) were added to prevent bacterial contamination CRL-1687 Cells CRL-1687 cell are derived from a human adenocarcinoma of the pancreas that does not express the CFTR protein. The cells were grown in complete growth medium RPMI 1640 supplemented with 10% fetal bovine serum. Penicillin (100 U/mL) and streptomycin (100 U/mL) were added to prevent bacterial contamination.

A-549 Cells

A-549 cell may be purchased from ATCC at an unknown passage. This cell line is derived from a lung carcinoma. The cells are maintained in Ham's F12K medium supplemented with 10% fetal bovine serum. Penicillin (100 U/mL) and streptomycin (100 U/mL) were added to prevent bacterial contamination.

A widely used cell line in experimental studies of certain types of cancer is NCI-H69 (H69) (Gazdar et al., Cancer Res. 40, 3502-3507 (1980)) (ATCC HTB 119). This cell line was repeatedly exposed to an anthracycline, such as daunorubicin or epirubicin and preferably doxirubicin (DOX), and selected to produce a "multidrug resistant cell line", designated as H69AR. A description of the procedures that can be used to produce a multidrug resistant cell line such as H69AR is found in Cole, Cancer Chemother Pharmacol. 17, 259-263 (1986) and in Mirski et al., Cancer Research 47, 2594-2598 (1987).

The H69AR cell line (ATCC CRL 11351) is about 50-fold resistant to DOX as compared to the parental H69 cell line. H69AR is also cross-resistant to a wide variety of natural product-type drugs. On the other hand, drugs such as carboplatin, 5-fluorouracil and bleomycin are equally toxic to both sensitive H69 and resistant H69AR cells. Although the cross-resistance pattern of H69AR cells is typical of resistance associated with increased levels of P-gp, these cells are different in that they display little or no collateral sensitivity to hydrophobic drugs such as steroids or local anaesthetics. Another distinguishing feature of H69AR of potential clinical relevance that distinguishes it from P-gp overexpressing cell lines is the limited ability of verapamil, cyclosporin A and other chemosensitizing agents that interact with P-gp, to reverse DOX resistance in these cells. The absence of P-gp overexpression supports the suggestion that H69AR provides a clinically relevant model of drug resistance in lung cancer as well as a model for the overexpression of a thiol-containing compound transporter that is not P-gp.

In one embodiment, a cell line may be used to assay for a substance that increases the thiol-containing compound excretion and/or affects the thiol-containing compound transporter itself. Cells from a cell line may be incubated with a test agent (i.e. a flavone, isoflavone, flavanone etc.) suspected of affecting the thiol-containing compound excretion. Analyzing the amount of thiol-containing compound excretion into an extracellular medium and comparing these results to a control (parental cell line) can determine the effect of an agent on the transporter.

The doses of agent (stimulatory) are estimated from the literature, but will be titrated to determine doses necessary to affect the thiol-containing compound transporter (i.e. lung MRP-2 and MDR-1). In one embodiment, fluorescent dyes may also be transported by the thiol-containing compound transporters (i.e. MDR-1 and MRP-2), such as rhodamine 123 and calcein AM and may be measured in the area under examination (i.e. lung ELF). Thus, the activity of the transporter can be measured by measuring the amount of dye transported.

In one embodiment, a substance that is suspected of increasing the excretion of thiol-containing compounds can be identified. Therefore, it is possible to use this method to identify substances that may be useful in the treatment of thiol-containing compound excretion deficient conditions. At least one of the following compounds for example a flavone, an isoflavones, a flavanones, a flavanols, a benzoic acid derivative, an indole derivative, a 1,4-naphthoquinone, a 3-phenylcoumarin, a 2-phenyl-4-quinoline, a 1-triflavone, a thioflavin, a benzoic acid derivative, a naturally occurring alkaloid, a steroid and a non-steriod anti-inflammatory compound (NSAID) may be used to stimulate thiol-containing compound transport. For use within the context of the embodiments they have the ability to stimulate thiol-containing compound transport in tissues (i.e. epitheilial tissues). The ability to stimulate thiol-containing compound transport may be assessed using any of a variety of systems. For example, in vitro assays using an epithelial cell line such as human lung epithelial A549 (CFTR+) cells or rat lung epithelial RL65 cells (CFTR+), human pancreas epithelial BxPC-3 (CFTR−) or HTB-79 (CFTR+) cells, human colorectal epithelial HT-29 (CFTR+) cells may be treated with at least one of the above compounds and the level of thiol-containing compound transport measured.

Alternatively, the ability to stimulate thiol-containing compound transport may be evaluated within an in vivo assay employing a rodent species that has been genetically engineered to either overexpress or under express apical GSH transporters (i.e. CFTR, MDR or MRP). In general, such assays employ cell monolayers, which may be prepared by standard cell culture techniques. Alternatively, thiol-containing compound transport may be evaluated using epithelial tissue in which the thiol-containing compound across the apical membrane. In either system, thiol-containing compound transportation is evaluated in the presence and absence of a test compound (i.e., a flavone or isoflavone etc.), and those compounds that stimulate thiol-containing compound transport as described above may be used within the methods provided herein.

In one embodiment, dexamethasone may be used as a therapeutic to stimulate thiol-containing compound transport. Dexamethasone was chosen out of a long potential list of inducers based on its ability to induce at least two ABC transporters: MRP-2 and MDR-1. This maximizes the chances of raising ELF GSH levels through 2 separate pathways.

Other suitable therapeutic compounds may be identified using the representative assays as described herein.

Flavones and isoflavones may generally be prepared using well known techniques, such as those described (Shakhova et al., Zh. Obshch. Khim. 32:390, 1962; Farooq et al., Arch. Pharm. 292:792, 1959; and Ichikawa et al., Org. Prep. Prog. Int. 14:183, 1981). Alternatively, such compounds may be commercially available (e.g., from Indofine Chemical Co., Inc., Somerville, N.J. or Sigma-Aldrich, St. Louis, Mo.). Further modifications to such compounds may be made using conventional organic chemistry techniques, which are well known to those of ordinary skill in the art. Most of the compound examples have published methods for synthesis and referenced in the Merck Index (ed. $13^{th}$, 2001).

Nucleic Acids

As described herein, an aspect of the present disclosure concerns isolated nucleic acids and methods of use of isolated nucleic acids. The term "nucleic acid" is intended to include DNA and RNA and can be either be double-stranded or single-stranded. In a preferred embodiment, the nucleic acid is a cDNA comprising a nucleotide sequence such as found in GenBank (i.e. human MDR-1 Gen Bank accession #M2943). In certain embodiments, the nucleic acid sequences disclosed herein have utility as hybridization probes or amplification primers. These nucleic acids may be used, for example, in diagnostic evaluation of tissue samples. In certain embodiments, these probes and primers consist of oligonucleotide fragments. Such fragments should be of sufficient length to provide specific hybridization to a RNA or DNA tissue sample. The sequences typically will be 10-20 nucleotides, but may be longer. Longer sequences greater than 50 even up to full length, are preferred for certain embodiments.

Accordingly, the nucleotide sequences may be used for their ability to selectively form duplex molecules with complementary stretches of genes or RNAs or to provide primers for amplification of DNA or RNA from tissues. Those that are skilled in the art know the stringency needed for effective hybridization of the complementary component.

Many ABC transporters have been cloned (i.e. MDR1, MRP1, MRP2 have been sequenced in their entirety). Embodiments of this invention include induction of thiol-containing compound transporter proteins using gene fusion (i.e. MRP:lacZ for MRP1 or MDR expression) technologies known to those skilled in the art. Other embodiments include the induction of thiol-containing compound transporter genes via stimulation by a factor that binds and or is known to stimulate the synthesis of the sequence of interest (i.e. SP-1) by introducing said factor to a cell or tissue. Other embodiments include the transport of the thiol-containing compound transporter genes via a vesicle or liposome for subsequent expression in the cell or tissue of interest (i.e. lung epithelial cells, liver, pancreas, gastrointestinal cells).

The following codon chart may be used to produce nucleic acids encoding the same or slightly different amino acid sequences of a given nucleic acid:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In certain embodiments, it will be advantageous to employ nucleic acid sequences in combination with an appropriate means, such as a label, for determining hybridization. A wide variety of appropriate indicator means are available (i.e. fluorescent, radioactive, enzymatic or other ligands, such as avidin/biotin) that are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known which can be employed to provide a detection means visible to the human eye or spectrophotometrically, to identify specific hybridization with complementary nucleic acid-containing samples.

In general, it is envisioned that the hybridization probes described herein will not only be useful in solutions as in PCR, for detection of expression of corresponding genes (i.e. thiol-containing compound transporter) but also in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under known conditions.

The gene or gene fragment encoding a polypeptide (i.e. a thiol-containing compound transporter) may be inserted into an expression vector by standard subcloning techniques. An *E. coli* expression vector may be used which produces the recombinant polypeptide as a fusion protein, allowing rapid affinity purification of the protein. Examples of such fusion protein expression systems are the FLAG system (IBI, New Haven, Conn.), and the 6×His system (Qiagen, Chatsworth, Calif.).

Inducible non-fusion expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21 (DE3) or HMS174(DE3) from a resident lambda prophage harboring a T7 gn1 under the transcriptional control of the lacUV 5 promoter.

Examples of vectors for expression in yeast *S. cerivisae* include pYepSec1 (Baldari. et al., (1987) Embo J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.).

Baculovirus vectors available for expression of proteins in cultured insect cells (SF 9 cells) include the pAc series (Smith et al., (1983) Mol. Cell Biol. 3:2156-2165) and the pVL series (Lucklow, V. A., and Summers, M. D., (1989) Virology 170: 31-39).

Expression of a thiol-containing compound transporter protein in mammalian cells may be accomplished using a mammalian expression vector. Examples of mammalian expression vectors include pCDM8 (Seed, B., (1987) Nature 329:840) and pMT2PC (Kaufman et al. (1987), EMBO J. 6:187-195). The expression vector's control functions are often provided by viral material (i.e. polyoma, Adenovirus 2, cytomegalovirus and often, Simian Virus 40). The pRc/CMV vector, nucleic acid introduced into the vector to be expressed is under the control of the enhancer/promoter sequence from the immediate early gene of human cytomegalovirus. Additionally, the vector encodes a gene conferring neomycin resistance. In one embodiment, the recombinant expression vector is capable of directing expression of the nucleic acid preferentially in a particular cell type. This means that the expression vector's control functions are provided by regulatory sequences which allow for preferential expression of a nucleic acid contained in the vector in a particular cell type, thereby allowing for tissue or cell-type specific expression of an encoded protein. For example, a nucleic acid encoding a protein with thiol-containing compound transporter activity can be preferentially expressed in lung cells using promoter and enhancer sequences from a gene which is expressed preferentially in epithelial cell lines such as human lung epithelial A549 (CFTR+) cells or rat lung epithelial RL65 cells (CFTR+), human pancreas epithelial BxPC-3 (CFTR−) or HTB-79 (CFTR+) cells, and human colorectal epithelial HT-29 (CFTR+) cells.

The recombinant expression vector may be a plasmid. The recombinant expression vector further may be a virus, or portion thereof, which allows for expression of a nucleic acid introduced into the viral nucleic acid. For example, replication defective retroviruses, adenoviruses and adeno-associated viruses can be used.

Plasmid vectors introduced into mammalian cells are integrated into host cell DNA at only a low frequency. In order to identify these integrants, a gene that contains a selectable marker (i.e., resistance to antibiotics) is generally introduced into the host cells along with the gene of interest. Preferred selectable markers include those that confer resistance to certain drugs, such as G418 and hygromycin. Selectable markers can be introduced on a separate plasmid from the nucleic acid of interest or, preferably, are introduced on the same plasmid. Host cells transformed with one or more recombinant expression vectors containing a nucleic acid and a selectable marker may be identified by locating the marker. For example, if the selectable marker encoded a gene conferring neomycin resistance (such as pRc/CMV), transformant cells can be selected with G418. Cells that have incorporated the selectable marker gene will survive, while the other cells die.

Alternatively, the protein or parts thereof can be prepared by chemical synthesis using techniques well known in the chemistry of proteins such as solid phase synthesis (Merrifield, 1964, J. Am. Chem. Assoc. 85:2149-2154) or synthesis in homogeneous solution (Houbenweyl, 1987, Methods of Organic Chemistry, ed. E. Wansch, Vol. 15 I and II, Thieme, Stuttgart).

For applications in which the nucleic acid segments are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization The recombinant expression vectors can be designed for expression of thiol-containing compound transporter proteins in prokaryotic or eukaryotic cells. For example, proteins can be expressed in bacterial cells such as *E. coli*, insect cells (using baculovirus), yeast cells or mammalian cells.

Expression in prokaryotes is most often carried out in *E. coli* with vectors containing constitutive or inducible promoters directing the expression of either fusion or non-fusion proteins. Fusion vectors add a number of amino acids usually to the amino terminus of the expressed target gene. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Often, in fusion expression vectors, a proteolytic cleavage site is introduced at the junction of the fusion moiety and the target recombinant protein to enable separation of the target recombinant protein subsequent to purification of the fusion protein (i.e. enzymes, and their cognate recognition sequences, such as Factor Xa, thrombin and enterokinase). Typical fusion expression vectors include pGEX (Amrad Corp., Melbourne, Australia), pMAL (New England Biolabs, Beverly, Md.) and pRIT5 (Pharmacia, Piscataway, N.J.) that fuse maltose E binding protein, or protein A, respectively, to the target recombinant protein.

DNA segments encoding a specific thiol-containing compound transporter gene may be introduced into recombinant host cells and employed for expressing a specific structural or regulatory protein. Alternatively, through the application of genetic engineering techniques, subportions or derivatives of selected genes may be employed.

Where an expression product is to be generated, it is possible for the nucleic acid sequence to be varied while retaining the ability to encode the same product. Reference to the codon chart, provided above, will permit those of skill in the art to design any nucleic acid encoding for the product of a given nucleic acid.

One embodiment includes isolated nucleic acids encoding proteins having biological activity of thiol-containing compound transporters. The term "isolated" refers to a nucleic acid substantially free of cellular material or culture medium when produced by recombinant DNA techniques, or chemical precursors or other chemicals when chemically synthesized. An "isolated" nucleic acid is also free of sequences that naturally flank the nucleic acid (i.e., sequences located at the 5' and 3' ends of the nucleic acid) in the organism from which the nucleic acid is derived.

It will be appreciated that isolated nucleic acids includes nucleic acids having substantial sequence homology with the nucleotide sequence of the thiol-containing compound transporter found in GenBank as disclosed in methods found herein or encoding proteins having substantial homology to the corresponding amino acid sequence.

Some MRP sequences are highly conserved (i.e. MRP-2). There are 12 hydrophobic stretches predicted to be membrane-spanning regions and of functional importance. These regions are important to maintain the integrity of the transporter (U.S. Pat. No. 5,766,880). In addition there are two regions having the structural characteristics of nucleotide binding folds (NBFs) typical of ATP-binding cassette domains (ABC domains). See Hyde, S. C. et al., Nature 346, 362-365 (1990). Part of the structure of these NBFs are conserved in other members of the ABC superfamily of membrane transport proteins. They bind nucleotides and are functionally important. See Higgins, C. F., Ann. Rev. Cell Biol. 8, 67-113 (1992). These regions must be conserved for functional activity. Alternatively, nucleotide and corresponding amino acid substitutions that maintain the structure of an NBF are likely to be tolerated. In addition, some nucleotides encoding an NBF of one member of the ABC superfamily of membrane transport proteins can be substituted for the homologous domain of another member while maintaining function of the protein. (Buschman, F. and Gros, P. Mol. Cell. Biol. 11, 595-603 (1991).

Proteins comprising an amino acid sequence that is 50%, 60%, 70%, 80% or 90% homologous with the amino acid may provide proteins having thiol-containing compound transporter activity. The embodiments encompass a nucleic acid encoding a protein having biological activity of a thiol-containing compound transporter which is at least 25% homologous with the amino acid sequence discussed previously and other yet unknown thiol-containing compound transporters (Borst B B A 1461:347 (1999)).

It will further be appreciated that variant forms of the nucleic acids that arise by alternative splicing of an mRNA corresponding to a cDNA are encompassed by the methods.

Isolated nucleic acids encoding a protein having the biological activity of a thiol-containing compound transporter, as described herein, and having a sequence that differs from a nucleotide sequence due to degeneracy in the genetic code are also within the scope. As one example, DNA sequence polymorphisms within the nucleotide sequence of a thiol-containing compound transporter protein (especially those within the third base of a codon) may result in "silent" mutations in the DNA that do not affect the amino acid encoded. However, it is expected that DNA sequence polymorphisms that do lead to changes in the amino acid sequences of a thiol-containing compound transporter protein will exist within a population. Any and all such nucleotide variations and resulting amino acid polymorphisms are within the scope. Furthermore, there may be one or more isoforms or related, cross-reacting family members of the thiol-containing compound transporter(s) described herein. Such isoforms or family members are defined as proteins related in biological activity and amino acid sequence to thiol-containing compound transporter, but encoded by genes at different loci.

Since thiol-containing compounds are often co-transported with certain drugs, an isolated nucleic acid encoding a protein having the biological activity of thiol-containing compound transporter can be isolated in certain situations from a multidrug resistant cell line which displays a predetermined level of resistance to such drugs as anthracyclines, epipodophyllotoxins and Vinca alkaloids. One example of such a cell line is the H69AR described above. Other suitable cell lines can be produced by stepwise selection of a resistant cell lines in the presence of increasing concentrations of a drug for which resistance is to be acquired over a period of several months to years. A multi-drug resistance cell line is evaluated by exposing it to other drug(s) (i.e vincristine) and determining the cytotoxicity of that drug for the cell line. Once a cell line is identified, a nucleic acid is isolated by preparing a cDNA library from this cell line by standard techniques and screening this library with cDNA produced from total mRNA isolated from the cell line and its drug sensitive parental cell line (i.e. H69AR vs. H69 cells). The library is plated and replica filters are prepared by standard methods. Each set of filters is screened with cDNA prepared from the respective mRNA (i.e. experimental vs. parental). Those cDNA clones displaying increased hybridization with the experimental cDNA when compared to the parental cDNA can be selected from the library. For descriptions of differential cDNA library screening see King, C. R., et al. J. Biol. Chem. 254, 6781 (1979); Van der Bliek, A. M., et al., Mol. Cell. Biol. 6, 1671 (1986).

Determination of whether a cDNA so isolated has the biological activity of a thiol-containing compound transporter can be accomplished by expressing the cDNA in a parental mammalian cell, by standard techniques, and assessing whether expression in the cell of the protein encoded by the cDNA confers on the cell the ability to transport thiol-containing compounds used in its isolation and identification. A cDNA having the biological activity of a thiol-containing compound transporter so isolated may be sequenced by standard techniques, such as dideoxynucleotide chain termination or Maxam-Gilbert chemical sequencing, to determine the nucleic acid sequence and the predicted amino acid sequence of the encoded protein.

Alternatively, a genomic DNA library can be similarly screened to isolate a genomic clone encompassing a gene encoding a protein having thiol-containing compound transporter activity. A human thiol-containing compound transporter gene has been previously mapped to chromosome 16 (MRP, U.S. Pat. No. 5,766,880). Therefore, a chromosome 16 library rather than a total genomic DNA library can also be used to isolate a human thiol-containing transporter gene(s). Nucleic acids isolated by screening of a cDNA or genomic DNA library can be sequenced by standard techniques.

An isolated nucleic acid that is DNA can also be isolated by selectively amplifying a nucleic acid encoding a protein having thiol-containing compound transporter activity using the polymerase chain reaction (PCR) method and genomic DNA or mRNA. cDNA from mRNA can be prepared by a variety of well-known techniques (i.e. by using the guanidinium-thiocyanate extraction procedure of Chirgwin et al., Biochemistry, 18, 5294-5299 (1979).) It is possible to design synthetic oligonucleotide primers from the nucleotide sequence for use in a PCR reaction. A nucleic acid can be amplified from cDNA or genomic DNA using these oligonucleotide primers and standard PCR amplification techniques. The nucleic acid so amplified can be cloned into an appropriate vector and characterized by DNA sequence analysis.

An isolated nucleic acid of the embodiments that is RNA can be isolated by cloning a cDNA into an appropriate vector which allows for transcription of the cDNA to produce an RNA molecule which encodes a protein having thiol-containing compound transporter activity. For example, a cDNA can be cloned downstream from a promoter (such as T7 and induced by T7 polymerase). The RNA product can be isolated by standard techniques.

A nucleic acid of the embodiments, for instance an oligonucleotide, can also be chemically synthesized using standard techniques. Various methods of chemically synthesizing polydeoxynucleotides are known, including solid-phase synthesis which, like peptide synthesis, has been fully automated in commercially available DNA synthesizers (See i.e., Itakura et al. U.S. Pat. No. 4,598,049; Caruthers et al. U.S. Pat. No. 4,458,066; and Itakura U.S. Pat. Nos. 4,401,796 and 4,373,071).

The identification of the initiation codon and untranslated sequences of a thiol-containing compound transporter can be evaluated using currently available computer software designed for the purpose (i.e. PC/Gene—IntelliGenetics Inc., Calif.). The intron/exon structure and the transcription regulatory sequences of the gene encoding the thiol-containing compound transporter cDNA can be identified using a nucleic acid to probe a genomic DNA clone library. Regulatory elements, such as promoter and enhancers necessary for expression of the gene encoding the thiol-containing compound transporter in various tissues, can be identified using conventional techniques. The function of the elements can be confirmed by using them to express a reporter gene such as the bacterial gene lacZ that is operatively linked to the fragments. Such a construct can be introduced into cultured cells using standard procedures or into non-human transgenic animal models. In addition to identifying regulatory elements in DNA, such constructs can also be used to identify nuclear proteins interacting with said elements, using techniques known in the art.

The isolated nucleic acids or oligonucleotide fragments of the isolated nucleic acids allow construction of nucleotide probes for use in the detection of nucleotide sequences in biological materials, such CF patient lung cells. A nucleotide probe can be labelled with a radioactive element which provides for an adequate signal as a means for detection and has sufficient half-life to be useful for detection, such as $^{32}P$, $^{3}H$, $^{14}C$ or the like. Other materials that can be used to label the probe include antigens that are recognized by a specific labelled antibody, fluorescent compounds, enzymes, antibodies specific for a labelled antigen, and chemiluminescent compounds.

The nucleic acids can confer increases in thiol-containing compound transport due to exposure to drugs such as anthracyclines, cis platinum, bleomycin, epipodophyllotoxins and Vinca alkaloids on a drug sensitive cell when transfected into the cell. As well as conferring increased transport of thiol-containing compounds, these drugs can serve as selecting agents when preparing a transformant host cell rather than using an independent selectable marker (such as neomycin resistance). (Croop et al., U.S. Pat. No. 5,198,344). Cells may be selected by exposure to one or more drugs for which thiol-containing compound transport increase is conferred by the nucleic acid expression.

An isolated nucleic acid can be tested for thiol-containing compound transporter activity by incorporating the nucleic acid into a recombinant expression vector, transforming a mammalian cell with the recombinant expression vector to make a transformant host cell as described above and testing the ability to excrete thiol-containing compound(s). For example, in a preferred embodiment, the transformant host cell is an epithelial cell, and the thiol-containing compound transporter ability of transfected epithelial cell is compared to that of untransfected epithelial cell or preferably to epithelial cells transfected with the parental expression vector lacking the nucleic acid encoding a protein having thiol-containing compound transporter activity. One embodiment includes the increase in thiol-containing compound transporter activity. Other embodiments include increased apical localized thiol-containing compound transporter activity.

Protein Purification

Various methods for quantifying the degree of purification of the protein or peptide will be known to those of skill in the art in light of the present disclosure. These include, for example, determining the specific activity of an active fraction, or analysis by SDS/PAGE to identify the number of polypeptides in a given fraction. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will be dependent upon the particular assay technique chosen to follow the purification and whether or not the expressed protein or peptide exhibits a detectable activity.

Methods for purifying various forms of proteins are known. (i.e., Protein Purification, ed. Scopes, Springer-Verlag, New York, N.Y., 1987; Methods in Molecular Biology: Protein Purification Protocols, Vol. 59, ed. Doonan, Humana Press, Totowa, N.J., 1996). The methods disclosed in the cited references are exemplary only and any variation known in the art may be used. Where a protein is to be purified, various techniques may be combined, including but not limited to cell fractionation, column chromatography (e.g., size exclusion, ion exchange, reverse phase, affinity, etc.), Fast Performance Liquid Chromatography (FPLC), High Performance Liquid Chromatography (HPLC), gel electrophoresis, precipitation with salts, pH, organic solvents or antibodies, ultrafiltration and/or ultracentrifugation.

There is no general requirement that the protein or peptide always be provided in the most purified state. Indeed, it is contemplated that less substantially purified products will have utility in certain embodiments. Partial purification may be accomplished by using fewer purification steps in combination, or by utilizing different forms of the same general purification scheme. Methods exhibiting a lower degree of relative purification may have advantages in total recovery of protein product, or in maintaining the activity of an expressed protein.

One embodiment provides isolated proteins having biological activity of a thiol-containing compound transporter (i.e. MRP2, MDR1 etc.). In a preferred embodiment the protein having biological activity of a thiol-containing compound transporter comprises an amino acid sequence found in GenBank (i.e. human p-glycoprotein, MDR-1 GenBank accession #M29432). Proteins having biological activity of a thiol-containing compound transporter that have substantial sequence homology to the amino acid sequence of an ABC transporter as defined above, are also encompassed herein. Furthermore, proteins having biological activity of a thiol-containing compound transporter that are encoded by nucleic acids which hybridize under high or low stringency conditions to a nucleic acid comprising a nucleotide sequence described previously are encompassed. Preferred immunogenic portions correspond to regions of the protein not conserved in other ABC superfamily members, (i.e. outside of the two NBF domains), and include regions between the 12 membrane spanning regions. An immunogenic portion will be of at least about eight amino acids in length.

Molecules which bind to a protein including the antibodies, bispecific antibodies and tetrameric antibody complexes, can be used in a method for identifying thiol-containing compound transporters by labelling the molecule with a detectable substance, contacting the molecule with cells and detecting the detectable substance bound to the cells. A molecule which binds to a protein may be used in a method for increasing the activity of the thiol-containing compound transporter (i.e. by inhibiting the secretion of interfering compounds and/or activating the excretion of thiol-containing compound secretion).

Cancer Therapy

Combined Cancer Therapy. Tumor cell resistance to DNA damaging agents represents a major problem in clinical oncology. One goal of current cancer research is to find ways to improve the efficacy of chemo- and radiotherapy. In one embodiment, a combination therapy may be used to treat a subject having or at risk of developing cancer. For example, combine traditional therapies, such as radiation therapy and chemotherapy, with treatments disclosed herein such as treating the subject with an agent to increase thiol-containing compound transport in a tumor cell population.

In one embodiment, to kill cells, inhibit cell growth, inhibit metastasis, inhibit angiogenesis or otherwise reverse or reduce the malignant phenotype of tumor cells, using the methods and compositions of the present invention. In accordance with this particular embodiment, a "target" cell may be contacted with a compound and or agent to increase thiol-containing compound transport such as secretion of GSH from the target cell and the target cell may be treated with another cancer therapy. These treatments would be provided in a combined amount effective to reduce or inhibit proliferation of the target cell. This process may involve contacting the cells with the agent(s) or other anti-cancer treatment simultaneously or one after the other. This may be achieved by contacting the cell with a single composition or pharmacological formulation that includes one or more agents, or by contacting the cell with two distinct treatments simultaneously, wherein one treatment includes an anti-cancer treatment and the other includes an agent to increase thiol-containing compound transport.

To achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use include, e.g., adriamycin, 5-fluorouracil (5FU), etoposide (VP-16), camptothecin, actinomycin-D, mitomycin C, cisplatin (CDDP) and even hydrogen peroxide. It is also encompasses the use of a combination of one or more DNA damaging agents, whether radiation-based or actual compounds, such as the use of X-rays with cisplatin or the use of cisplatin with etoposide.

In one embodiment, tumor cells may be treated with an agent disclosed herein in addition to at least one other form of cancer treatment This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition including a compound such as, adriamycin, 5-fluorouracil, etoposide, camptothecin, actinomycin-D, or mitomycin C. The agent may be prepared and used as a combined therapeutic composition, or kit, by combining it with an antisense or expression construct, as described above. Agents that directly cross-link nucleic acids, specifically DNA, are envisaged to facilitate DNA damage leading to a synergistic, antineoplastic combination. Agents such as cisplatin, and other DNA alkylating agents are also contemplated. Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered intravenously through bolus injections at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. A number of nucleic acid precursors have been developed for this purpose. Particularly useful are agents that have undergone extensive testing and are readily available, such as 5-fluorouracil (5-FU). Although quite toxic, 5-FU is applicable in a wide range of carriers, including topical. However intravenous administration with doses ranging from 3 to 15 mg/kg/day is commonly used.

Other factors that cause DNA damage and have been used extensively include γ-rays, X-rays, and/or the directed delivery of radioisotopes to tumor cells. Other forms of DNA damaging factors also are contemplated such as microwaves and UV-irradiation. It is most likely that all of these factors effect a broad range of damage to DNA, on the precursors of DNA, the replication and repair of DNA, and the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA Office of Biologics standards. The regional delivery of antisense or expression constructs to patients with cancer will be a very efficient method for delivering a therapeutically effective gene to counteract the clinical disease. Similarly, chemo- or radiotherapy may be directed to a particular, affected region of the subject's body. Alternatively, systemic delivery of expression construct and/or the agent may be appropriate in certain circumstances, for example, where extensive metastasis has occurred.

It is contemplated that combination with other therapies such as gene therapies may be advantageous. Any other tumor-related gene conceivably can be targeted in this manner, for example, p21, p53, Rb, APC, DCC, NF-1, NF-2, p16, FHIT, WT-1, MEN-I, MEN-II, VHL, FCC, MCC, ras, myc, neu, raf erb, src, fms, jun, trk, ret, gsp, hst, bcl and abl.

Hyperthermia Therapy

As incorporated herein, any method known in the art for hyperthermia use in cancer therapy is contemplated. In one embodiment, hyperthermia treatment may be combined with any method disclosed herein for inducing thiol-containing compound transport. Alternatively, hyperthermia treatment may be combined with the use of any other cancer treatment and/or agent as well as a thiol-containing compound transporter inducing agent. It is contemplated herein that a cancerous mass identified in a subject may first be treated with hyperthermia followed by at least one additional anti-cancer treatment and at least one thiol-containing compound transporter inducing agent.

Types of Hyperthermia

In some embodiments, hyperthermia may be used in combination with thiol-containing compound reducing agents such as chalcones, flavones and/or substituted phenol compounds. One or more hyperthermia applications may be used such as local or regional hyperthermia in combination with these other treatments. In local hyperthermia, heat is applied to a small area, such as a tumor, using various techniques that deliver energy to heat the tumor. Different types of energy may be used to apply heat, including microwave, radiofrequency, and ultrasound. Depending on the tumor location, there are several approaches to local hyperthermia: External approaches are used to treat tumors that are in or just below the skin. Intraluminal or endocavitary methods may be used to treat tumors within or near body cavities, such as the esophagus or rectum. Interstitial techniques may be used to treat tumors deep within the body, such as brain tumors. This technique facilitates heating the tumor to higher temperatures than external techniques. Under anesthesia, probes or needles may be inserted into the tumor. Imaging techniques, such as ultrasound, may be used to make sure the probe is properly positioned within the tumor. The heat source is then inserted into the probe. Radiofrequency ablation (RFA) is a type of interstitial hyperthermia that uses radio waves to heat and kill cancer cells.

Alternatively, in regional hyperthermia, various approaches may be used to heat large areas of tissue, such as a body cavity, organ, or limb. For example, deep tissue approaches may be used to treat cancers within the body, such as cervical or bladder cancer. External applicators are positioned around the body cavity or organ to be treated, and microwave or radiofrequency energy is focused on the area to raise its temperature. Regional perfusion techniques may be used to treat cancers in the arms and legs, such as melanoma, or cancer in some organs, such as the liver or lung. In this manner, some subject blood is removed, heated, and perfused back into the limb or organ. Anticancer drugs may be given during this treatment. Continuous hyperthermic peritoneal perfusion (CHPP) is a technique used to treat cancers within the peritoneal cavity, including primary peritoneal mesothelioma and stomach cancer. During surgery, heated anticancer drugs flow from a warming device through the peritoneal cavity. The peritoneal cavity temperature reaches 106-108° F. Whole-body hyperthermia is used to treat metastatic cancer that has spread throughout the body. This can be accomplished by several techniques that raise the body temperature to 107-108° F., including the use of thermal chambers (similar to large incubators) or hot water blankets.

Antibodies

The proteins used in the methods, or portions thereof, can be used to prepare antibodies specific for the proteins. Antibodies can be prepared which bind a distinct epitope in an unconserved region of the protein. An unconserved region of the protein is one that does not have substantial sequence homology to other proteins, for example other members of the ABC superfamily of membrane transport proteins. For example, unconserved regions encompassing sequences between the twelve membrane spanning regions mentioned previously and excluding conserved regions (i.e. the NBF domains), can be used. Alternatively, a region from one of the two NBF domains can be used to prepare an antibody to a conserved region of a thiol-containing compound transporter protein. An antibody to a conserved region may be capable of reacting with other members of the ABC family of membrane transport proteins. Conventional methods can be used to prepare the antibodies. For example, by using a peptide of a thiol-containing compound transporter protein, polyclonal antisera or monoclonal antibodies can be made using standard methods. A mammal, (e.g., a mouse, hamster, or rabbit) can be immunized with an immunogenic form of the peptide that elicits an antibody response in the mammal. Techniques for conferring immunogenicity on a peptide include conjugation to carriers or other techniques using kits are well known in the art (Pierce Biochemical). For example, the peptide can be administered in the presence of adjuvant. The progress of immunization can be monitored by detection of antibody titers in plasma or serum. Standard ELISA or other immunoassay can be used with the immunogen as antigen to assess the levels of antibodies. Following immunization, antisera can be obtained and, if desired, polyclonal antibodies isolated from the sera. One embodiment includes the use of specific antibodies that enhance the transport of a thiol-containing compound via a thiol-containing compound transporter possibly by inhibiting a molecule that otherwise decreases the transporter activity. Other embodiments include the use of specific antibodies to inhibit the activity of factors that inhibit thiol-containing compound transport activity.

To produce monoclonal antibodies, techniques are well known in the art. For example, the hybridoma technique originally developed by Kohler and Milstein (Nature 256, 495-497 (1975)) as well as other techniques such as the human B-cell hybridoma technique (Kozbor et al., Immunol. Today 4, 72 (1983)). Hybridoma cells can be screened immunochemically for production of antibodies specifically reactive with the peptide and monoclonal antibodies isolated.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and may be used to make chimeric antibodies containing the immunoglobulin variable region that recognizes the gene product of the thiol-containing compound transporter genes. See, for example, Morrison et al., Proc. Natl. Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes the monoclonal or chimeric antibodies specifically reactive with a protein, or peptide thereof, having the biological activity of a thiol-containing compound transporter as described herein can be further humanized by producing human constant region chimeras, in which parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., Proc. Natl. Acad. Sci. U.S.A., 80, 7308-7312 (1983).

Another method of generating specific antibodies, or antibody fragments, reactive against protein, or peptide thereof, having the biological activity of a thiol-containing compound transporter is to screen expression libraries encoding immunoglobulin genes, or portions thereof, expressed in bacteria with peptides produced from the nucleic acid molecules. (Ward et al., Nature 341, 544-546: (1989); Huse et al., Science 246, 1275-1281 (1989); and McCafferty et al. Nature 348, 552-554 (1990). Screening such libraries with, for example, a thiol-containing compound transporter peptide can identify imunoglobulin fragments reactive with a thiol-containing compound transporter.

The polyclonal, monoclonal or chimeric monoclonal antibodies can be used to detect the proteins of the methods, portions thereof or closely related isoforms in various biological materials, for example they can be used in a radioimmunoassay, histochemical or in an Elisa test. Thus, the antibodies can be used to quantify the amount of a thiol-containing compound transporter protein of the methods. The antibodies of the methods can be used to determine the role of a thiol-containing compound transporter protein in cellular events, particularly its role in thiol-containing compound transport.

The polyclonal or monoclonal antibodies can be coupled to a detectable substance such as enzymes (i.e. horseradish peroxidase, alkaline phosphatase, glucose oxidase and galactosidase) and luminescent material such as luminol; and radioactive material such as $^{125}I$, $^{131}I$, $^{35}S$ or $^{3}H$.

The embodiments provide a method for identifying a thiol-containing compound transporter(s) using the disclosed activating agents, proteins, nucleic acids and antibodies. One embodiment further provides methods for increasing the thiol-containing compound transporter activity and/or expression. Furthermore, another embodiment provides diagnostic kits for identifying thiol-containing compound transporters.

The compositions are administered to subjects in a biologically compatible form suitable for pharmaceutical administration in vivo. By "biologically compatible form suitable for administration in vivo" is meant a form of the active agent (i.e. pharmaceutical chemical, protein, gene, antibody etc of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of an antibody reactive with a thiol-containing compound transporter protein may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

In one embodiment, the compound (i.e. pharmaceutical chemical, gene, protein, antibody etc of the embodiments) may be administered in a convenient manner such as by injection such as subcutaneous, intravenous, by oral administration, inhalation, transdermal application, intravaginal application, topical application, intranasal or rectal administration. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be inhaled in order to make the compound bioavailable to the lung.

A compound may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. To administer a compound that stimulates a thiol-containing compound transporter protein by other than parenteral administration, it may be necessary to coat the compound with, or co-administer the compound with, a material to prevent its inactivation. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) J. Neuroimmunol 7:27). The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by various antibacterial and antifungal agents (i.e., parabens, chlorobutanol, phenol, ascorbic acid, thimerosal, and the like). In many cases, it will be preferable to include isotonic agents, for example, sugars, polyalcohols such as manitol, sorbitol, sodium chloride in the composition. A compound such as aluminum monostearate and gelatin can be included to prolong absorption of the injectable compositions.

Sterile injectable solutions can be prepared by incorporating active compound (i.e. a chemical that increases the activity of thiol-containing compound transporter protein) in the required amount in an appropriate solvent with one or a combination of ingredients enumerated above, as required, followed by filtered sterilization. Generally, dispersions are prepared by incorporating the active compound into a sterile vehicle that contains a dispersion medium and other required ingredients from those enumerated above. In the case of sterile powders for the preparation of sterile injectable solutions, the preferred methods of preparation are vacuum drying and freeze-drying which yields a powder of the active ingredient (i.e. a chemical agent, antibody etc.) plus any additional desired ingredient from a previously sterile-filtered solution thereof.

When the active agent is suitably protected, as described above, the composition may be orally administered (or otherwise indicated), for example, with an inert diluent or an assimilable edible carrier. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active agent and the particular therapeutic effect to be achieved, and (b) the limitations inherent an active agent for the therapeutic treatment of individuals.

Aqueous compositions comprise an effective amount of a therapeutic protein, compound, peptide, epitopic core region, stimulator (i.e. dexamethasone, rutin, MDR-2 protein), inhibitor, and the like, dissolved or dispersed in a pharmaceutically acceptable carrier or aqueous medium. Aqueous compositions of gene therapy vectors expressing any of the foregoing are also contemplated.

Aqueous compositions comprise an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration (i.e. formulated for injection via the intravenous, intramuscular, sub-cutaneous, intralesional, or even intraperitoneal routes). The preparation of an aqueous composition that contains an active component or ingredient will be known. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi.

Solutions of the active compounds as free-base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. Prolonged absorption of the injectable compositions can be brought about by the use in the compositions of agents delaying absorption, for example, aluminum monostearate and gelatin.

A therapeutic agent can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580).

The active therapeutic agents may be formulated within a mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used.

In another embodiment, nasal solutions or sprays, aerosols or inhalants may be used to deliver the compound of interest. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis. Inhalation preparations may include solutions or dry powder formulations that are commonly used along with a propellant in the formulation of therapeutics used for the treatment of asthmatics.

Additional formulations that are suitable for other modes of administration include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

A pharmaceutical composition may be prepared with carriers that protect active ingredients against rapid elimination from the body, such as time-release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others are known.

Particularly preferred are methods in which the therapeutic compound(s) are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers).

Pharmaceutical compositions are administered in an amount, and with a frequency, that is effective to inhibit or alleviate the symptoms of a thiol-containing compound transporter deficient condition (i.e. CF) and/or to delay the progression of the disease. The precise dosage and duration of treatment may be determined empirically using known testing protocols or by testing the compositions in model systems known in the art and extrapolating therefrom. Dosages may also vary with the severity of the disease. A pharmaceutical composition is generally formulated and administered to exert a therapeutically useful effect while minimizing undesirable side effects. In general, an oral dose ranges from about 200 mg to about 1000 mg, which may be administered 1 to 3 times per day. It will be apparent that, for any particular subject, specific dosage regimens may be adjusted over time according to the individual need.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as grape or orange flavor In certain broad embodiments, the oligo- or polynucleotides and/or expression vectors may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are cationic lipid-nucleic acid complexes, such as lipofectamine-nucleic acid complexes.

In certain embodiments, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable. Where a bacterial promoter is employed in the DNA construct, it also will be desirable to include within the liposome an appropriate bacterial polymerase.

Lipids suitable for use accordingly can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform, chloroform/methanol or t-butanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Liposomes used accordingly can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules will form a bilayer, known as a lamella, of the arrangement XY—YX.

Liposomes within the scope can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min to 2 hours, depending on the desired volume of the liposomes. The composition can be dried further in a desiccator under vacuum. The dried lipids generally are discarded after about 1 week because of a tendency to deteriorate with time.

The dried lipids or lyophilized liposomes prepared as described above may be reconstituted in a solution of active agent (i.e. nucleic acid, chemical agent, antibody etc.), and the solution diluted to an appropriate concentration with a suitable solvent known to those skilled in the art. The mixture is then vigorously shaken in a vortex mixer. Unencapsulated active agent is removed by centrifugation. The liposomes are washed resuspended at an appropriate total phospholipid concentration, e.g., about 50-200 mM. The amount of active agent encapsulated can be determined in accordance with standard methods.

In a preferred embodiment, a nucleic acid (thiol-containing compound transporter) and the lipid dioleoylphosphatidylcholine may be employed. For example, nuclease-resistant oligonucleotides may be mixed with lipids in the presence of excess t-butanol. The mixture is vortexed before being frozen in an acetone/dry ice bath. The frozen mixture is lyophilized and hydrated with Hepes-buffered saline (1 mM Hepes, 10 mM NaCl, pH 7.5) overnight, and then the liposomes are sonicated in a bath type sonicator for 10 to 15 min. The size of the liposomal-oligonucleotides typically ranged between 200-300 nm in diameter as determined by the submicron particle sizer autodilute model 370 (Nicomp, Santa Barbara, Calif.).

As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B that encode proteins responsible for transcription regulation of the viral genome, as well as a few cellular genes. E2 expression, including E2A and E2B, allows synthesis of viral replicative functions (i.e. DNA-binding protein, DNA polymerase, and a terminal protein that primes replication). E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus (vii) adenovirus replication is independent of host gene replication, unlike retroviral sequences and (viii) oncogenic risk from adenovirus vectors is thought to be negligible (Grunhaus & Horwitz, 1992).

In general, adenovirus gene transfer systems are based upon recombinant, engineered adenovirus that are rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kB of foreign DNA and can be grown to high titers in 293 cells (Stratford-Perricaudet and Perricaudet, 1991. An embodiment includes substitution of a thiol-containing compound transporter gene or segment of a thiol-containing compound transporter gene under the control of the minimum amount of replication-incompetent adenovirus.

Other viral vectors may be employed as expression constructs. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Horwich et al., 1990).

Several non-viral methods for the transfer of expression vectors into cultured mammalian cells also are contemplated. These include calcium phosphate precipitation (Graham and Van Der Eb, 1973; Chen and Okayama, 1987; Rippe et al., 1990) DEAE-dextran (Gopal, 1985), lipofectamine-DNA complexes, and receptor-mediated transfection (Wu and Wu, 1987; Wu and Wu, 1988). Some of these techniques may be successfully adapted for in vivo or ex vivo use.

Insertional variants include fusion proteins such as those used to allow rapid purification of the polypeptide and also may include hybrid proteins containing sequences from other proteins and polypeptides that are homologues of the polypeptide. For example, an insertional variant may include portions of the amino acid sequence of the polypeptide from one species, together with portions of the homologous polypeptide from another species. Other insertional variants may include those in which additional amino acids are introduced within the coding sequence of the polypeptide. These typically are smaller insertions than the fusion proteins described above and are introduced, for example, to disrupt a protease cleavage site.

Another method for the preparation of the polypeptides use peptide mimetics. Mimetics are peptide-containing molecules that mimic elements of protein secondary structure. (Johnson et al., "Peptide Turn Mimetics" in Biotechnology and Pharmacy, Pezzuto et al., Eds. Chapman and Hall, New York (1993)). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule (i.e. transporting thiol-containing compounds to the outside of the cell). An embodiment includes the use of protein mimetics to mimic the excretion of thiol-containing compounds within a given transporter responsible for thiol-containing compound transport.

Successful applications of the peptide mimetic concept have thus far focused on mimetics of β-turns within proteins, which are known to be highly antigenic. Once the component amino acids of the turn are determined, peptide mimetics may be constructed to achieve a similar spatial orientation of the essential elements of the amino acid side chains.

The embodiments are generally directed to compositions and methods for the treatment of diseases characterized by defective thiol-containing compound transport in tissues (i.e. including cystic fibrosis, and diseases with excessive accumulation of mucus, including cystic fibrosis, chronic bronchitis and asthma). It has been found, within the context, that certain agents (i.e. flavones, isoflavones, flavanones, isoflavanones) are capable of stimulating thiol-containing compound transport in tissues (i.e. epithelial tissues of the airways, intestine, pancreas and other exocrine glands). Such therapeutic compounds may be administered to patients afflicted with a thiol-containing compound transporter deficiency as described herein.

Compound Analysis

In a preferred embodiment, a nucleic acid may include a recombinant expression vector containing nucleic acid with a nucleotide sequence including a thiol-containing compound transporter. Preferably, a cell into which the nucleic acid is transfected is deficient in thiol-containing compound transport so that the effects of a potential activator are assessed in the presence of a single, isolated thiol-containing compound transporter conferring protein. In another preferred embodiment a therapeutic agent and substance to be tested are incubated in culture with the cell and the level of thiol-containing compounds measured in the extracellular media. Alternatively, the cell can be a thiol-containing compound transporter cell in a transgenic animal, transgenic for a nucleic acid, and the therapeutic agent and substance to be tested are administered to the transgenic animal. Furthermore, the cell can be a cell in culture isolated from a thiol-containing compound transporter transgenic animal. The sensitivity of the cell for the therapeutic agent in the presence and absence of the potential therapeutic agent is assessed by determining the concentration of the therapeutic agent that exports a predetermined level of the thiol-containing compound from the cell either in the presence or in the absence of the substance being tested. Once an agent provides positive results on the cellular level and the thiol-containing compound is verified by a measuring device for example an HPLC, a cell system utilizing a membrane to separate the basolateral and apical sides of a cellular monolayer may be used to further test transporter stimulation to release thiol-containing compounds. In addition, if the agent demonstrates positive affects on apical transport of thiol-containing compounds, these agents may be further tested in an animal model for example the mouse lung as described.

One embodiment includes a method for identifying a substance that directly increases the synthesis and/or activity of a thiol-containing compound transporter involving incubating a substance to be tested with a cell and determining the amount of thiol-containing compound in the media.

In one embodiment, anti-thiol-containing compound transporter antibodies labelled with a detectable substance, such as a fluorescent marker, an enzyme or a radioactive-marker may be used to identify cells expressing a thiol-containing compound transporter. Tissue removed from a patient may be used as the cell sample. A tissue section, for example, a freeze-dried or fresh frozen section of tissue (i.e. lung tissue) removed from a patient, may also be used as the sample. The samples can be fixed and the appropriate method of fixation may be chosen depending upon the type of labelling used for the antibodies. Alternatively, a cell membrane fraction can be separated from the tissue removed from a patient and can be used as the sample. Conventional methods such as differential or density gradient centrifugation can be used to separate out a membrane fraction.

A thiol-containing compound transporter cell may be identified by incubating an antibody, for example a monoclonal antibody, with a cell to be tested for thiol-containing compound transporter. Binding of the antibody to the cell is indicative of the presence on the cell of a protein having thiol-containing compound transporter activity. The level of antibody binding to the cell can be compared to the level of antibody binding to a normal control cell, and increased binding of the antibody to the cell as compared to the normal cell can be used as an indicator of increase expression of a thiol-containing compound transporter. Binding of an antibody to a cell (i.e. a cell to be tested or a normal control cell such as a cell from a condition-free patient) may be determined by detecting a substance with which the antibody is labelled. The detectable substance may be directly coupled to the antibody, or alternatively, the detectable substance may be coupled to another molecule that can bind the antibody (i.e. a secondary antibody or anti-antibody).

A thiol-containing compound transporter cell can be detected as described above in vitro in a sample prepared as described above. For example, a section on a microscope slide can be reacted with antibodies using standard immunohistochemistry techniques Additionally, if a single cell suspension of cells can be achieved, the cells can be reacted with antibody and analyzed by flow cytometry. Alternatively, a thiol-containing compound transporter cell can be detected in vivo in a subject bearing a thiol-containing compound transporter deficiency. Labelled antibodies can be introduced into the subject and antibodies bound to the tissue can be detected. For example, the antibody can be labelled with a radioactive marker whose presence and location in a subject can be detected by standard imaging techniques.

The antibodies, and compositions thereof, may also be used to inhibit the non-thiol-containing compound transporter component of a cell. The embodiments provide a method for inhibiting the non-thiol-containing compound transporter region of protein in a cell comprising inhibiting activity of a protein. Preferably, the thiol-containing compound transporter cell is a lung cell. A thiol-containing compound transporter can increase its thiol-containing compound transport by interfering with the non-thiol-containing compound transporter activity of the protein. For example, the ability of a thiol-containing compound transporter protein to transport non-thiol-containing compounds may be impaired. Accordingly, any molecule which binds to a protein having thiol-containing compound transporter activity and whose binding inhibits the non-thiol-containing compound transporter activity of the protein are encompassed by invention.

The methods for increasing the activity of thiol-containing compound transporters and/or the synthesis of thiol-containing compound transporter proteins and/or thiol-containing compound transporter and/or transfection of a thiol-containing compound transporter gene can be applied to patients having a thiol-containing compound transporter deficiency. The compositions and methods can be particularly useful in treating for example lung (i.e. CF), pancreatic, gastrointestinal, vascular, joint, neurodegenerative and biliary diseases and also male infertility.

One embodiment also provides a diagnostic kit for identifying an agent that increases thiol-containing compound transport protein activity and/or expression comprising an agent, a cell and a means for detecting thiol-containing compounds, thiol-containing compound transporter protein; means for determining the amount of protein in the sample; and means for comparing the amount of protein in the sample with a standard. Preferably, the molecule is a monoclonal antibody. Other molecules that can bind a protein having thiol-containing compound transporter activity can be used, including the bispecific antibodies and tetrameric antibody complexes. The diagnostic kit can also contain an instruction manual for use of the kit.

Effects of replenishing thiol-containing compounds in site specific compartments. In one embodiment, cells are treated with one or more agents to increase the transport of thiol-containing compounds (for example, glutathione) into the mitochondria. Loss of CFTR function is associated with diminished mitochondria glutathione levels (see FIG. 11). This may be due to the effects of CFTR directly or indirectly on the mitochondrial glutathione transporter(s). The loss or dysfunction of these mitochondrial glutathione transporters produces a mitochondrial oxidative stress (see FIG. 9). Again, a CFTR defect leads to similar decreases in mitochondrial glutathione levels as seen in the ELF and suggests that other ABC transporters may also be involved and can be used to replenish glutathione transport. A number of diseases have been associated with mitochondrial oxidative stress and include alcoholism and associated disease such as hepatitis and cirrhosis, neurodegenerative diseases (such as Parkinsonism, Alzhiemers, and Hunnigton's Disease), inheritable disorders such as myopathy, chronic alcoholism, optic atrophy, dystonia, Leigh's syndrome, myoclonic epilepsy and ragged red fiber (MERRF), mitochondrial encephalomyopathy, lactic acidosis, and stroke-like episode (MELAS) and diabetes. Any one of these conditions may be a target for treatment by one or more of the disclosed agents to increase the transport of thiol-containing compounds to the mitochondria.

In the foregoing specification, the embodiments have been described with reference to specific exemplary embodiments. It will, however, be evident that various modifications and changes may be made without departing from the broader spirit and scope as detailed in the appended claims. The specification and figures are, accordingly, to be regarded in an illustrative rather than a restrictive sense.

In several embodiments, the restoration of GSH levels has been described. In particular embodiments restoration of lung GSH levels in compromised patients has been described. Some of these embodiments include the restoration of GSH in the mitochondria of the lung thus likely relieving mitochondrial oxidative stress and may also alleviate the exacerbated response to infection-induced inflammation.

In other embodiments, reduction of intracellular GSH levels has been described. (U.S. patent application Ser. No. 10/400,980 and U.S. patent application Ser. No. 11/211,369 are incorporated herein in the entirety). In one embodiment, reducing intracellular GSH in a cell population of subjects suffering from cancer has been described. Some of these embodiments include reducing the levels of GSH in a cancer cell population, as well as, treating the cancer cell population of a subject with at least one additional anti-cancer treatment. These additional anti-cancer treatments may include but is not limited to radiation therapy, chemotherapy, immunotherapy and hyperthermia therapy.

Compounds of the present invention are used to treat benign and malignant tumors, include but are not limited to various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma.

Methods of treating tumors and/or cancer according to the present invention comprise administering to a subject in need thereof an effective amount of one or more compounds in combination with at least one other anti-cancer treatment.

Pharmaceutical compositions based upon these substituted novel chemical compounds include substituted phenol compounds, as well as chalcones and/or flavone compounds in a therapeutically effective amount for the treatment of a condition or disease. The disease or condition includes neoplasia, including cancer, or a related condition or disease. A treatment may include novel chemical compounds (substituted phenol compounds) disclosed herein as well as flavones and/or chalcones in combination with another anti-cancer treatment and optionally in combination with a pharmaceutically acceptable additive, carrier or excipient.

Certain of the disclosed novel compounds as well as chalcones or flavones, in pharmaceutical dosage form, may be used as prophylactic agents for reducing the onset or conditions of a cancerous disease from manifesting itself. In particular, prodrug forms which rely on $C_1$ to $C_{20}$ ester groups or amide groups (preferably a hydroxyl, free amine or substituted nitrogen group) which may be transformed into, for example, an amide or other group may be particularly useful in this context.

Substituted phenol compounds (previously described) or their derivatives, including prodrug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

The embodiments are further illustrated by the following examples and detailed protocols. However, the examples are merely intended to illustrate embodiments and are not to be construed to limit the scope herein. The contents of all references and published patents and patent applications cited throughout this application are hereby incorporated by reference.

EXAMPLES

Example 1

Figure 5:
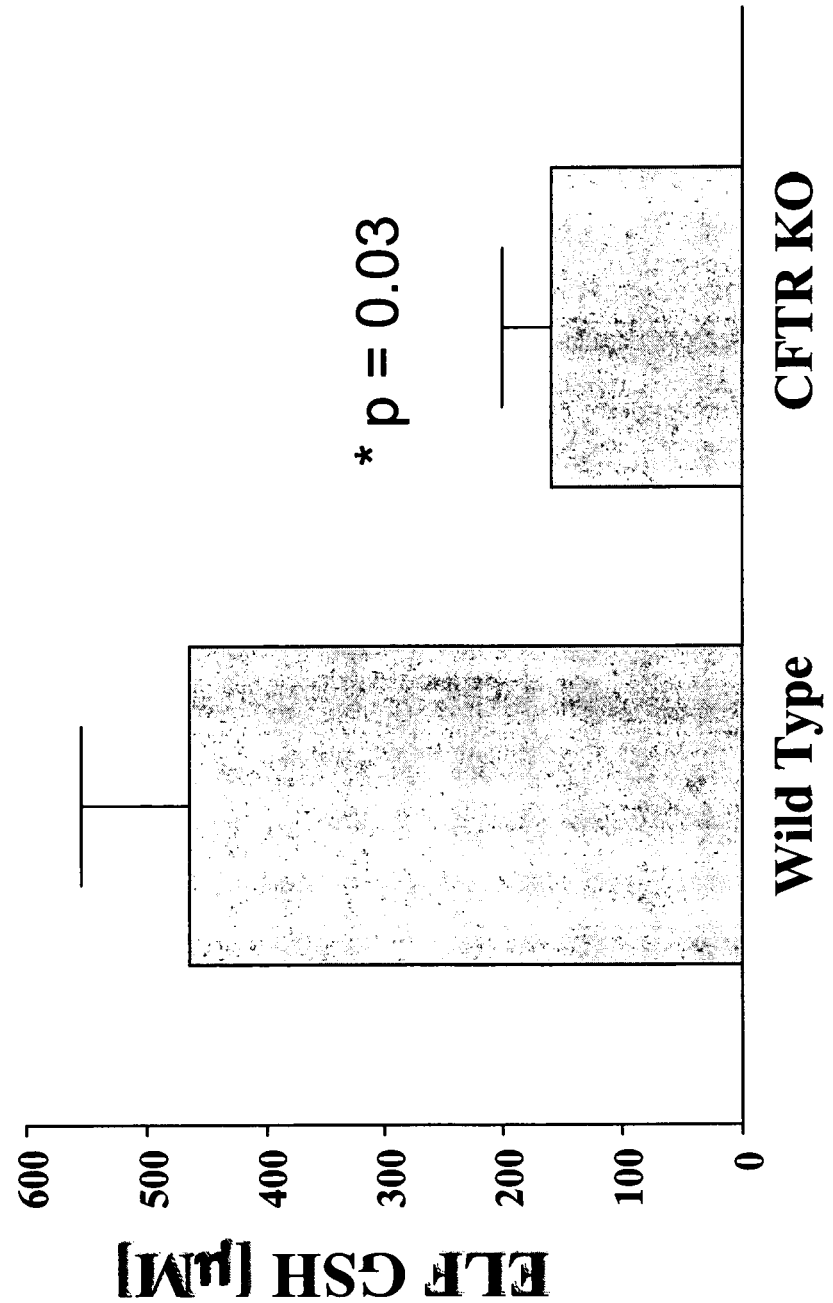
FIG. 5 represents pulmonary ELF concentrations of GSH in Cystic Fibrosis transmembrane Regulator Protein Knockout (CFTR KO) mice compared to a control.

FIG. 5—Reduced Glutathione (GSH) Concentrations in Mouse Epithelial Lining Fluid (ELF). GSH concentrations in ELF were calculated from GSH concentrations in bronchoalveolar lavage fluid (BALF). Briefly, a lung was lavaged through a tracheal canula with three separate 1 mL aliquots of phosphate-buffered saline (pH 7.4). Each aliquot was instilled into the lung and withdrawn only once. All three aliquots were then pooled and centrifuged at 4000×g to remove cells (i.e., alveolar macrophages). The cell-free BALF was acidified with metaphosphoric acid to a final concentration of 0.75% metaphosphoric acid and centrifuged at 10,000×g to pellet the precipitated proteins. GSH concentrations were determined spectrophotometrically with a commercially available assay that forms a chromogen with GSH. ELF concentrations of GSH were calculated from the BALF concentrations multiplied by a dilution factor derived from the difference in serum and BALF urea concentrations. GSH concentrations in ELF of cystic fibrosis transmembrane regulator protein knockout (CFTR-KO) mice were lower (249±59 µM) compared to wild type mice (512.6±63 µM). Data are shown as the mean±standard error for $n \geq 5$ and significance (*) attained at $p \leq 0.05$.

Example 2

Figure 6:
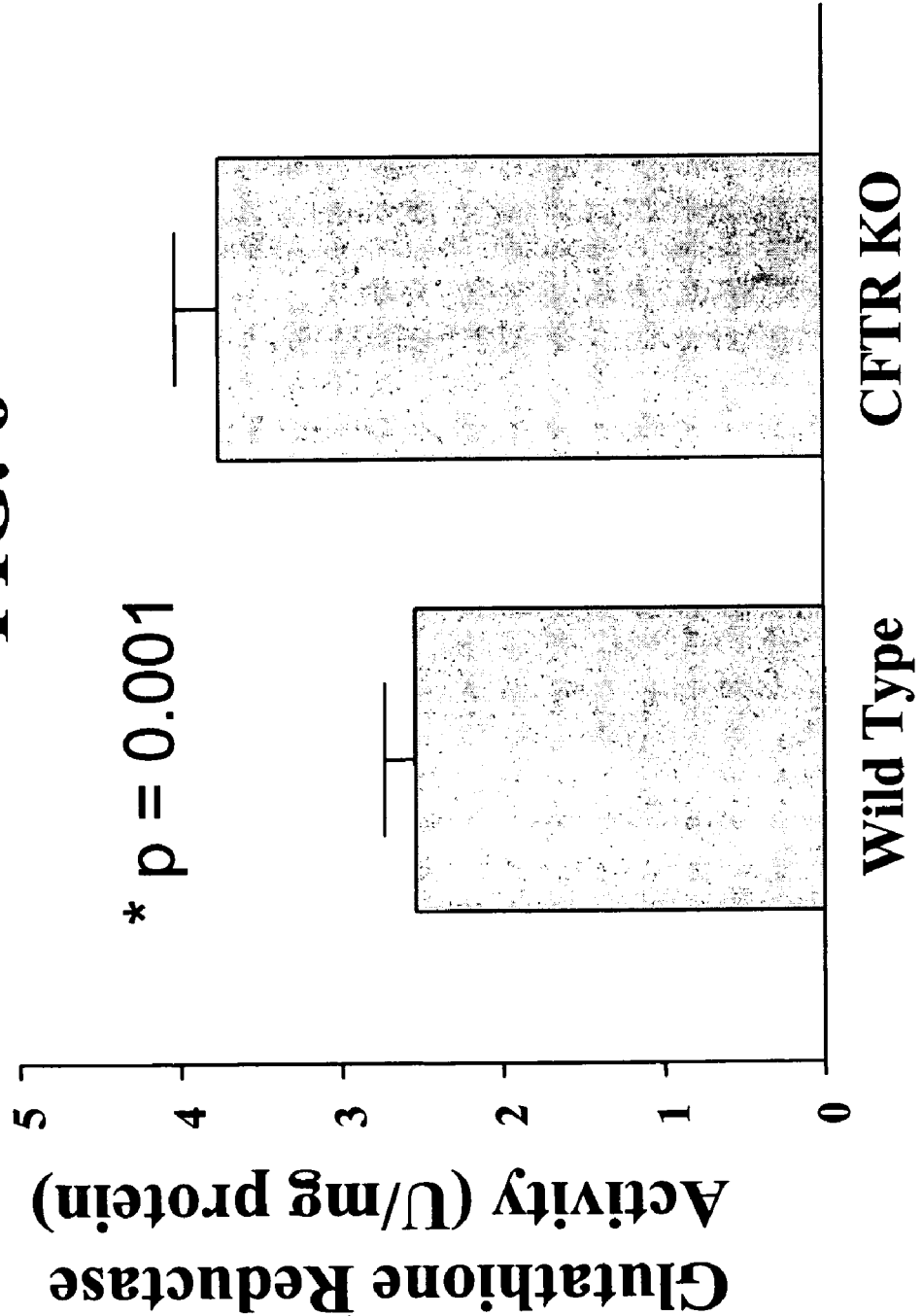
FIG. 6 represents the levels of Glutathione Reductase activity in control versus CFTR KO mice.

FIG. 6 Glutathione Reductase (GR) Activity in Lung Tissue of Wild Type and Cystic Fibrosis Transmembrane Regulator Protein Knockout (CFTR-KO) Mice. Mouse lung tissue (10-25 mg) were ground in liquid nitrogen and dissolved in 800 µL of cold homogenization buffer (50 mM potassium phosphate, 1 mM EDTA, pH 7.5). The sample was centrifuged at 8,500×g for 10 minutes at 4° C. and the supernatant retained for analysis. GR activity in the supernatant was determined spectrophotometrically (340 nm) from the rate of NADPH consumption by GR in the presence of oxidized glutathione (GSSG) using a commercially available kit. GR is expressed as units per milligram of protein in the supernatant. GR activity in CFTR-KO mouse lungs was significantly elevated (3.76±0.27 U/mg protein) compared to WT mouse lungs (2.54±0.19 U/mg protein). Data are shown as the mean±standard error for $n \geq 12$ and significance (*) attained at $p \leq 0.05$.

Example 3

Figure 7:
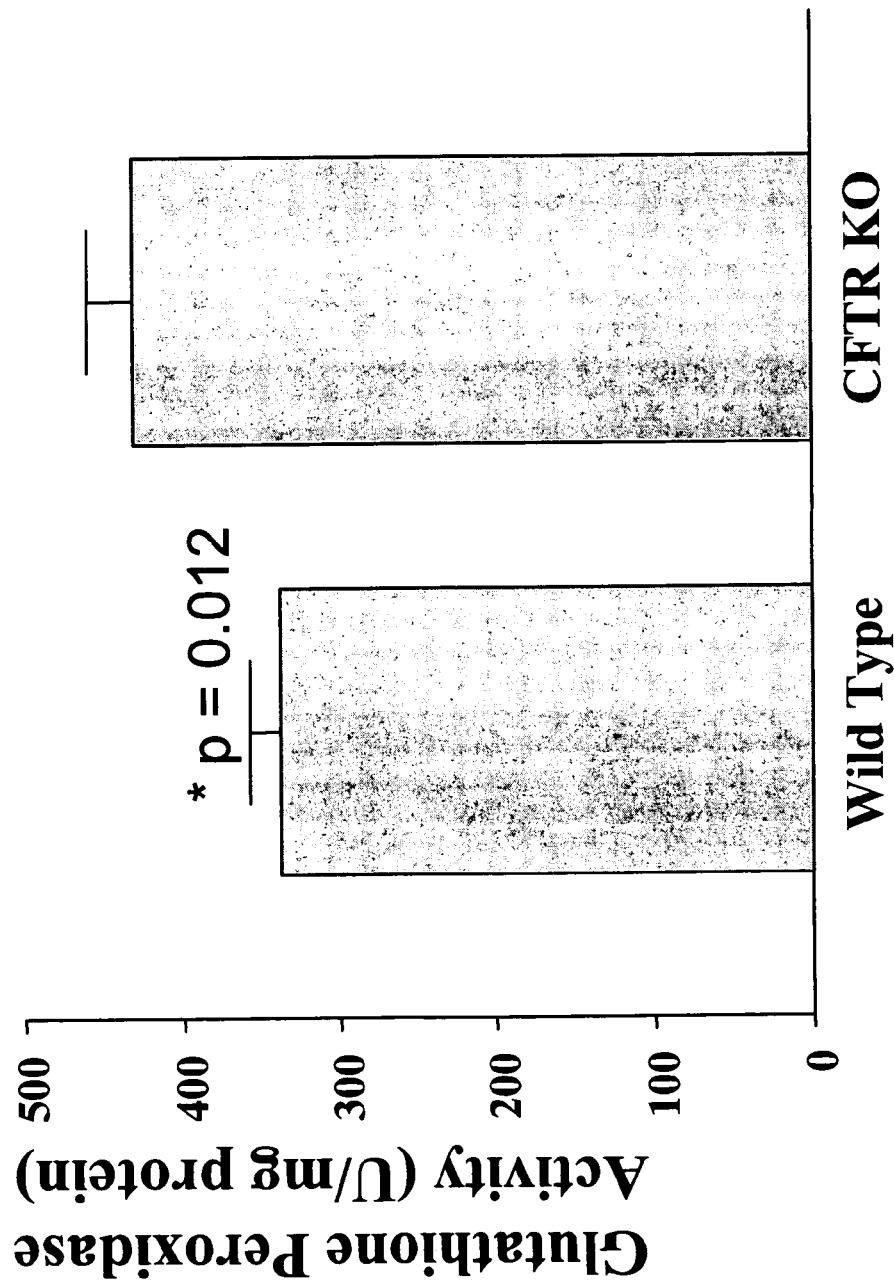
FIG. 7 represents the levels of Glutathione Peroxidase activity in control versus CFTR KO mice.

FIG. 7—Glutathione Peroxidase (GPx) Activity in Lung Tissue of Wild Type and Cystic Fibrosis Transmembrane Regulator Protein Knockout (CFTR-KO) Mice. Mouse lung tissue (10-35 mg) was ground in liquid nitrogen and the ground tissue dissolved in 1.0 mL of cold homogenization buffer (50 mM Tris-HCl, 5 mM EDTA and 1 mM 2-mercaptoethanol, pH 7.5). Homogenate was centrifuged (7,500×g, 15 min., 4° C.) and the supernatant retained for analysis. The GPx activity in the sample was determined from a commercially available kit to which t-butyl-hydroperoxide was added as a GPx substrate to generate oxidized glutathione (GSSG). The rate of NADPH consumption by glutathione reductase in the subsequent reduction of GSSG was used to calculate GPx activity. GPx activity was normalized to sample protein concentrations. CFTR-KO mice had significantly more GPx activity (431±28 U/mg protein) in the lung tissue than WT mice (338±20 U/mg protein). Data are shown as the mean±standard error for $n \geq 10$ and significance (*) attained at $p \leq 0.05$.

Example 4

Figure 8:
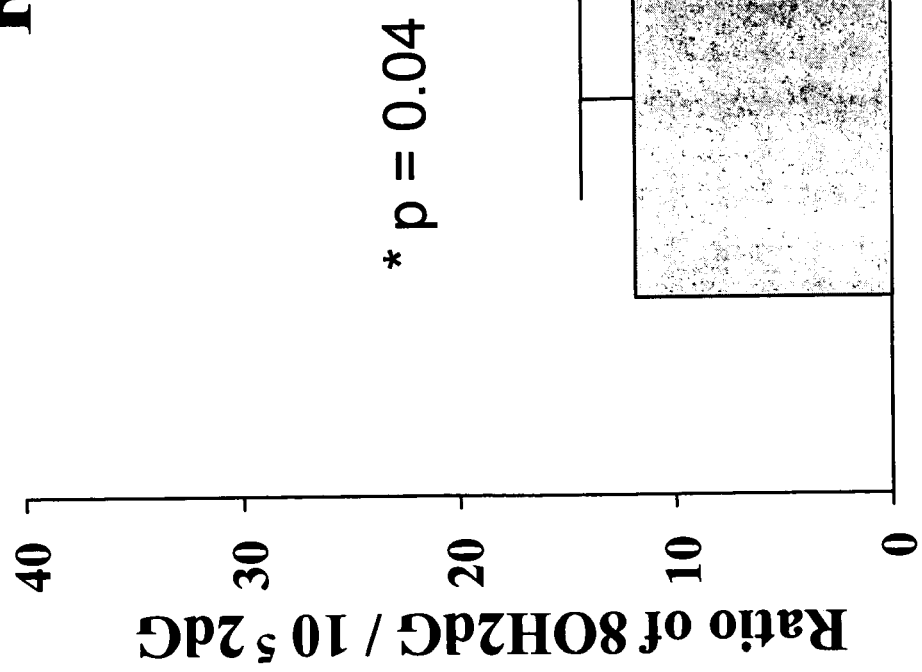
FIG. 8 represents oxidation of DNA in the lungs of control versus CFTR KO mice.

FIG. 8—Concentration of 8-hydroxy-2'-deoxyguanosine (8OH2dG) in Lung Tissue of Wild Type (WT) and Cystic Fibrosis Transmembrane Regulator Protein Knockout (CFTR-KO) Mice. DNA from WT and CFTR-KO was obtained by a chloroform-isoamyl alcohol extraction of proteinase K-digested lung homogenates. The purified DNA was subsequently hydrolyzed to nucleosides with nuclease P1 and alkaline phosphatase. Samples were analyzed for 8OH2dG and 2-deoxyguanosine (2dG) by HPLC coupled with electrochemical and UV detectors. To normalize for differences in DNA yield between lung samples, the ratio of 8OH2dG to $10^5$ 2dG were calculated. Levels of 8OH2dG/$10^5$ 2dG were significantly increased in CFTR-KO lungs (5.67±0.94) compared to WT mice (3.72±0.37). Data are shown as the mean±standard error for $n \geq 8$ and significance (*) attained at $p \leq 0.05$.

Example 5

Figure 9:
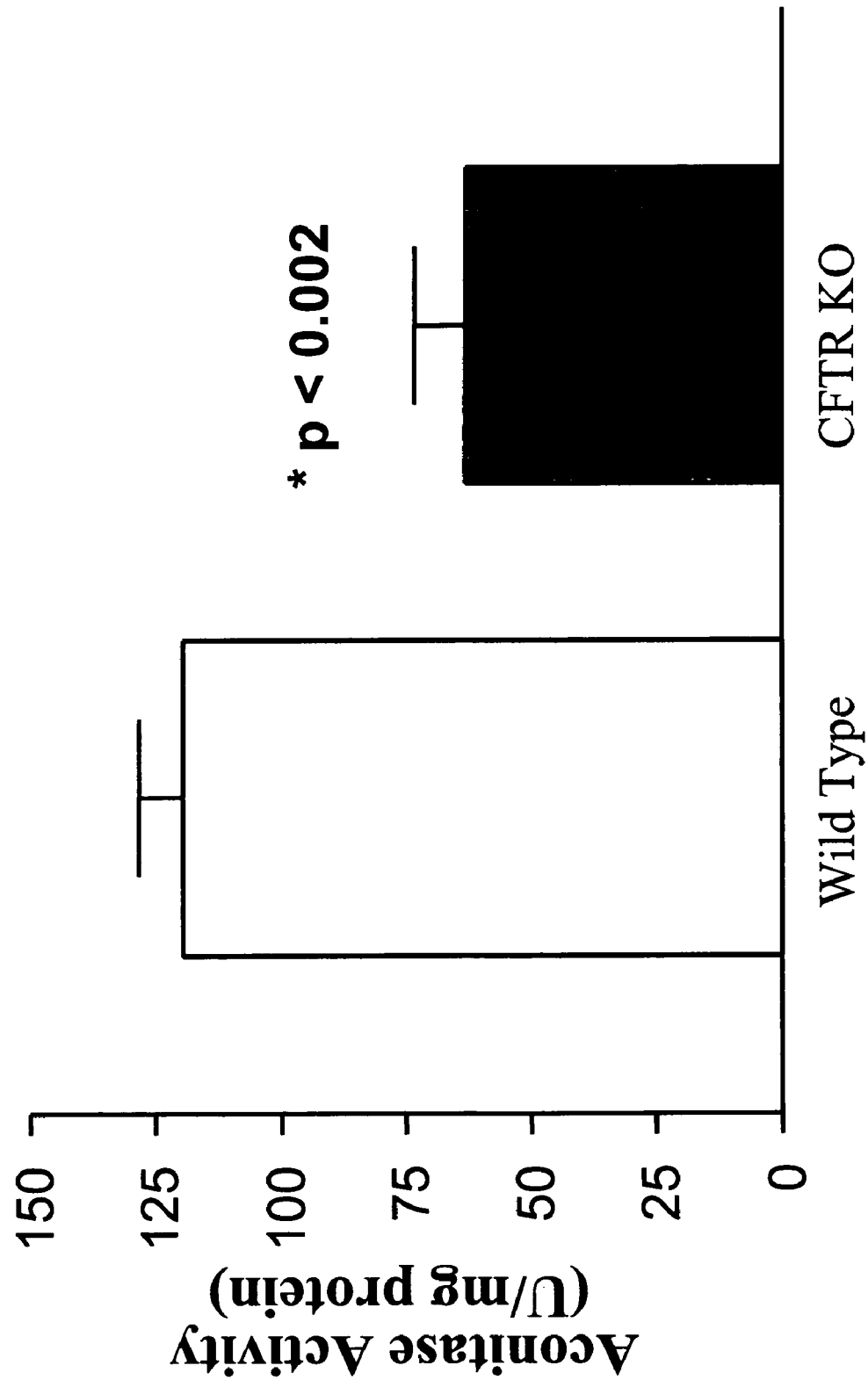
FIG. 9 represents the levels of mitochondrial Aconitase activity in control versus CFTR KO mice.

FIG. 9 Mitochondrial Aconitase activity in the Lungs of Wild Type and Cystic Fibrosis Transmembrane Regulator Protein Knockout (CFTR-KO) Mice. Aconitase is a mitochondrial and cytosolic enzyme that is sensitive to oxidative stress. A loss of aconitase activity in isolated mitochondria can be used as a direct indicator of mitochondrial oxidative stress. Mitochondria from the lungs of wild type (control) and CFTR-KO mice were obtained by differential centrifugation of lung homogenates. Briefly, lungs were homogenized in mitochondrial isolation buffer (210 mM mannitol, 70 mM sucrose, 5 mM Tris-HCl, 1 mM EDTA, pH 7.5) and cellular debris removed by repeated centrifugations at 1,300×g until no pellet was obtained. The supernatant was then centrifuged at 17,000×g to pellet mitochondria. The mitochondria were then resuspended in a small volume of mitochondria lysis buffer (cysteine 1 mM, citric acid 1 mM, Triton X-100 0.5%, pH 7.4) and assayed for aconitase activity. Aconitase activity was determined spectrophotometrically by following the formation of cis-aconitate from isocitrate at 240 nm. Mitochondrial aconitase activity was significantly decreased in CFTR-KO lungs (63.1±10.2 U/mg protein) compared to WT lungs (119.6±8.8 U/mg protein). Data are shown as the mean±standard error for $n \geq 6$ and significance (*) attained at $p \leq 0.05$.

Example 6

Figure 10:
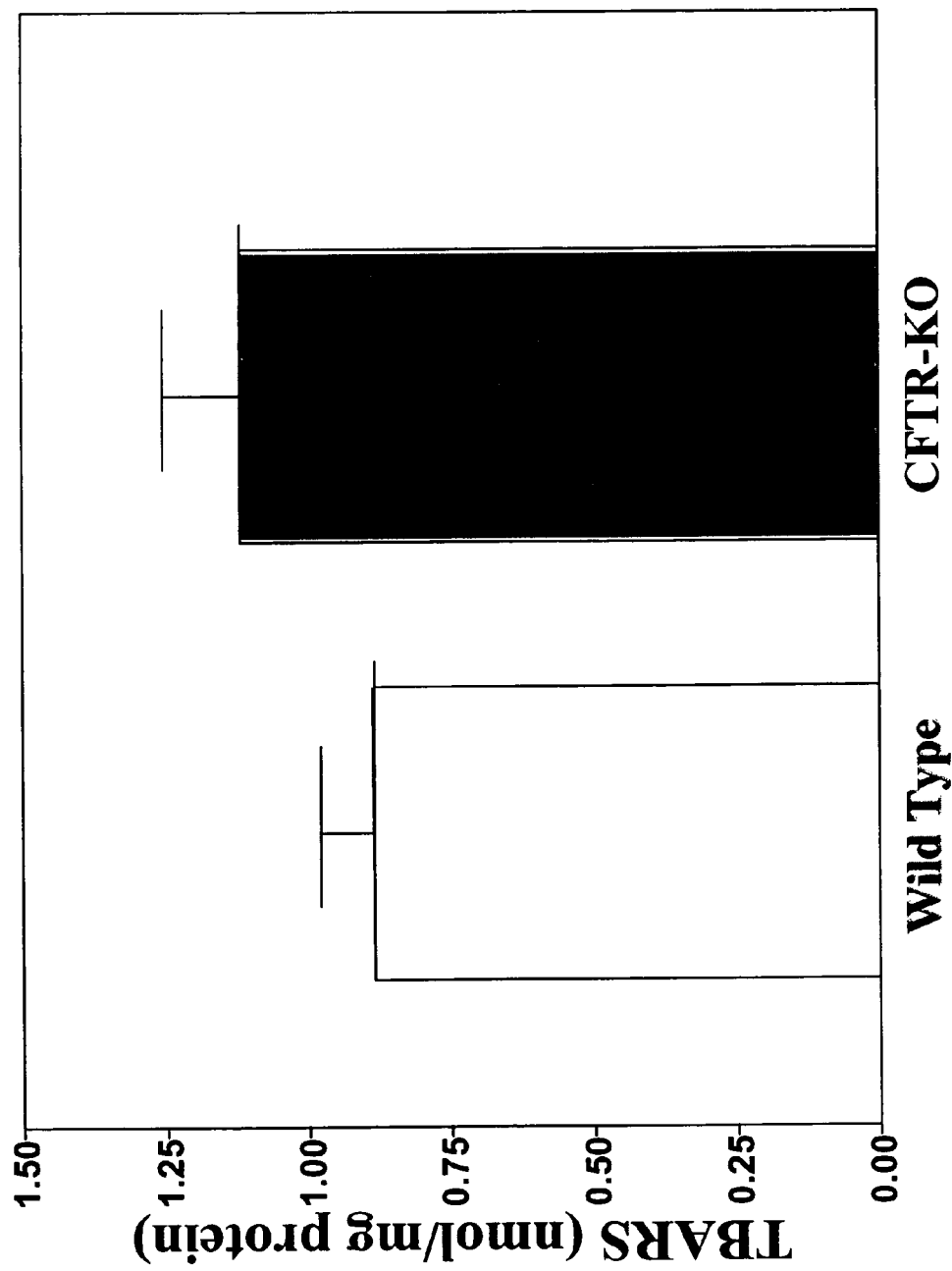
FIG. 10 represents the concentration of lipid peroxidation in the lungs of control versus CFTR-KO mice.

FIG. 10 Concentration of Lipid Peroxidation in Lungs of Wild Type (WT) and Cystic Fibrosis Transmembrane Regulator Protein Knockout (CFTR-KO) Mice. Approximately 25 mg of lung tissue were homogenized in 50 mM phosphate buffer containing 1 mM butylated hydroxytoluene and acidified with an equal volume of phosphoric acid. Thiobarbituric acid is known to reactive with oxidized lipid breakdown products and is a commonly used marker for lipid peroxidation. Thiobarbituric acid was added and the mixture heated at 90° C. for 45 minutes. The chromogen was extracted with n-butanol and the absorbance at 535 nm measured. TBARS concentrations were calculated from a standard curve, normalized for sample protein and presented as the % change from control (WT) arbitrarily set at 100%. Levels of TBARS in CFTR-KO mouse lungs were significantly increased (126.6±8.0%) compared to WT controls (99.85±4.1%). Data are shown as the mean±standard error for $n \geq 6$ and significance (*) attained at $p \leq 0.05$.

Example 7

Figure 11:
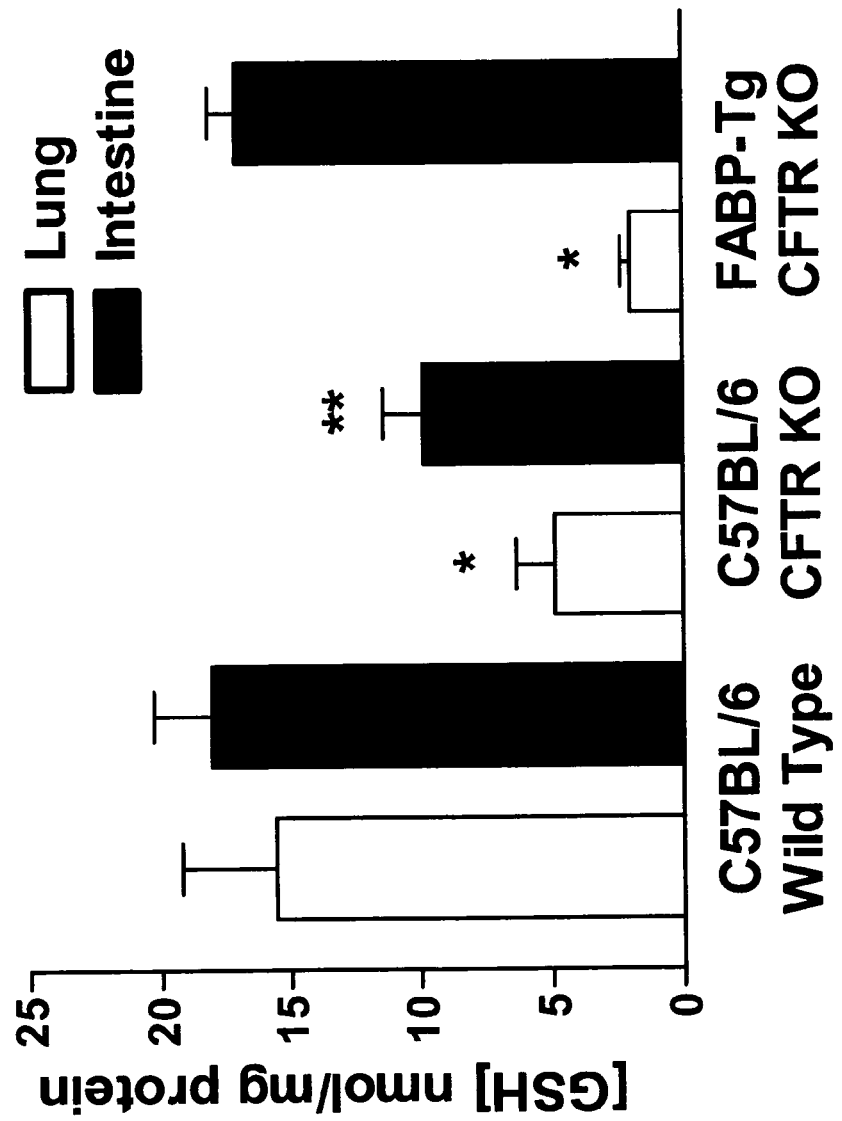
FIG. 11 represents lung and intestinal mitochondrial GSH in control versus CFTR KO mice.

FIG. 11 Mitochondrial Glutathione (GSH) Concentrations in the Lung and Small Intestine of Wild Type and Cystic Fibrosis Transmembrane Regulator Protein Knockout (CFTR-KO) Mice. Mitochondria were isolated from homogenized lung and small intestine by differential centrifugation. Briefly, lungs and small intestines were homogenized in mitochondrial isolation buffer (210 mM mannitol, 70 mM sucrose, 5 mM Tris-HCl, 1 mM EDTA, pH 7.5) and cellular debris removed by repeated centrifugations at 1,300×g until no pellet was obtained. The supernatant was then centrifuged at 17,000×g to pellet mitochondria. Isolated mitochondria were then resuspended in phosphate-buffered saline and protein concentrations determine. Mitochondria were lysed by the addition of metaphosphoric acid (final concentration of 1%) and precipitated proteins pelleted by centrifugation at 20,000×g. GSH concentrations were determined by HPLC coupled with electrochemical detection and normalized to the protein concentration. The wild type mice (C57BL/6) have functional CFTR in both the lungs and intestinal tract. The C57BL/6 CFTR-KO mice do not have functional CFTR in either the lungs or the intestinal tract. In the FABP-Tg CFTR-KO mice, a functional CFTR protein has been restored to the intestinal tract. Mitochondrial GSH concentrations in the lungs of both the CFTR-KO lines were significantly lower than wild type mice. In the small intestine of the C57BL/6 CFTR-KO mice, mitochondrial GSH concentrations were significantly lower than the wild type mice. In the FABP-Tg CFTR-KO mice where intestinal expression of CFTR has been restored, mitochondrial GSH concentrations were not significantly different than wild type mice. Lung mitochondrial GSH concentrations in the FABP-Tg CFTR-KO mice, however, still remained significantly lower. Data are shown as the mean±standard error for $n \geq 6$ and significance from wild type (*) lung and (**) intestine attained at $p \leq 0.05$.

Example 8

Figure 12:
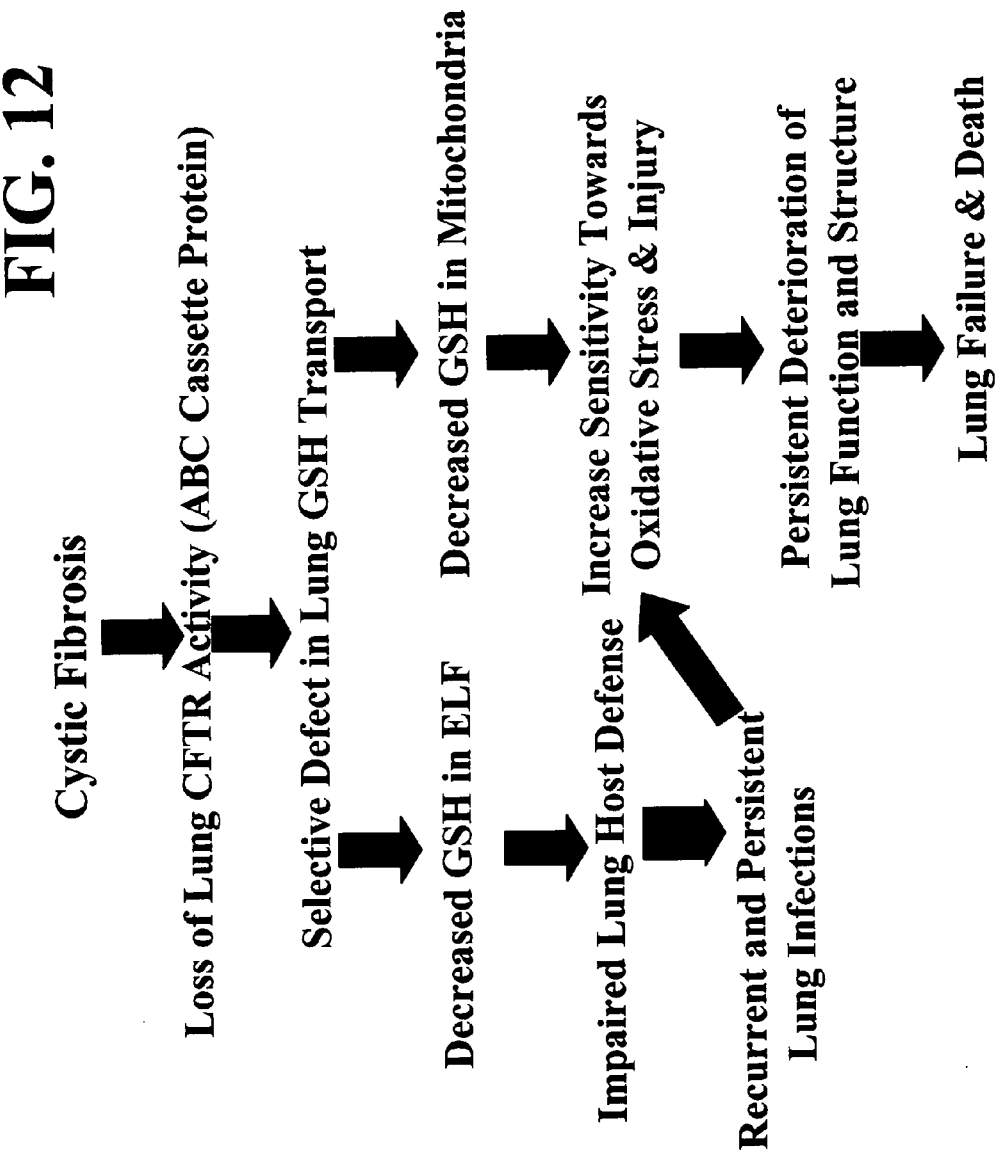
FIG. 12 represents a schematic of cystic fibrosis and the effects of GSH in the progression to lung failure.

FIG. 12 Defective Cystic Fibrosis Transmembrane Regulator (CFTR) Protein and Potential Pathways to Lung Disease. Defective CFTR activity in the lung results in decreased GSH transport in the lung. Across the epithelial surface, decreased GSH transport via CFTR will produce a concomitant decrease in the concentration of GSH in the epithelial lining fluid (ELF) that covers the airspace surface. In addition, defective CFTR produces a decrease in mitochondrial GSH concentrations. Whether this consequence is due to a direct CFTR effect on mitochondrial GSH transport or through a secondary pathway is unclear. The decrease in ELF GSH concentrations may impair lung defense mechanisms and permit persistent and recurring lung infections. Mitochondrial oxidative stress, primarily through superoxide leaking from oxidative phosphorylation, is increased because GSH concentrations are decreased. Taken together, defective GSH transport from the CFTR mutation may initiate the oxidative stress from the chronic infections and mitochondria that produces a progressive deterioration of the lung structure and function resulting in pulmonary failure and death.

Example 9

Figure 14:
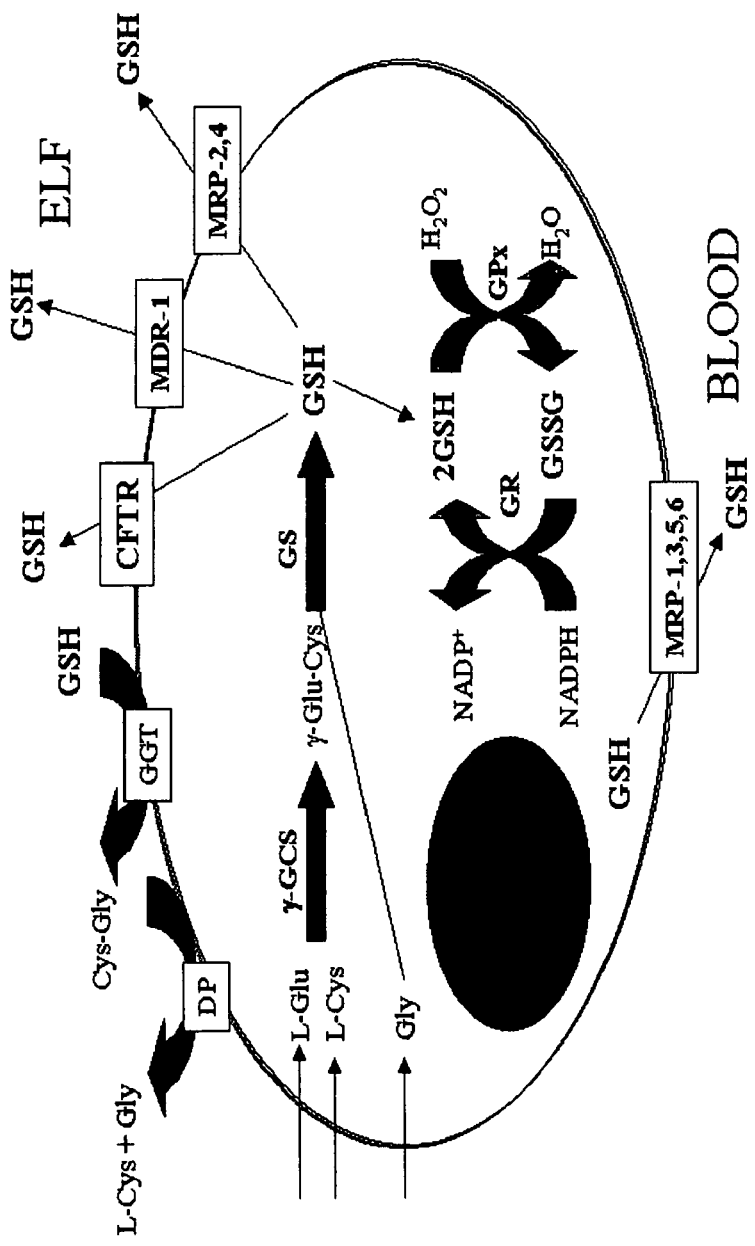
FIG. 14 represents a schematic of cellular synthesis, metabolism and transport of GSH.

FIG. 14—Cellular Synthesis, Metabolism and Transport of Glutathione (GSH). GSH is synthesized from its constituent amino acids (L-Glu, L-Cys, and L-Gly) by the sequential action of γ-glutamylcysteine synthetase (γGCS) and GSH synthetase (GS). Steady state GSH levels reflect a balance between synthesis, consumption and transport. GSH can reduce deleterious peroxides by action of glutathione peroxidase (GPx) to generate oxidized glutathione (GSSG). Once oxidized, GSSG can be reduced back to GSH by glutathione reductase that derives its reducing equivalents from NADPH. Certain members of the ABC transporter family can transport GSH across the cell membrane. In the apical membrane of a pulmonary epithelial cell, these transporters may include the cystic fibrosis transmembrane regulator protein (CFTR) and multidrug resistance proteins 2 and 4 (MRP2 and MRP4 respectively). CFTR, and potentially the MRP proteins, play an important role in the maintenance of epithelial lining fluid (ELF) GSH concentrations. ELF GSH can be recycled by the coordinated activity of γ-glutamyltransferase (GGT) and dipeptidase (DP) that cleave GSH into its amino acid constituents and transfer them into the cytoplasm.

Example 10

Figure 15:
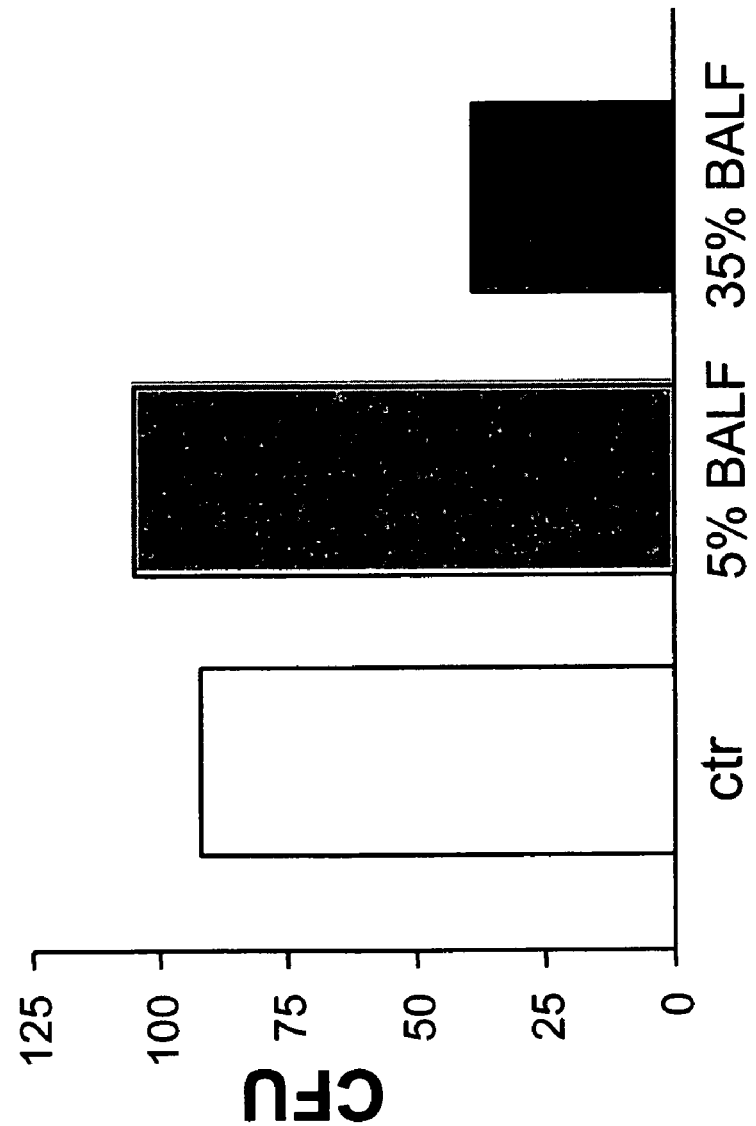
FIG. 15. represents *Pseudomonas* killing by an eight-hour exposure to mouse bronchoalveolar lavage fluid (BALF)

FIG. 15—*Pseudomonas* Killing by an Eight-Hour Exposure to Mouse Bronchoalveolar Lavage Fluid (BALF). *Pseudomonas aeruginosa* was cultured in the presence of increasing concentrations of BALF for 8 hours and pseudomonas viability then determined by Colony Forming Units (CFU) on agar plates. BALF was obtained through a tracheal canula. Two separate 1 mL aliquots of phosphate-buffered saline (PBS; pH 7.4) were instilled into the lung and withdrawn. The aliquots were then pooled and centrifuged at 4000×g to remove cells (i.e., alveolar macrophages). Bacteria were then exposed to PBS control (ctr), 5%, or 25% dilution of BALF for 8 hours. Following the exposure, bacteria were then cultured and the number of CFU determined. The greater the antibacterial properties of the exposure condition the less CFUs. Exposure of pseudomonas to 25% BALF greatly decreased (≈50%) the number of pseudomonas CFU. This demonstrates that BALF contains antibacterial modulators.

Example 11

FIG. 16 Extracellular Concentration of Glutathione (GSH) from Rutin and Dexamethasone Treated Cells. Cells were treated with various concentrations of rutin or dexamethasone for 48 hours and then the GSH concentration in the media determined. Cells, CFTR-deficient CRL-1687 cells, were grown to approximately 90% confluency in 24-well plates and then exposed to media containing the varying concentrations of rutin or dexamethasone. At 48 hours the media was removed and GSH concentrations determined by HPLC coupled with electrochemical detection and normalized to the protein concentration.

Example 12

Figure 17:
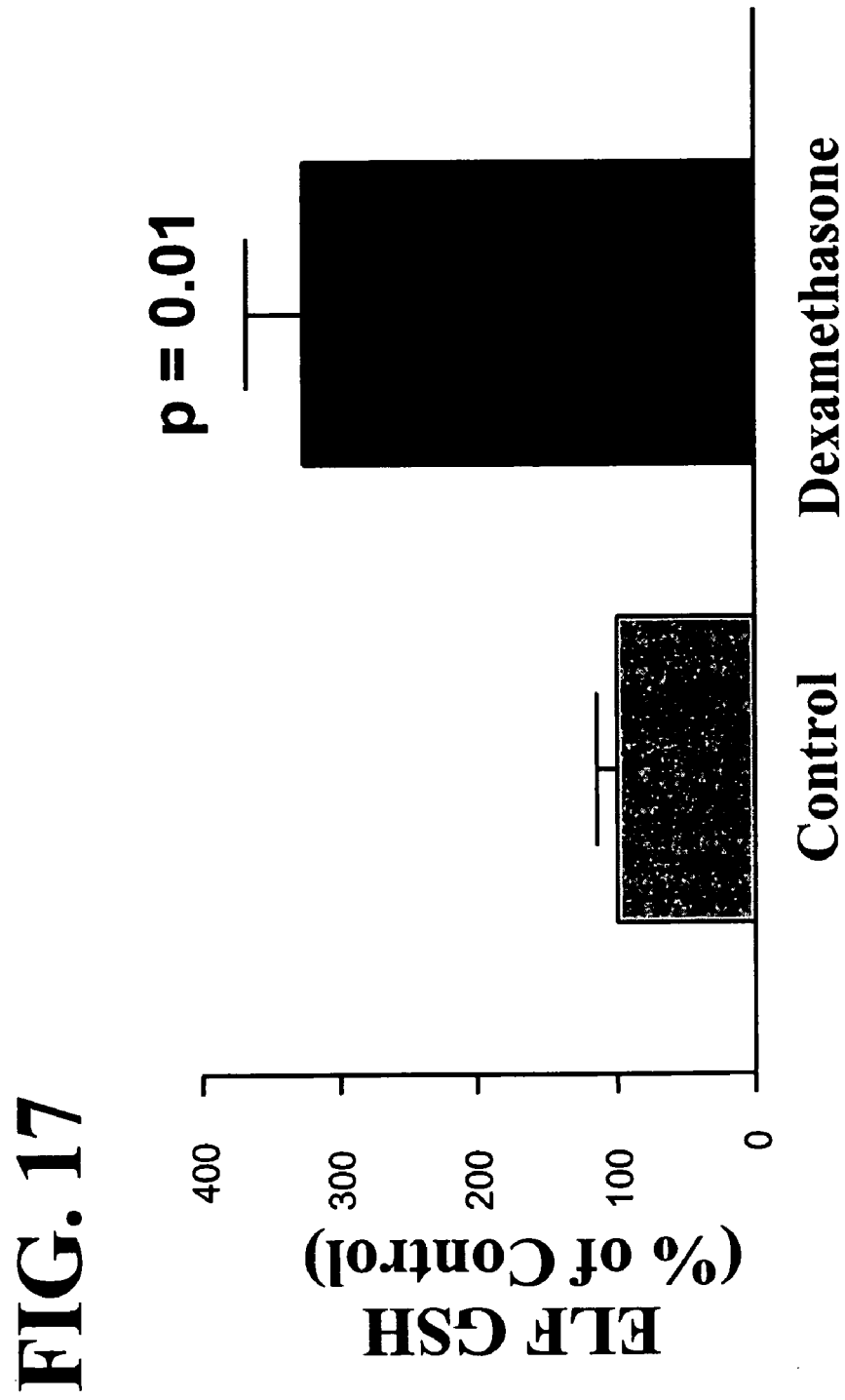
FIG. 17 represents the levels of lung ELF GSH in control versus Dexamethasone treated mice.

FIG. 17 Dexamethasone-Induced Changes in Epithelial Lining Fluid (ELF) Glutathione (GSH) Concentrations. Wild type (C57/B6) mice were given a 1 mg/kg dexamethasone (DEX) injection (intraperitoneal) daily for two days. Bronchoalveolar lavage fluid (BALF) was obtained at 48 hours after the first initial dose and GSH concentrations determined. BALF was obtained through a tracheal canula with a single 2.0 mL aliquots of phosphate-buffered saline (pH 7.4) that was instilled into the lung and withdrawn only once. The BALF was centrifuged at 4000×g to remove cells (i.e., alveolar macrophages). The cell-free BALF was acidified with metaphosphoric acid to a final concentration of 1% metaphosphoric acid and centrifuged at 20,000×g to pellet the precipitated proteins. GSH concentrations were determined by HPLC coupled with electrochemical detection. ELF concentrations of GSH were calculated from BALF concentrations multiplied by a dilution factor derived from the difference in serum and BALF urea concentrations. ELF concentrations in DEX treated mice were significantly increased (75.3±12.0 μM) compared to untreated mice (18.9±2.3 μM). Data are shown as the mean±standard error for n≧4 with significance attained at p≦0.05.

Example 13

Figure 18:
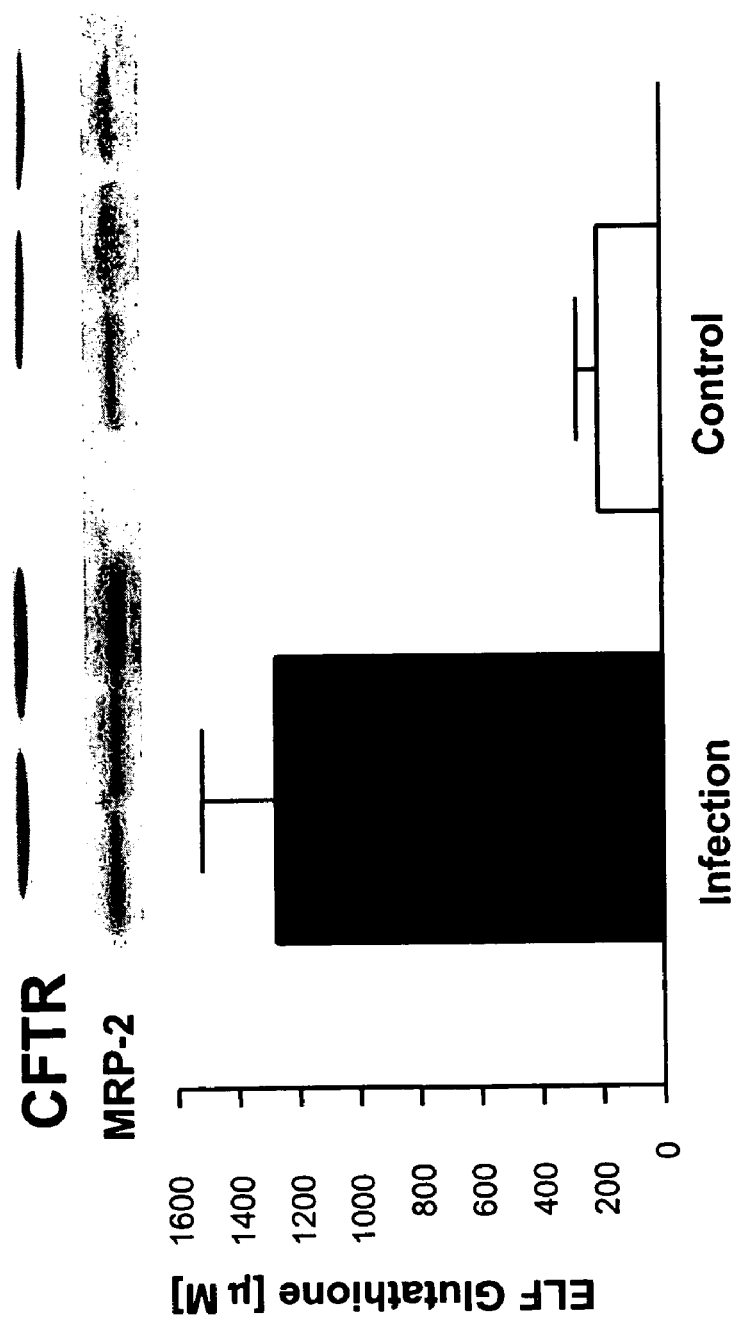
FIG. 18 represents the effect of *Pseudomonas* endobronchial infection on lung ELF GSH levels and induction of lung MRP2 transporter and CFTR expression.

FIG. 18 Epithelial Lining Fluid (ELF) Glutathione (GSH) Concentrations and Lung MRP2 and CFTR Expression in *Pseudomonas* Infected Wild Type Mice. Wild type (C57/B6) mice were infected with *Pseudomonas aeruginosa* via intratracheal instillation of *Pseudomonas*-coated particles. Forty-eight hours following the inoculation, bronchoalveolar lavage fluid (BALF) and lung tissue were harvested. ELF concentrations of GSH were calculated from BALF concentrations multiplied by a dilution factor derived from the difference in serum and BALF urea concentrations. Lungs were lavaged through a tracheal canula with three separate 1 mL aliquots of phosphate-buffered saline (pH 7.4). Each aliquot was instilled into the lung and withdrawn only once. All three aliquots were then pooled and centrifuged at 4000×g to remove cells (i.e., alveolar macrophages). The cell-free BALF was acidified with metaphosphoric acid to a final concentration of 0.75% metaphosphoric acid and centrifuged at 20,000×g to pellet the precipitated proteins. GSH concentrations were determined spectrophotometrically with a commercially available assay that forms a chromogen with GSH. Lungs from *Pseudomonas* infected mice were homogenized in membrane isolation buffer (250 mM sucrose, 10 mM Tris-HCl, pH 7.5; MIB) and filtered through silk to remove large debris. Homogenate was then centrifuged at 33,000×g to pellet membranes. Membranes were resuspended in MIB for Western blotting. Membrane proteins (30 μg) were separated on 8% agarose gels, transferred to PVDF membranes for determination of MRP2 and CFTR expression. GSH concentrations in the ELF of pseudomonas infected mice (1282±238 μM) were significantly elevated compared to uninfected control mice (201±75 μM). Data are shown as the mean±standard error for n=5 with significance attained at p≦0.05. Western blots demonstrate an increase in the expression of both MRP2 and CFTR in pseudomonas infected lungs compared to uninfected mice.

Example 14

Table 4. Flavonoid-mediated modulation of intracellular GSH levels. In one exemplary experiment, modulation of intracellular GSH levels by a number of flavonoids and other compounds in A549, HL-60 and PC-3 cells after 24 hours of treatment is represented in Table 4. Some of the more effective compounds examined for inducing depletion of intracellular GSH were analyzed in A549 and HL-60 cells, and the results from A549 cells are represented in Table 5. In one example, using chrysin as an inducer of thiol-containing compound transport, 50% depletion of intracellular GSH required 25 μM of chrysin and 2 hours of treatment in A549 cells, 24 hours using the same concentration in PC-3 cells, and 50 μM of chrysin and 24 hours in HL-60 cells.

Figure 19:
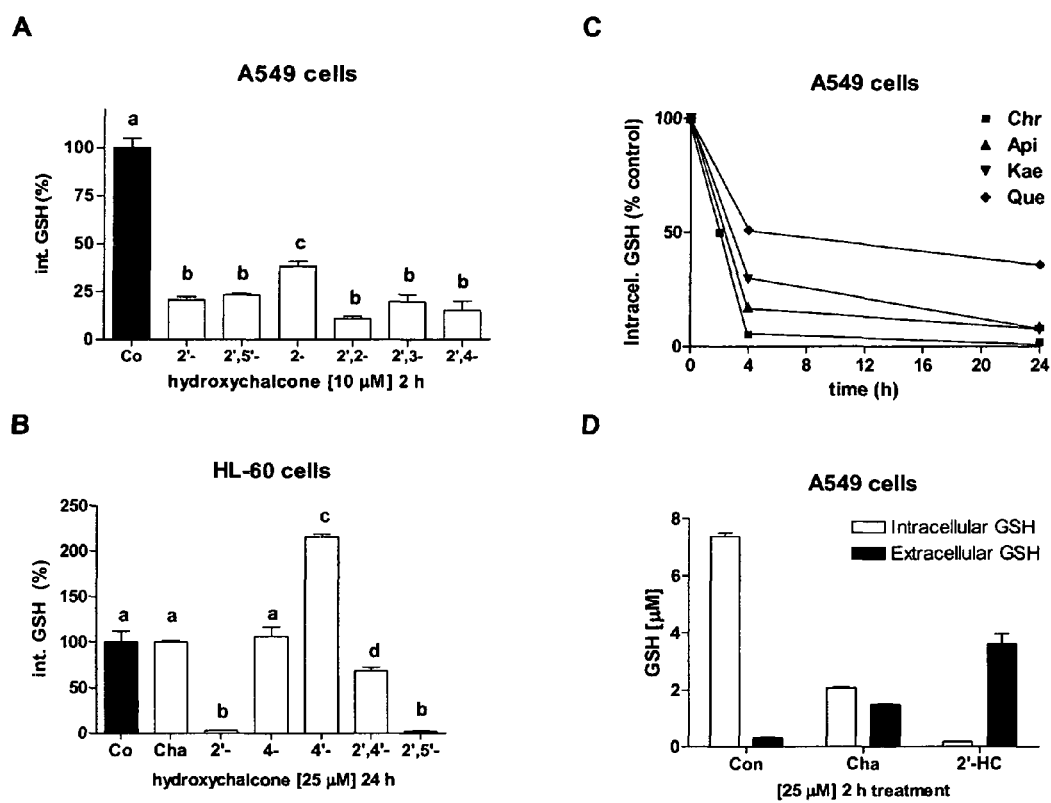
FIG. 19A-19D. represents an example of depletion of intracellular GSH levels induced by flavonoids as measured by HPLC-EC. 19A, induced by hydroxychalcones; 19B. induced by hydroxychalcones in; HL-60 cells. 19C, induced by hydroxychalcones in A549 cells, 19D, intracellular and extracellular GSH in A549 cells with combination treatment.

In one exemplary method, the cell response to hydroxychalcones (HCs) and dihydroxychalcones (DHCs) was much higher in A549 and HL-60 cells (Table 4). 2'-HC, and 2',2-, 2',4-2',3- and 2',5'-DHC demonstrated effective HCs for depleting intracellular GSH in A549 and HL-60 cells. In A549 cells, 2 hours of exposure to 10 μM of these compounds resulted in 75 to 90% GSH depletion (FIG. 19A), and in HL-60 cells, 25 μM and 4 hours resulted in 55 to 70% depletion (data not shown). A similar effect was also noted in hepatocytes using higher amounts of HCs (over 100 μM and 2 hours of treatment), and that 2',3',4'-trihydroxychalcone was more effective. One example suggests that a chalcone pharmacaphore may be more active if it contains at least one hydroxyl group where the hydroxyl is in the 2'-position. The lack of hydroxyl groups (chalcone) or the presence of more than two hydroxyl groups appeared to lessen this effect in the three cell types (Tables 4 and 5). In one exemplary method, a hydroxyl group in position 4' of a chalcone markedly decreased the effect in A549 cells (Table 4) an increase in intracellular GSH levels in HL-60 and PC-3 cells (215% and 164% compared to control, respectively, using 25 μM of 4'-HC and 24 hours of treatment) (FIG. 19B).

In one exemplary method, chrysin was one active flavone-like structure for inducing GSH depletion in A549 and HL-60 cells, whereas in PC-3 cells, apigenin was one active flavone-like structure for inducing GSH depletion (Table 4). 7-Hydroxyflavone (7-HF) was almost as effective as chrysin, whereas 5-hydroxyflavone (5-HF) was less effective here, 7-Methoxyflavone (7-MF) was less effective than 7-HF but more effective than flavone (Table 5). Some of these examples suggest that an active flavone pharmacophore contains at least one hydroxyl group in the 7 position. Under some conditions, the cell response to hydroxyflavones (HFs) was generally lowered by: 1) the addition of hydroxyl groups; 2) the loss of the ketone group in position 4 (catechins or cyanidins); 3) the loss of the double bond in position 2-3 (flavanones); and 4) O-glycosylation as shown with rutin (Tables 4 and 5, FIG. 19C).

In another exemplary method, Resveratrol, a natural polyphenol that has structural similarities with flavonoids, and cancer preventative activity associated with mitochondrial-mediated apoptosis was analysed, and found effective in HL-60 cells (Table 4).

In another example, hydroxychalcones were found to be effective and in some cases more effective than MRP1 substrates MK-571, indomethacin and verapamil in A549 and HL-60 cells (Tables 4 and 5). Chrysin and 7-hydroxyflavone were effective in this example more than MK-571 in A549 cells. In PC-3 cells, apigenin as another anti-cancer agent was more effective than MK-571, and chrysin than indomethacin and verapamil (Table 4). Overall, in the three tumor cell types, at least one flavonoid was more effective for inducing intracellular GSH depletion than the three MRP1 substrates tested.

In order to verify that the GSH depletion induced by HCs in A549 cells was due to GSH efflux, extracellular GSH levels in A549 cells after 2 hours of treatment with chalcone and 2'-hydroxychalcone (25 μM) were measured, and the results showed increased levels of GSH in the supernatants (FIG. 19D). In other exemplary experiments, other compounds had differential effects on cellular GSH levels within the three tumor cell types. For example, morin, cyanidin and (−)-epicatechin (50-75 μM) stimulated an increase in intracellular GSH in PC-3 cells, but not in A549 or HL-60 cells. Curcumin also markedly increased intracellular GSH levels in HL-60 and PC-3 cells (Table 4).

Oxidative Stress, GSH Depletion and Potentiation of Tumor Cell Cytotoxicity

GSH depletion by itself is not a major cause of cytotoxicity. Chrysin, for instance, was a very potent inducer of intracellular GSH depletion in A549 cells but showed relatively low toxicity after 48 hours of treatment. Apigenin and genistein, which were reported to be effective inhibitors of complex I of the mitochondrial respiratory chain, were relatively toxic in the three cell types, whereas kaempferol was not an inhibitor of complex I and was less toxic (Table 4). However, the contribution of MRP-mediated GSH depletion to the toxicity of flavonoids and other pro-oxidants cannot be discarded. For instance, rotenone, etoposide and fisetin were relatively effective for depleting GSH as well as toxic in HL-60 cells (Table 4). Hydroxychalcones were markedly more toxic than hydroxyflavones in the three tumor cell types, although this effect did not necessarily rely on GSH efflux, since they induced little or no GSH depletion in PC-3 cells (Table 4).

Example 15

Figure 20:
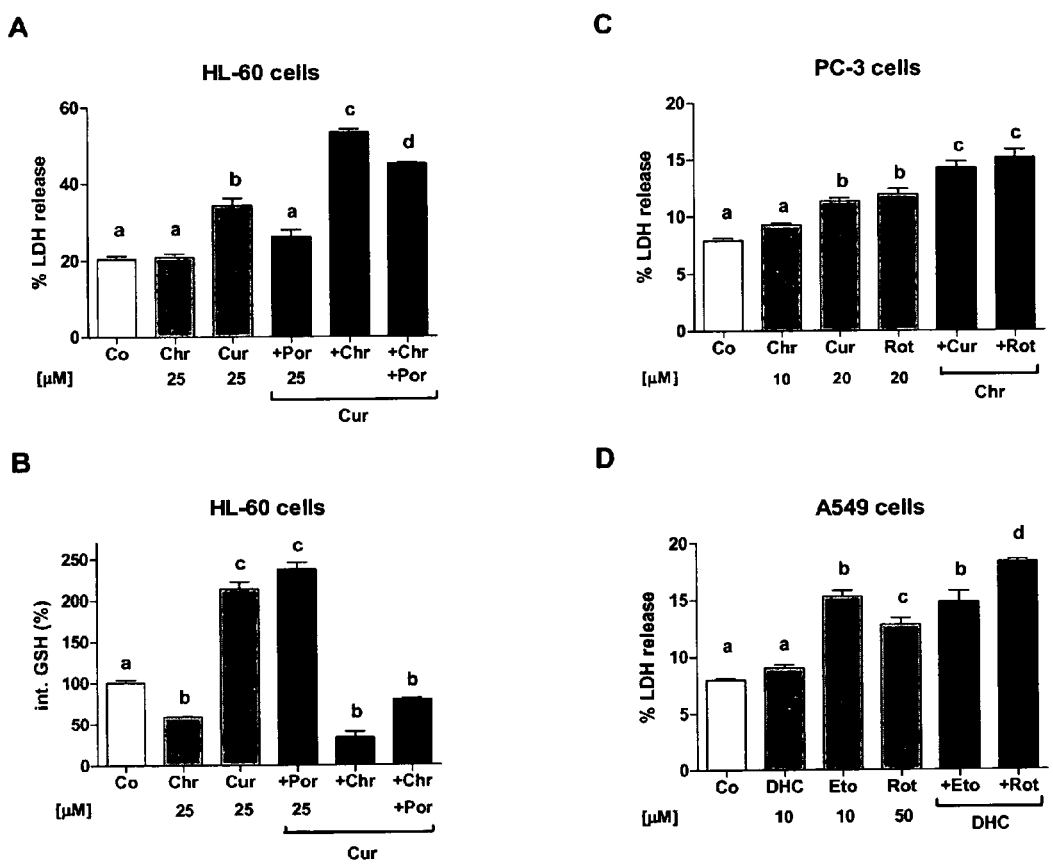
FIG. 20A-20D. represents an example of compounds that can induce GSH depletion in combination with pro-oxidant agents. 20A, represents percentage of LDH release as an index of cytotoxicity in treated HL-60 cells, 20B, represents intracellular GSH levels in treated in treated HL-60 cells 20C, represents percentage of LDH release as an index of cytotoxicity in PC-3 cells, 20D represents percentage of LDH release as an index of cytotoxicity in treated in A549 cells.

In one exemplary experiment, the abilities of 2',5'-dihydroxychalcones and chrysin to potentiate the toxicities of etoposide, rotenone, curcumin and 2-ME were examined in A549, HL-60 and PC-3 cells after 48 hours of treatment. Although curcumin-glutathione adducts have been reported to be substrates of MRP1 and MRP2, curcumin produced an accumulation of intracellular GSH in HL-60 and PC-3 cells, thus making it a valuable tool to study the effects of inducers of GSH depletion (Table 4). Chrysin (25 μM) potentiated the toxicity of curcumin (25 μM) in HL-60 cells, whereas this toxicity was attenuated by MnTE-2-PyP (25 μM) (FIG. 20A). When measuring intracellular GSH levels, chrysin also induced GSH depletion in presence of curcumin (FIG. 20B). PC-3 cells were particularly sensitive to curcumin-induced toxicity, which was also potentiated by chrysin (FIG. 20C). The combination of curcumin and chrysin resulted in GSH depletion in PC-3 cells as well (data not shown). Apigenin also potentiated the curcumin's toxicity, but unexpectedly less than chrysin. Chrysin (10-20 μM) also potentiated the toxicities of rotenone (20 μM), 2-ME (50 μM) and etoposide (40 μM) in PC-3 cells. In A549 cells, 2',5'-DHC (10 μM) potentiated the toxicities of rotenone (50 μM), curcumin (50 μM) and 2-ME (50 μM), but not of etoposide (10 □M) (FIG. 20D). Chrysin also failed to potentiate etoposide's toxicity in this cell type. HCs (2 μM) did not potentiate pro-oxidant toxicities in HL-60 cells, probably because of their intrinsic toxicity in this cell type.

In one exemplary method, the production of superoxide ($O_2^-$) in the presence of curcumin, MnTE-2-PyP or chrysin was analyzed using flow cytometry. The compounds and cells were chosen since curcumin may not induce intracellular GSH depletion in HL-60 cells, and that chrysin was not very toxic and proven effective for potentiating the toxicity of curcumin (FIGS. 20A and 20B). Curcumin (10 μM) produced a significant elevation in $O_2^-$ production within one hour of treatment (FIG. 21A). Such an early event was previously observed with 2-ME in HL-60 cells and shown to trigger the apoptotic cascade of events. $O_2^-$ levels induced by curcumin gradually decreased over time (FIG. 21B). When cells were pre-treated with MnTE-2-PyP (30 μM) for 2 hours, lower levels of $O_2^-$ were detected (FIG. 21B), which one mode of action for curcumin includes its ability to stimulate increased levels of $O_2^-$. Chrysin was also reported to inhibit complex I of the mitochondrial respiratory chain, yet, at 25 μM, it induced little change in $O_2^-$ levels and was not toxic (FIGS. 20A and 21B). If the potentiation effect of chrysin were due to inhibition of curcumin efflux, higher levels of $O_2^-$ would be expected from adding chrysin to curcumin treatment. However, no increase of $O_2^-$ levels was observed, but rather a decrease after 4 hours (FIG. 21B) demonstrating that the potentiation effect was not mediated by $O_2^-$ implying other mechanistic activities might be occurring.

Techniques Used in Experimentation

Serum and BALF Urea Concentrations. To determine actual ELF concentrations of soluble antioxidants from BALF, a dilution factor is derived from the difference between BALF and serum urea concentrations. The assumption that urea freely diffuses between the vascular and ELF compartments are used as an indicator of ELF dilution. (Rennard, S. I. Estimation of volume of epithelial lining fluid recovered by lavage using urea as a marker of dilution, J. of Applied Physiol. 1986 vol. 60 532-550). A dilution factor is thereby obtained by dividing the serum urea concentration by the BALF concentration. ELF concentrations are then calculated by multiplying the BALF concentrations by the dilution factor. Urea concentrations in the samples are determined using a commercially available reagent (Sigma Diagnostics 66-20; St. Louis, Mo.).

Western Blot. Lung apoprotein levels of CFTR, MRP-2 and MDR-1 may be determined by western blot analysis. Frozen and fresh lung tissue will be homogenized and 10-30 μg of protein separated by SDS-PAGE (8% acrylamide gels) on a mini protean-3 electrophoresis system at 100 V. Proteins will be transferred onto PVDF membrane and blocked overnight at 4° C. with 5% horse serum in Tris balanced salt solution with tween-20 (TBS-T). Proteins will be identified using commercial antibodies against CFTR (monoclonal 24-1, R&D Systems), MRP-2 (monoclonal $M_2$ III-6, Alexis) and MDR-1 (monoclonal 265/F4, NeoMarkers) as primary antibodies that are incubated at room temperature for 2-3 hours, washed extensively with TBS-T and then incubated with the appropriate secondary rabbit antimouse or other antibody conjugated with HRP for 30 minutes at room temperature. Blots are then extensively washed with TBS-T and developed with an ECL chemiluminescence kit (Amersham) and captured on X-ray film. Densitometry is performed with a gel imaging system (CDD Bio, Hitachi).

RT-PCR Analysis. RT-PCR will be performed using Advantage one-step kit with a RT-PCR control amplimer set containing mouse G3PDH (Clontech). The primer sequences for the mouse MDR1 gene (5'-CTCACCAAGCGACTC-CGATACATG-3' (SEQ ID NO:1); 5'-GATAATTCCTGTGC-CAAGGTTTGCTAC-3') (SEQ ID NO:2)) and (5'- AAGAC AAAGATTCTAGTGTTGGACG-3') (SEQ ID NO:3); (5'- AGATATGCCAGAGATCAGTTC ACACC-3') (SEQ ID NO:4) for the MRP-2 gene will be used as described. RT-PCR products are visualized by UV illumination after electrophoresis through 2% agarose gels and documented using the gel imaging system (CCD Bio, Hitachi).

Immunocytochemistry. An immunoperoxidase method (Oury et. al 1994. "Immunocytochemical localization of extracellular superoxide dismutase in human lung". Lab Invest. 70:889-898) will be used for light microscopic immunocytochemical labeling. Tissue nonspecific binding to antibodies is blocked by incubation with 5% normal goat serum, 5% gelatin and 1% BSA. Sections are then incubated with either the pre-immune serum or the primary antibody against either MRP-2 or MDR-1 in 0.1% gelatin and 1% BSA in PBS for 1 hour at room temperature. They are washed and incubated with biotin labeled rabbit anti-mouse diluted in 0.1% gelatin and 1% BSA for 1 hour. The labeling signals are intensified by incubation with streptavidin conjugated to horseradish peroxidase in 0.1% gelatin+1% BSA. Labeling is detected by incubating in diaminobenzidine (10 mg diaminobenzine, 50 ml 0.05 M Tris Cl, pH 7.6, 100 µl 3% $H_2O_2$). After the incubation, slides are counter stained with 1% methyl green, washed, dehydrated in ethanol, cleared with xylene and mounted in flowtek.

Aconitase Activity. Aconitase inactivation is a sensitive marker for superoxide or peroxynitrite formation in the mitochondria. Aconitase activity is measured spectrophotometrically by monitoring the formation of cis-aconitate from isocitrate at 240 nm as previously described by Patel et. al. 1996 "Requirement for superoxide in excitotoxic cell death. Neuron 16:345-355)

F2-Isoprostane Formation. The formation of F2-isoprostanes will be measured by GC/MS (gas chromatography/mass spectroscopy) as previously described. Briefly, F2-isoprostanes will be extracted from tissue with chloroform/methanol (2:1, v/v) containing 0.005% butylated hydroxytoluene and the organic phase evaporated to dryness under vacuum. The F2-isoprostanes will be released from the lipids by hydrolysis in 4 ml methanol plus 4 ml KOH (15%) at 37° C. for 30 minutes. The free isoprostanes are derivatized with N,O-bis(trimethylsilyl)trifluoroacetamide and F2-isoprostanes quantified by gas chromatography/negative ion chemical ionization mass spectrometry (GC/NICI-MS) using [$^2H_4$]-PGF2a (Cayman Chemical, Ann Arbor, Mich.) as an internal standard.

HPLC Analysis for 8-Hydroxy-2-Deoxyguanosine in Lung DNA: DNA from mouse lung tissue was obtained by a chloroform/isoamyl alcohol extraction of proteinase K digested lung homogenates. The purified DNA was then hydrolyzed to nucleosides with nuclease P1 and alkaline phosphatase. Samples were analyzed for 8-hydroxy-2-deoxyguanosine (8OH2dG) and 2-deoxyguanosine (2dG) by HPLC coupled with coulometric electrochemical and UV detection (CoulArray Model 5600; ESA Inc., Chelmford, Mass.) for 8OH2dG and 2dG respectively. Sample analysis was done using a 4.6×150 mm, C-18 reverse phase column (YMCbasic®; YMC Inc., Wilmington, N.C.) with a mobile phase of 100 mM sodium acetate in 5% methanol at pH 5.2. UV detects 2dG at 265 nm while 8OH2dG was detected electrochemically with electrode potentials of 285, 365 and 435 mV. Under these conditions, 2dG and 8OH2dG had retention times of approximately 7.4 and 9.5 minutes respectively. Nucleoside concentrations were calculated from standard curves generated daily with freshly prepared standards.

*Pseudomonas* killing assay. This assay was derived from an assay used to study bacterial killing by neutrophils (Hampton, M. B. 1999 "Methods for quantifying phagocytosis and bacterial killing by human neutrophils" J. Immunol. Methods 232:15-22). Inoculums of *Pseudomonas aeruginosa* (PA01) are grown in LB media in the presence or absence of mouse BALF and viability assessed at various time points (usually 4 to 8 hours). Mice are anesthetized with pentobarbital followed by exsanguinations by direct cardiac puncture.

Approximately 1 ml of blood is collected in heparinized tubes and plasma prepared by centrifugation and stored at −80° C. until use. BALF was collected using one 1-mL aliquot of sterile phosphate buffered, pH 7.4 (PB). The aliquot is centrifuged (2000×g for 5 minutes at 4° C.) to recover cells. An aliquot of the cell free BALF supernatant is acidified with 5% m-phosphoric acid and the supernatant retained and stored at −70° C. for subsequent analyses. The remaining cell free BALF is used for testing in its effect in host defense in the *Pseudomonas* growth inhibition assay. The right and left lungs are then removed and either quick-frozen in liquid nitrogen or fixed for immunocytochemistry.

To minimize GSH loss during the evaluation, BALF is acidified with 5% m-phosphoric acid (150 µL/mL), cooled on ice and centrifuged (10,000×g for 10 min. at 4° C.) to remove precipitated proteins. The lung tissue, approximately 20 mg of the ground tissue is dissolved in 600 µL of PBS, acidified with 50 µL of 5% m-phosphoric acid, cooled on ice, and centrifuged (10,000×g for 10 min. at 4° C.) to remove precipitated proteins. GSH and GSSG in BALF and tissues are analyzed by HPLC coupled with coulometric electrochemical detection (CoulArray Model 5600; ESA Inc., Chelmford, Mass.). Sample analysis was done using a 7×53 mm C-18 reverse phase (Platinum EPS C18 100A 3 µm, Alltech Associates Inc., Deerfield, Ill.) and a mobile phase of 125 mM potassium acetate in 1% acetonitrile at pH of 3.0. The electrode potentials in a four-channel electrode array were set at 100, 215, 485 and 570 mV. Under these conditions, GSH exhibited a retention time of 2.7 minutes with a signal distributed across channels 2, 3 and 4; GSSG exhibited a retention time of 4.2 minutes with a signal confined to channel 4. Concentrations of GSH and GSSG from a 10 µL injection can be determined from a five-point calibration curve generated from standards prepared fresh daily.

Bacterial viability is assessed by the loss of ability of bacteria to form colonies after plating on nutrient agar. In preliminary studies it was determined that a 1:2,000,000 dilution of the culture plated on agar overnight gives a good number of CFUs (colony forming units) with the PA01 strain (see preliminary data). To control for dilutional effects of the BALF we control with the same % of PBS. This assay provides us with a functional endpoint to assess changes in host defense of the BALF.

Cytokine Analyses. Levels of TNF-α, MIP-2 and IL-10 will be measured on 50 μl BALF using commercial ELISA kits (MTAOO, MM200 & M100, R&D Systems, Minneapolis, Minn.). These cytokines are surrogate markers of inflammation. TNF-α and MIP-2 serve as pro-inflammatory cytokine markers and IL-10 serves as an anti-inflammatory cytokine marker. These markers are either elevated (TNF-α, MIP-2) or depressed (IL-10) in CF BALF.

Histopathology. Mice from each group will be used for histopathology. Mice will be anesthetized with avertin and their trachea cannulated and instilled with 2% paraformaldehyde plus 2% glutaraldehyde in 0.1 M phosphate buffer, pH 7.4. After 10 minutes of fixation within the chest cavity, lungs are removed and 2 mm slices are cut and immersion fixed in 4% paraformaldehyde for overnight fixation and embedded in parafilm. For electron microscopy, 2 mm slices are placed in 2% glutaraldehyde for four hours then cubed into 2×2×2 blocks and washed in cacodylate buffer and post-fixed with 2% $OsO_4$. The blocks are dehydrated in a graded series of ethanol, transferred to propylene oxide, and embedded in Epox. A diamond knife is used to cut thin sections and placed on a 200 mesh uncoated grid. Sections are stained with uranyl acetate and lead citrate prior to viewing. Sections will be viewed for both extent and severity of tissue injury and inflammatory cell infiltration.

Materials and Methods

Chemicals. Chalcone, 2-, 2'-, 4- and 4'-hydroxychalcones, 2',2-, 2',3-, 2',4-, 2',4'- and 2',5'-dihydroxychalcones, 2',4',4- and 2',3',4'-trihydroxychalcones, flavone, 5-hydroxyflavone, 7-hydroxyflavone, 7-methoxyflavone and galangin may be purchased from Indofine Chemicals Company, Inc. (Hillsborough, N.J.). Chrysin, apigenin, kaempferol, quercetin, genistein, biochanin A, 4',5,7-trihydroxyflavanone (naringenin), baicalein, fisetin, morin, myricetin, (−)-epicatechin, rutin, resveratrol, 2-methoxyestradiol, 2-hydroxyestradiol, β-estradiol, curcumin, rotenone, etoposide, (±)-verapamil, indomethacin, digitonin, pyruvate (sodium salt), phosphoric acid, meta-phosphoric acid, sodium phosphate (monobasic), Triton X-100, phenylmethylsulfonyl fluoride (PMSF), EDTA, NADH, $K_2HPO_4$, $KH_2PO_4$, HEPES, DMSO and DMF may be from Sigma-Aldrich (St. Louis, Mo.). Tris-HCl, perchloric acid, and methanol from Fisher (Pittsburgh, Pa.). Dihydroethidium (hydroethidine) and 2',7'-dichlorofluorescin (DCF) from Molecular Probes (Eugene, Oreg.). MK-571 from Biomol (Plymouth Meeting, Pa.) and cyanidin from Extrasynthese (Genay, France). Phosphate-Buffered Saline (PBS) from from Cellgro (Herndon, Va.). Monobromobimane (mBBr) from Calbiochem (San Diego, Calif.). (Des-Gly)-glutathione (reduced, ammonium salt) may be purchased from Bachem (Torrance, Calif.). Protease inhibitor cocktail tablets supplemented with EDTA were from Roche Diagnostics (Indianapolis, Ind.). Manganese(III) meso-tetrakis(N-ethylpyridinium-2-yl)porphyrin (MnTE-2-PyP) was prepared as described previously (38).

Cell lines and culture conditions. Human lung epithelial cancer (A549), human leukemia HL-60 and human prostate (PC-3) tumor cells were purchased from ATCC (Manassas, Va.). A549 and PC-3 cells were grown in Ham's F12 medium (F12) and Kaighn's modification of Ham's F12 medium (F12K) with 2 mM L-glutamine (ATCC), respectively, supplemented with 10% fetal bovine serum (FBS) and 5% pen/strep (10,000 unit, Cellgro). HL-60 cells were grown in Iscove's modified Dulbecco's medium with 4 mM L-glutamine (ATCC) supplemented with 20% FBS and 5% pen/strep. Cell were grown in T-75 flask at 37° C. and 5% $CO_2$ air atmosphere and in 24-well plates for GSH levels and LDH release measurements.

Intracellular levels of GSH. Intracellular GSH levels can be determined by HPLC-EC. Cultured cells from 24-well plates were washed once with 1 ml of PBS and then re-suspended in 0.5 ml of distilled water with 40 μM of digitonin (2 mM stock solution in DMSO) for 30 min at room temperature. Then, 50 μl of 10% meta-phosphoric acid were added (1% final concentration), the samples were sonicated for 2 min, centrifuged at 20,000 g for 10 min, and 0.2 ml of supernatant placed in vials for HPLC analysis. The HPLC column used was Synergi 4u Hydro-RP 80A (150×4.6 mm) from Phenomenex (Torrance, Calif.) and the mobile phase a sodium phosphate buffer (125 mM sodium phosphate monobasic, pH adjusted to 3 with phosphoric acid) and 0.9% methanol. The flow rate was 0.5 ml·min$^-$. The retention time for GSH in these conditions was 7.5 min. The HPLC instrument was from ESA, Inc. (Chelmsford, Mass.), equipped with an autosampler (model 540) and a Coul array detector (model 5600A). The potential applied was +0.75 V vs. H/Pd electrode, and the injection volume 5 μl.

Extracellular levels of GSH. Extracellular GSH in the culture media supernatants of A549, HL-60 and PC-3 cells were measured by an HPLC-FD method of GSH analysis after derivatization with monobromobimane (mBBr). In one example, 90 μl of supernatant were mixed with 90 μl of KPBS buffer (50 mM potassium phosphate buffer, 17.5 mM EDTA, 50 mM serine, 50 mM boric acid, pH 7.4), 10 μl of reduced (des-Gly)-glutathione (0.1 mM stock solution) as internal standard and 10 μl of mBBr (5 mM stock solution in acetonitrile). The mixture was incubated in dark at room temperature for 30 min, and the reaction was stopped by addition of 10 μl of 70% perchloric acid. The samples were centrifuged at 16,000 g for 10 min and 0.18 ml of supernatant placed in vials for HPLC analysis. The HPLC column used was Synergi 4u Hydro-RP 80A ($C_{18}$) (150×4.6 mm) from Phenomenex (Torrance, Calif.) and the mobile phase a mixture of 1% acetic acid in $H_2O$ (pH adjusted to 4.25 using $NH_4OH$) with 7% acetonitrile. The flow rate was 1 ml·min$^{-1}$ and the injection volume 1 μl. The detector excitation and emission wavelengths were 390 and 480 μm, respectively. The retention time for the GSH derivative was 9.5 min.

Immunoblotting of MRP1. Membrane proteins were enriched as follows. Cells were centrifuged at 2000 g for 10 min and the cells re-suspended in buffer A (250 mM sucrose, 10 mM Tris base, pH 7.5, supplemented with protease inhibitor cocktail with EDTA). Cells were then homogenized and centrifuged at 500 g for 10 min. The supernatant was transferred in an ultracentrifuge tube and centrifuged at 136,000 g for 30 min. The pellet was re-suspended in buffer B (300 mM sucrose, 10 mM HEPES, 40 μg/ml PMSF, pH 7.5). A precast Gel for Polyacrilamide Electrophoresis 7.5% Tris-HCl (Bio-Rad Laboratories, Hercules, Calif.) was loaded with 50 μg protein per well. Samples were run at 150 V for 60 min and transferred to PVDF-plus membrane (Osmonics, Westborough, Mass.) at 100 V for 1 h. Membranes were blocked for 1 h at room temperature in TBS-T and 10% horse serum. Monoclonal anti-MRP1 primary antibody (2 μg/ml, mouse IgG1 isotype, Sigma, Saint Louis, Mo.) was applied for 2.5 h. Secondary antibody (peroxidase-conjugated AffiniPure goat anti-mouse IgG, Jackson ImmunoResearch Laboratories, Inc., West Grove, Pa.) was diluted 1:30000 in TBS-T and applied for 30 min. All wash steps were performed in triplicate for 10 min in TBS-T. MRP1 was detected using ECL Plus Western Blotting Detection Reagents (Amersham Biosciences, Buckinghamshire, UK).

Assessment of cytotoxicity. In one exemplary method, membrane integrity of A549, HL-60 and PC-3 cells was used as an index of drug-induced cytotoxicity, and was assessed by monitoring the release of cytosolic lactate dehydrogenase (LDH). LDH activity was measured in the culture medium and cell lysates (50 mM HEPES, Triton X-100 0.5%, pH 7) using a plate reader format as previously described (41). Briefly, 5 μl of cell culture supernatant and lysates were incubated with 0.24 mM NADH in a Tris/NaCl pH 7.2 buffer in 96-well plates for 5 min at 25° C. The reaction was started by the addition of 9.8 mM pyruvate and the consumption of NADH followed at 340 nm for 5 min at 30° C. Percent LDH release was calculated by the following: (supernatant LDH/supernatant LDH+lysate LDH)×100.

Flow cytometry. In one exemplary method, cellular superoxide ($O_2^-$) was measured by flow cytometry analysis using hydroethidine (HE) (30). Untreated and treated HL-60 cells (approximately $10^6$) were exposed to HE (1 μM from 1 mM stock solutions in DMSO) for 30 min, then were centrifuged at 3,500 g for 15 min, and washed once with 1 ml ice-cold PBS. Cells were re-suspended in 0.5 ml ice-cold PBS, and HE oxidation product, i.e., ethidium bromide (EB), analyzed within 30 min using the red channel (PE) of a FACSCalibur flow cytometer from Becton Dickinson Biosciences (San Jose, Calif.). The total number of cell counts was 25,000.

Statistical analysis. In one example, data are presented as means±standard error. Each experimental group consisted of an n≧3 and the results duplicated at least once. Data were subsequently analyzed for significant differences using ANOVA analysis coupled with a Tukey's range test where significance was set at p<0.05 (Prizm v.4, GraphPad).

All of the COMPOSITIONS and/or METHODS and/or APPARATUS disclosed and claimed herein can be made and executed without undue experimentation in light of the present disclosure. While the compositions and methods of this invention have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 2

Proposed Apical Lung Glutathione Transporters.

| Transporter | Tissue expression | Inducers & Activators | Inhibitors |
|---|---|---|---|
| MDR-1 | Lung, Kidney, Liver, GI | Dexamethasone(I), Genistein(A), Quercetin(A) | Apigenin, Reserpine, PSC 833, Diltazem, Verapamil, Acridine Orange |
| MRP-2 | Lung, Liver, GI | Dexamethasone(I), Quercetin(A), Cisplatin(A), Indomethacin(A) | Genistein, Phenobarbital, Probenecid, benzbromarone Glibenclamine, MK-571, Indocyanine Green |
| MRP-4 | Lung, GI, Pancreas, Muscle | Unknown | Unknown |
| CFTR | Lung, GI, Pancreas | S-nitrosoglutathione(I), Ibuprofen(A), Genistein(A), Apigenin(A), Quercetin(A) | Genistein, glibenclamine |

(I)Inducer
(A)Activator

TABLE 3

| Drug | Concentration (μM) | % Increase Over Control * |
|---|---|---|
| p-Aminosalicylic Acid | 100 | 414 [a] |
| Berberine | 100 | 170 [a] |
| Biochanin-A | 50 | 133 [c] |
| Dexamethasone | 50 | 178 [a] |
| Diltiazem | 100 | 119 [b] |
| Indomethacin | 100 | 235 [a] |
| Methylsalicylic Acid | 100 | 169 [a] |
| Propyl Gallate | 50 | 136 [a] |
| Rutin | 100 | 160 [b] |
| Sulfasalazine | 50 | 211 [a] |
| 5-Sulfosalicylic Acid | 50 | 142 [a] |
| Verapamil | 10 | 113 [b] |
| Transwell Studies | | |
| Biochanin-A | 50 | 174 [a] |
| Indomethacin | 100 | 136 [a] |

TABLE 4

| | A549** | | HL-60 | | PC-3 | |
|---|---|---|---|---|---|---|
| Compound | Int. GSH % con. [μM] | LDH rel. % con. [μM] | Int. GSH % con. [μM] | LDH rel. % con. [μM] | Int. GSH % con. [μM] | LDH rel. % con. [μM] |
| Chalcone | <5 [25] | 150 [75] | 100 [25] | 236 [50] | 119 [25] | 229 [50] |
| 2'-HC | <5 [25] | 515 [75] | <5 [25] | 320 [50] | 93 [25] | 227 [25] |
| 2',5'-DHC | <5 [25] | 273 [75] | <5 [25] | 310 [50] | 67 [25] | 246 [50] |
| Flavone | <5 [25] | 164 [75] | 85 [50] | 116 [50] | 84 [25] | 91 [50] |
| 7-HF | <5 [25] | 113 [75] | 56 [50] | 113 [50] | 63 [25] | 96 [50] |
| Chrysin | <5 [25] | 225 [75] | 40 [50] | 195 [50] | 51 [25] | 132 [50] |
| Galangin | <5 [25] | 155 [75] | 69 [50] | 114 [50] | 68 [25] | 140 [50] |
| Apigenin | 9 [25] | 284 [75] | 66 [50] | 259 [50] | 32 [25] | 142 [50] |
| Kaempferol | 7 [25] | 173 [75] | 75 [50] | 128 [50] | 77 [25] | 115 [50] |
| Quercetin | 36 [25] | 175 [75] | 94 [50] | 157 [50] | 95 [25] | 80 [50] |

TABLE 4-continued

| Compound | A549** Int. GSH % con. [μM] | A549** LDH rel. % con. [μM] | HL-60 Int. GSH % con. [μM] | HL-60 LDH rel. % con. [μM] | PC-3 Int. GSH % con. [μM] | PC-3 LDH rel. % con. [μM] |
|---|---|---|---|---|---|---|
| Genistein | 5 [25] | 350 [75] | 57 [75] | 160 [50] | 81 [25] | 131 [50] |
| Biochanin A | <5 [25] | 230 [75] | 20 [75] | 133 [50] | 81 [25] | 127 [50] |
| Naringenin | 17 [25] | 130 [75] | 73 [75] | 95 [50] | 83 [25] | 107 [50] |
| Baicalein | 41 [50] | 206 [75] | 82 [75] | 129 [50] | 100 [50] | 94 [50] |
| Fisetin | 50 [50] | 267 [75] | 16 [50] | 166 [50] | 100 [50] | 109 [50] |
| Morin | 72 [75] | 112 [75] | 86 [75] | 97 [50] | 125 [50] | 80 [50] |
| Myricetin | 55 [75] | 206 [75] | 27 [75] | 139 [50] | 111 [50] | 93 [50] |
| Epicatechin | 47 [75] | 104 [75] | 90 [75] | 76 [50] | 115 [50] | 88 [50] |
| Cyanidin | 82 [75] | 110 [75] | 95 [75] | 110 [50] | 120 [50] | 93 [50] |
| Rutin | 86 [75] | 187 [75] | 98 [75] | 98 [50] | 107 [50] | 95 [50] |
| Resveratrol | 64 [75] | 249 [75] | 61 [75] | 143 [50] | 108 [50] | 135 [50] |
| 2-ME | 49 [50] | 150 [75] | 41 [25] | 265 [25] | 68 [25] | 128 [50] |
| 2-HE | <5 [25] | 150 [75] | 120 [25] | 250 [25] | 228 [25] | 113 [50] |
| β-Estradiol | 41 [50] | nd | 70 [25] | 120 [25] | 98 [25] | nd |
| Curcumin | 53 [50] | 140 [75] | 221 [25] | 180 [25] | 170 [25] | 180 [50] |
| Rotenone | 53 [50] | 170 [75] | <5 [25] | 421 [25] | 74 [25] | 180 [50] |
| Etoposide | 55 [50] | 294 [50] | 7 [25] | 290 [25] | 83 [25] | 124 [50] |
| Verapamil | 14 [50] | 130 [50] | 63 [25] | 125 [25] | 72 [25] | 93 [50] |
| Indomethacin | <5 [25] | 251 [50] | 49 [25] | 126 [25] | 75 [25] | 122 [50] |
| MK-571 | <5 [25] | 249 [50] | 40 [25] | 169 [25] | 41 [25] | 143 [50] |

*Intracellular GSH levels are reported as % compared to control after 24 hours treatment, with standard error ≦±5% (n = 3), and toxicities as % LDH release compared to control after 48 hours treatment, with standard error ≦±10% (n = 4), concentration of compounds shown in brackets as μM (nd, not determined).
**See Table 5 for 2 and 4 hours treatment.

TABLE 5

| Compound [25 μM] | 2 h** | 4 h |
|---|---|---|
| 2',2-DHC | <5 | <5 |
| 2'-HC | <5 | <5 |
| 2',5'-DHC | <5 | <5 |
| 2-HC | <5 | <5 |
| 4-HC | 5.5 ± 0.4 | <5 |
| 2',4',4-THC | 6.8 ± 0.2 | <5 |
| 2',4'-DHC | 22.0 ± 1.8 | <5 |
| 4'-HC | 35.6 ± 2.9 | <5 |
| Chrysin | 47.2 ± 4.0 | 5.2 ± 0.5 |
| Chalcone | 48.5 ± 2.1 | nd |
| 7-HF | 58.1 ± 1.4 | nd |
| MK-571 | 62.6 ± 4.9 | <5 |
| Galangin | 62.9 ± 0.4 | nd |
| 2-HE | 69.0 ± 0.5 | nd |
| Indomethacin | 71.4 ± 2.8 | 7.8 ± 1.2 |
| 7-MF | 78.2 ± 2.4 | nd |
| Apigenin | nd | 17.1 ± 1.4 |
| Kaempferol | nd | 29.6 ± 0.9 |
| Flavone | 89.7 ± 0.6 | 29.7 ± 4.8 |
| Genistein | nd | 34.8 ± 1.1 |
| Biochanin A | nd | 36.8 ± 0.9 |
| 5-HF | nd | 44.7 ± 3.4 |
| Quercetin | nd | 51.0 ± 0.7 |

*Values reported as % compared to control ± standard error (n = 3) (nd, not determined).
**See FIG. 2A using 10 μM.

The invention claimed is:

1. A compound of the formula:

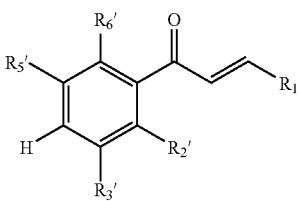

wherein $R_1$ is a positively charged imidazole ring wherein the two nitrogens are substituted with $C_{1-4}$ alkyl substituents; and each of R2', R3', R5' and R6' is independently hydrogen or a hydroxyl protecting group and wherein at least one of R2', R3', R5', or R6' is —OH.

2. The compound of claim 1, wherein R2' or R3' is —OH.

3. The compound of claim 1, wherein R2' and R6' or R2' and R5' or R2' and R3' are hydroxyl groups.

4. The compound of claim 3, wherein R2' and R6' are hydroxyl groups.

5. The compound of claim 1, wherein one of R2', R3', R5' and R6' is —OH and the others are hydrogen.

6. The compound of claim 1, wherein $R_1$ is an imidazolium-2-yl, imidazolium-4-yl or imidazolium-5-yl.

7. The compound of claim 1, wherein $R_1$ is an N—$C_{1-4}$ alkyl imidazolium-2-yl, N—$C_{1-4}$ alkyl imidazolium-4-yl or N—$C_{1-4}$ alkyl imidazolium-5-yl.

8. The compound of claim 1, wherein the 5-membered heteroaryl ring is substituted imidazolium, R2' is a hydrogen, R3' is —OH, R5' is a hydrogen, and R6' is —OH.

9. A pharmaceutical composition comprising one or more compounds of claim 1 or pharmaceutically acceptable salts thereof.

10. The pharmaceutical composition of claim 9, further comprising one or more of a pharmaceutically acceptable additive, carrier or excipient.

11. The pharmaceutical composition of claim 9, further comprising an anti-cancer agent, a thiol-containing compound transporter inducing agent or a combination thereof.

* * * * *